US008067653B2

(12) United States Patent
Bressler

(10) Patent No.: US 8,067,653 B2
(45) Date of Patent: Nov. 29, 2011

(54) METHODS FOR PRODUCING FUELS AND SOLVENTS

(75) Inventor: David Bressler, St. Albert (CA)

(73) Assignee: The Governors of the University of Alberta, Edmonton, Alberta (CA)

( * ) Notice: Subject to any disclaimer, the term of this patent is extended or adjusted under 35 U.S.C. 154(b) by 355 days.

(21) Appl. No.: 11/776,047

(22) Filed: Jul. 11, 2007

(65) Prior Publication Data

US 2008/0034645 A1 Feb. 14, 2008

Related U.S. Application Data

(60) Provisional application No. 60/807,358, filed on Jul. 14, 2006.

(51) Int. Cl.
*C10L 1/04* (2006.01)
(52) U.S. Cl. .............. 585/240; 585/16; 585/14; 44/300; 44/308
(58) Field of Classification Search .............. 44/307, 44/308; 435/142; 208/87; 585/240, 16, 585/14
See application file for complete search history.

(56) References Cited

U.S. PATENT DOCUMENTS

| 2,437,438 A | | 3/1948 | Petroff et al. |
| 4,235,702 A | * | 11/1980 | Smith ............................ 208/87 |
| 4,554,397 A | | 11/1985 | Stern et al. |
| 4,992,605 A | | 2/1991 | Craig et al. |
| 5,225,580 A | | 7/1993 | Zinnen |
| 5,578,090 A | | 11/1996 | Bradin |
| 5,705,722 A | | 1/1998 | Monnier et al. |
| 5,917,068 A | | 6/1999 | Barnicki et al. |
| 7,491,858 B2 | | 2/2009 | Murzin et al. |
| 2003/0089027 A1 | * | 5/2003 | Jordan ............................ 44/307 |
| 2003/0089028 A1 | * | 5/2003 | Jordan ............................ 44/307 |
| 2004/0230085 A1 | | 11/2004 | Jakkula et al. |
| 2007/0068848 A1 | | 3/2007 | Monnier et al. |
| 2007/0277429 A1 | * | 12/2007 | Jackam et al. ................. 44/308 |
| 2008/0305531 A1 | * | 12/2008 | Lam et al. ..................... 435/142 |

FOREIGN PATENT DOCUMENTS

| GB | 175974 | 6/1923 |
| GB | 218278 | 4/1925 |
| WO | 9745197 | 12/1997 |

(Continued)

OTHER PUBLICATIONS

Ayhan Demirbas; "Biodiesel fuels from vegetable oils via catalytic and non-catalytic supercritical alcohol transesterifications and other methods: a survey," Energy Conversion & Management; 2003; 17 pgs; pp. 2093-2109, vol. 44; Elsevier Science Ltd.,Turkey.

(Continued)

*Primary Examiner* — Ellen McAvoy
*Assistant Examiner* — Chantel Graham
(74) *Attorney, Agent, or Firm* — Gardner Groff Greenwald & Villanueva, P.C.

(57) ABSTRACT

Described herein are methods for producing fuels and solvents from fatty acid resources. In general, the pyrolysis products of fatty acids are extracted in order to remove residual fatty acids and produce very pure hydrocarbon compositions composed of alkanes and alkenes. The fatty acids removed from the extraction step can be further pyrolyzed to produce additional hydrocarbons or, in the alternative, the fatty acids can be isolated and used in other applications. Also disclosed herein are fuels and solvents produced by the methods described herein.

15 Claims, 55 Drawing Sheets

FOREIGN PATENT DOCUMENTS

| WO | 2004035714 | 4/2004 |
|---|---|---|
| WO | 2007027955 | 3/2007 |
| WO | 2007068798 | 6/2007 |
| WO | 2007027669 | 8/2007 |

OTHER PUBLICATIONS

M.E. Tat, J.H. Van Gerpen; "Biodiesel Blend Detection with a Fuel Composition Sensor," Applied Engineering in Agriculture, 2003; 8 pgs; pp. 125-131; vol. 19(2); American Society of Agricultural Engineers.

Mustafa E. Tat, Jon H. Van Gerpen; "The Kinematic Viscosity of Biodiesel and Its Blends with Diesel Fuel," JAOCS; 1999; 3 pgs; pp. 1511-1513; vol. 76; Iowa State University, Ames, Iowa.

Anjana Srivastava, Ram Prasad; "Triglycerides-based diesel fuels; Renewable & Sustainable Energy Reviews," 2000; 23 pgs; pp. 111-133; vol. 4; Elsevier Science Ltd., India.

A.V. Bridgwater, G.V.C. Peacocke; "Fast pyrolysis processes for biomass; Renewable & Sustainable Energy Reviews," 2000; 73 pgs; pp. 1-73; vol. 4; Elsevier Science Ltd.

Michael S. Graboski, Robert L. McCormick; "Combustion of Fat and Vegetable Oil Derived Fuels in Diesel Engines," Prog. Energy Combust. Sci., 1998; 40 pgs; pp. 125-164; vol. 24; Elsevier Science Ltd., Great Britain.

S. Sensoz, D. Angin, S. Yorgun; "Influence of particle size on the pyrolysis of rapeseed (*Brassica napus* L.): fuel properties of bio-oil," Biomass & Bioenergy; 2000; 9 pgs; pp. 271-279; vol. 19; Elsevier Science Ltd., Turkey.

M. Predel, W. Kaminsky; "Pyrolysis of Rape-Seed in a Fluidised-Bed Reactor," Bioresource Technology 66; 1998; 5 pgs; pp. 113-117; Elsevier Science Ltd., Germany.

F Karaosmanoglu, E. Tetik, E. Gollu; "Biofuel production using slow pyrolysis of the straw and stalk of the rapeseed plant," Fuel Processing Technology, 1999; 12 pgs; pp. 1-12; vol. 59; Elsevier Science B.V., Turkey.

J. Piskorz, P. Majerski, D. Radlein, A. Vladars-Usas, D.S. Scott; "Flash Pyrolysis of cellulose for production of anhydro-oligomers," Journal of Analytical and Applied Pyrolysis, 2000; 22 pgs; pp. 145-166; vol. 56; Elsevier Science B.V., Canada.

Mustafa E. Tat, Jon H. Van Gerpen; "The Specific Gravity of Biodiesel and Its Blends with Diesel Fuel," JAOCS, 2000; 5 pgs; pp. 115-119; vol. 77, No. 2.

K.D. Maher, D.C.Bressler; "Pyrolysis of triglyceride materials for the production of renewable fuels and chemicals," Bioresource Technology, 2007; 18 pgs; pp. 2351-2368; vol. 98.

Katsumori Tanabe, Murray R. Gray; "Role of Fine Solids in the Coking of Vacuum Residues," Energy and Fuels, 1997; 4 pgs; pp. 1040-1043; vol. 11.

David C. Bressler, Murray R. Gray; "Hydrotreating Chemistry of Model Products from Bioprocessing of Carbazoles" Energy and Fuels, 2002; 11 pgs; pp. 1076-1086; vol. 16.

Ayhan Demirbas; "Diesel Fuel from Vegetable Oil via Transesterification and Soap Pyrolysis",Energy Sources, 2002; 8 pgs; pp. 835-841; vol. 24.

Paul H.L. Moquin, Feral Temelli, Helena Sovova, Marleny D.A. Saldana;"Kinetic modeling of glycerolysis-hydrolysis of canola oil in supercritical carbon dioxide media usin equilibrium data," The Journal of Supercritical Fluids, 2006; 8 pgs; pp. 417-424; vol. 37.

A.T. Erclyes, L. Dandik, and F.S. Erkal; "The Decomposition of Secondary Esters of Castor Oil with Fatty Acids",JOACS; Sep. 1991; 4 pgs; pp 642-645; vol. 68, No. 9.

Patent Cooperation Treaty; International Search Report and the Written Opinion; Aug. 27, 2008; 7 pages; Alexandria, Virginia.

Patent Cooperation Treaty; International Search Report and the Written Opinion; Sep. 4, 2008; 13 pages; Gatineau, Quebec, Canada.

Snare et al. (Jun. 28, 2006) Heterogeneous Catalytic Deoxygenation of Steric Acid for Production of Biodiesel, Ind. Eng. Chem. Res., 45, 5708-5715.

Jaw, "The Thermal Decomposition Behaviors of Stearic Acid, Paraffin Wax and Polyvinyl Butyral", Thermochima Acta, pp. 165-168, 2001, Elsevier Science B.V., Taiwan.

Alencar, "Pyrolysis of Tropical Vegetable Oils", J. Agric. Food Chem. vol. 31, No. 6, pp. 1268-1270, 1983, American Chemical Society, USA.

Office Action dated Nov. 8, 2010 for Ukrainian Application No. 200901198.

Kirk Othmer, "Carboxylic Acid (Manufacture)," Encyclopedia of Chemical Technology, Dec. 31, 1978.

European Search Report dated Jul. 22, 2011 for European Application No. 07849051.3.

Office Action for Russian Application No. 2009105075/04 dated Jun. 30, 2011.

Foglia, et al. "Decarbonylation Dehydration of Fatty Acids to Alkenes in the Presence of Transition Metal Complexes," Journal of the American Oil Chemists Society, vol. 53, Dec. 1976, pp. 737-741.

Maier, et al. "Gas Phase Decarboxylation of Carboxylic Acids," Chem. Ber. 115, pp. 808-812 (1982).

Watanabe, et al. "Decomposition of a Long Chain Saturated Fatty Acid with Some Additives in Hot Compressed Water," Energy Conversion and Management, 47, (2006), pp. 3344-3350.

Zhang, et al. "Catalytic Decarboykation of Fatty Acids by Iron-containing Minerals in Immature Oil Source Rocks at Low Tempature," Chinese Science Bulletin, vol. 44, No. 16., Aug. 1999, pp. 1523-1527.

Zhe, et al. "Catalytic Decarboxylations of Fatty Acids in Immature Oil Source Rocks," Science in China, vol. 46, No. 12, Dec. 2003, pp. 1250-1260.

Office Action dated Mar. 14, 2011 for Ukrainian application No. 200901198.

Serguchev et al. "Oxidate Decarboxylation of Carboxylic Acids", Russian Chemical Reviews, 1980, vol. 49, pp. 227-2285, Russia.

Kubickova et al., "Hydrocarbons for diesel fuel via decarboxylation of vegetable oils", Catalysis Today, 2005, vol. 106, pp. 197-200, Elsevier B.V., Finland.

\* cited by examiner

METHODS FOR PRODUCING FUELS AND SOLVENTS

CROSS REFERENCE TO RELATED APPLICATION

This application claims priority upon U.S. provisional application Ser. No. 60/807,358, filed Jul. 14, 2006. This application is hereby incorporated by reference in its entirety for all of its teachings.

BACKGROUND

There are increasing social and economic pressures to develop renewable energy sources as well as renewable and biodegradable industrial and consumer products and materials. The catalytic conversion of natural feedstocks to value-added products has resulted in new approaches and technologies whose application spans across the traditional economic sectors. There is a new focus on biorefining, which can be described as the processing of agricultural and forestry feedstocks capturing increased value by processing them into multiple products including platform chemicals, fuels, and consumer products. The conversion of tallow and other organic oils to biodiesel has been previously studied in depth. Traditionally, this conversion involves the trans-esterification of the triglyceride to produce three methyl-esterified fatty acids and a free glycerol molecule. The chemical, Theological, and combustion properties of the resulting "biodiesel" have also been extensively investigated. Unfortunately, these methyl-ester based fuels have been shown to be far more susceptible to oxidation and have lower heating values than the traditional petroleum based diesel fuels. As a result the traditional biodiesels must be blended with existing diesel stock and may also have to be supplemented with antioxidants to prolong storage life and avoid deposit formation in tanks, fuel systems, and filters.

If methyl-esterification can be considered a clean controlled reaction, a relatively crude alternative that has been utilized previously in industry is pyrolysis. Pyrolysis involves the use of a thermal treatment of an agricultural substrate to produce a liquid fuel product. Most literature reports utilize raw unprocessed agricultural commodities to produce a value-added fuel. Many different approaches to pyrolysis as a mechanism of producing a liquid fuel have been reported in the literature and fall under various regimes including flash, fast, and slow pyrolysis. The pyrolysis of a variety of agricultural products under these different regimes has been previously investigated, including castor oil, pine wood, sweet sorghum, and canola. Depending on the conditions used including the temperature used, residence time, and purity of substrate the balance of products produced varies between vapors, liquids, and residual solids (char).

One of the few studies to look at the pyrolysis of fatty acids instead of the triglycerides or more complex substrates focused on the pyrolysis of the salt of the fatty acid. The conditions used in the study were such that a homogeneous decarboxylation product was not produced. Instead a mixture of hydrocarbon breakdown products was produced and was not identified by the authors. In general, the decarboxylation of carboxylic acids that do not contain other interacting functional groups at high temperature and pressure is poorly understood in the literature. Gaining a better fundamental understanding of the chemistry and methodologies necessary to promote decarboxylation of fatty acids, or cracking reactions to larger smaller alkanes and alkenes, may allow the future development of new fuel and solvent technologies. In one aspect, described herein is the thermal treatment of protonated free fatty acids under anoxic conditions. Processes of this nature hold the potential to produce a higher grade fuel than the traditional biodiesels, and yet would potentially produce higher yields of desirable products than pyrolysis.

SUMMARY

Described herein are methods for producing fuels and solvents from fatty acid resources. Also disclosed herein are fuels and solvents produced by the methods described herein. The advantages of the materials, methods, and articles described herein will be set forth-in part in the description which follows, or may be learned by practice of the aspects described below. The advantages described below will be realized and attained by means of the elements and combinations particularly pointed out in the appended claims. It is to be understood that both the foregoing general description and the following detailed description are exemplary and explanatory only and are not restrictive.

BRIEF DESCRIPTION OF FIGURES

The accompanying Figures, which are incorporated in and constitute a part of this specification, illustrate several aspects described below.

DETAILED DESCRIPTION

Figure 1:
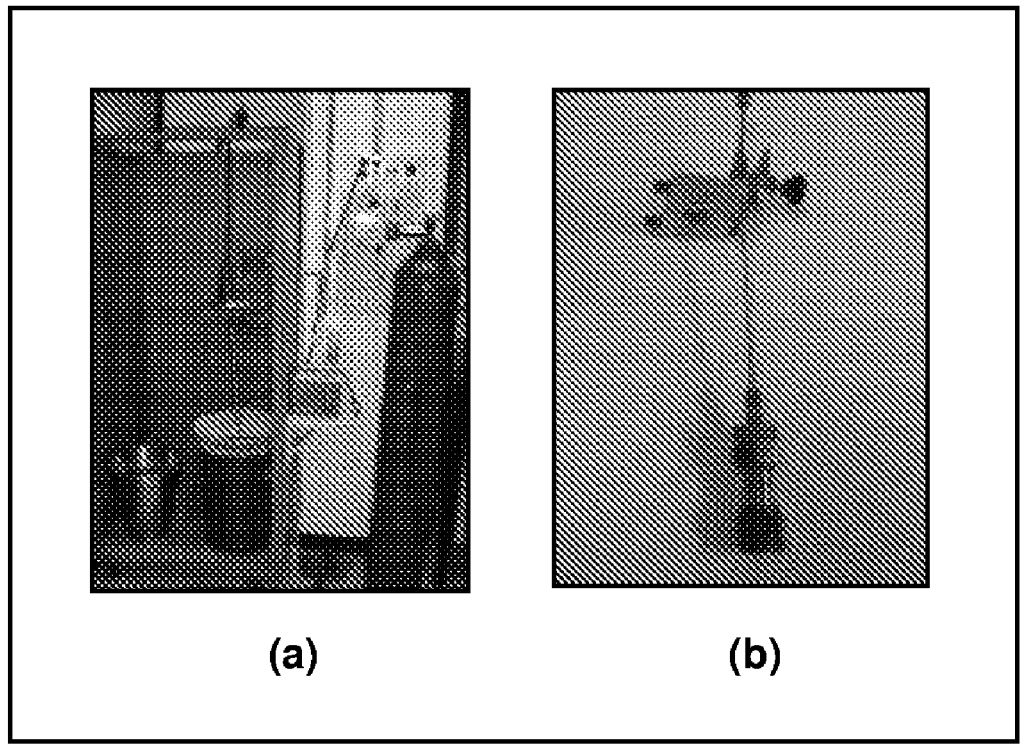
FIG. 1 shows a schematic of (a) sand bath and purge system and (b) microreactor.

Before the present materials, articles, and/or methods are disclosed and described, it is to be understood that the aspects described below are not limited to specific compounds, synthetic methods, or uses as such may, of course, vary. It is also to be understood that the terminology used herein is for the purpose of describing particular aspects only and is not intended to be limiting.

In this specification and in the claims that follow, reference will be made to a number of terms that shall be defined to have the following meanings:

Throughout this specification, unless the context requires otherwise, the word "comprise," or variations such as "comprises" or "comprising," will be understood to imply the inclusion of a stated integer or step or group of integers or steps but not the exclusion of any other integer or step or group of integers or steps.

It must be noted that, as used in the specification and the appended claims, the singular forms "a," "an" and "the" include plural referents unless the context clearly dictates otherwise. Thus, for example, reference to "an oil" includes a single oil or mixtures of two or more oils.

"Optional" or "optionally" means that the subsequently described event or circumstance can or cannot occur, and that the description includes instances where the event or circumstance occurs and instances where it does not.

Described herein are methods for producing fuels and solvents from fatty acid resources. In one aspect, the method comprises:
a. separating one or more fatty acids from the fatty acid resource; and
b. converting the fatty acid to one or more alkanes, alkenes, or a mixture thereof.

The term "fatty acid resource" as defined herein is any source of free fatty acid or a precursor to a free fatty acid upon subsequent processing. For example, a triglyceride is a precursor to a free fatty acid, where hydrolysis of the glycerol group produces the free fatty acid. Examples of fatty acid resources include, but are not limited to, vegetable oil, animal fats, spent cooking oil, lipids, phospholipids, soapstock, or other sources of triglycerides, diglycerides or monoglycerides. In one aspect, the vegetable oil comprises corn oil, cottonseed oil, canola oil, rapeseed oil, olive oil, palm oil, peanut oil, ground nut oil, safflower oil, sesame oil, soybean oil, sunflower oil, algae oil, almond oil, apricot oil, argan oil, avocado oil, ben oil, cashew oil, castor oil, grape seed oil, hazelnut oil, hemp seed oil, linseed oil, mustard oil neem oil, palm kernel oil, pumpkin seed oil, rice bran oil, walnut oil, a combination thereof. In another aspect, the animal fat comprises blubber, cod liver oil, ghee, lard, tallow, derivatives thereof (e.g., yellow grease, used cooking oil, etc.), or a combination thereof.

It is contemplated that the fatty acid resource can be further purified prior to separation step (a). For example, the fatty acid resource can be distilled or extracted to remove any undesirable impurities. In the alternative, the fatty acid resource can be used as-is and proceed to separation step (a). The source of the fatty acid resource will determine if any pre-purification steps are required.

Separation step (a) involves removing or isolating one or more fatty acids from the fatty acid resource. A number of different techniques are known in the art for the isolation and purification of fatty acids. For example, U.S. Pat. No. 5,917,501 discloses a process for isolating fatty acids. The process involves hydrolyzing a naturally occurring lipid mixture containing phospholipids, triglycerides, and sterols to form a two-phase product containing a fatty acid phase comprised of free fatty acids and sterols, and an aqueous phase comprised of water, glycerol, and glycerol phosphoric acid esters. The aqueous phase is separated from the fatty acid phase and the crude fatty acid phase is heated to convert the free sterols to fatty acid sterol esters. The free fatty acids are distilled from the fatty acid sterol esters to yield purified fatty acids, which are free of cholesterol and other sterols, and phosphorous compounds. In other aspects, the fatty acid resource is exposed to acid in order to hydrolyze a fatty acid precursor present in the fatty acid resource to produce the corresponding fatty acid. For example, vegetable oils are rich in triglycerides, which upon acid hydrolysis, produce the free fatty acid and glycerol.

After the separation step, it is desirable to produce a pure or substantially pure form of the fatty acid. The phrase "substantially pure" as used herein is defined as greater than 90% by weight fatty acid content. The presence of impurities can adversely affect the final composition of the fuel or solvent. For example, if sulfur, oxygen, or nitrogen compounds are present in the fatty acid prior to step (b), undesirable product characteristics result including high sulfur or nitrogen emissions during combustion or side-reactions may occur during step (b) such as the formation of undesirable aromatic compounds.

The nature of the fatty acid will vary depending upon the fatty acid resource. The fatty acid can be a saturated fatty acid, an unsaturated fatty acid, or a combination thereof. Examples of fatty acids include, but are not limited to, butyric acid, lauric acid, myristic acid, palmitic acid, stearic acid, arachidic acid, alpha-linolenic acid, docosahexaenoic acid, eicosapentaenoic acid, linoleic acid, arachidonic acid, oleic acid, erucic acid, a naturally derived fatty acid from a plant or animal source, or a combination thereof. It is contemplated that the fatty acid can be the free acid or the salt/ester thereof. The fatty acid can also be a mixture of fatty acids.

The second step involves converting the fatty acid(s) to one or more alkanes, alkenes, or mixtures thereof. In general, during the conversion step, the fatty acids are decarboxylated and cracked to produce $CO_2$ and the alkanes or alkenes. The length of the alkane or alkene chain will vary depending upon the fatty acid and reaction parameters, which will be discussed in detail below. In general, the alkanes and alkenes are from $C_1$ to $C_{20}$ hydrocarbons. For example, decarboxylation of stearic acid, which has the formula $CH_3(CH_2)_{16}COOH$, produces $CH_3(CH_2)_{15}CH_3$, shorter alkanes and alkenes, and $CO_2$.

In one aspect, the conversion of the fatty acid to the alkane and/or alkene comprises heating the fatty acid to convert all or substantially all of the fatty acid to an alkane, an alkene, or a mixture thereof. The temperature of the heating step can vary amongst different parameters. In one aspect, the temperature of the heating step is from 220° C. to 650° C., 300° C. to 650° C., 350° C. to 650° C., 350° C. to 600° C., or 250° C. to 500° C. Other parameters to consider are the duration of the heating step and the pressure at which the heating step is conducted. The pressure can range from ambient to 2,000 psi, and the duration of the heating step can be from seconds up to 12 hours. In one asepct, the heating step is from two seconds up to 8 hours. In another aspect, the heating step is performed under an inert atmosphere such as, for example, nitrogen or argon.

By varying reaction conditions during the conversion of the fatty acid to the alkane/alkene, one of ordinary skill in the art can produce short or long chain alkanes/alkenes for fuels and solvents. For example, prolonged heating at elevated temperatures can produce short chain alkanes/alkenes that can be useful as fuels. Alternatively, long chain alkanes/alkenes can be produced by one of ordinary skill in the art by reducing the heating time and temperature. If short chain alkanes or alkenes are produced, reaction conditions can be controlled such that these products are gasses (e.g., methane, propane, butane, etc.) that can be readily removed from the reactor.

In another aspect, the use of a decarboxylation catalyst can be used to facilitate the conversion of the fatty acid to the alkane or alkene. Depending upon the selection of the decarboxylation catalyst, the catalyst can reduce the heating temperature and time. This is desirable in certain instances, particularly if degradation of the alkane/alkene or side reactions (e.g., aromatization) are to be avoided. Examples of decarboxylation catalysts include, but are not limited to, activated alumina catalysts.

Steps (a) and/or (b) can be performed in batch, semi-batch, or continuous modes of operation. For example, with respect to step (b), a continuous reactor system with unreacted acid recycle could be employed to enhance the yield of desirable alkane/alkene by limiting the duration and exposure of the alkane/alkene in the high temperature reactor. Carbon dioxide and small hydrocarbon products could be recovered, with the gas phase hydrocarbons used as fuel for the reactor or other applications. When a continuous reactor system is used, process conditions can be optimized to minimize reaction temperatures and times in order to maximize product yields and composition. As the reaction can be adjusted to select for a preferred carbon chain length (long, short or medium), the technology has the capability of enriching for a particular product group. From these groups, individual chemicals could be recovered, purified, and sold as pure platform chemicals.

The methods described herein provide numerous advantages over current techniques for producing bio-fuel. As described above, the methods described herein can be used to produce either solvents or fuels that are similar to tradiational diesel fuel. The methods utilize renewable resources to create a non-petroleum based sustainable fuel source free of aromatic compounds. The products formed are chemically much more uniform than other high temperature processes currently used. For example, the fuels or solvents produced herein are substantially free of aromatic compounds, where the term "substantially free" is defined as less than 5% by weight aromatic compounds. It is also contemplated that no aromatic compounds are present in the fuels or solvents. It is anticipated the methods described herein will provide higher product yields than other pyrolysis technologies and will produce a fuel much more similar to diesel than biodiesel. The products will not have the problems of biodiesel in that they will be oxidatively stable and will have pour points similar to conventional diesel fuel. Finally, the imput costs are expected to be lower using the methods described herein when compared to competitive, exisiting biodiesel technologies. In particular, the process does not require a hydrogenation step to produce hydrocarbons, which adds significant cost to the process.

EXAMPLES

The following examples are put forth so as to provide those of ordinary skill in the art with a complete disclosure and description of how the materials, articles, and methods described and claimed herein are made and evaluated, and are intended to be purely exemplary and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of reaction conditions, e.g., component concentrations, desired solvents, solvent mixtures, temperatures, pressures and other reaction ranges and conditions that can be used to optimize the product purity and yield obtained from the described process. Only reasonable and routine experimentation will be required to optimize such process conditions.

I. Materials and Chemicals

The chemicals used in the investigation, excluding the reactor feedstocks below, are listed in Table 1.

The feedstocks used in these experiments included:
(1) Stearic acid (95%) purchased from Sigma (St. Louis, Mo.)
(2) Oleic acid purchased from Sigma (St. Louis, Mo.)
(3) Poultry tallow from Lomax Inc. (Montreal, Quebec)
(4) Bleached fancy (BF)
(5) Yellow grease (YG)
(5) Canola oil purchased locally from a Canadian Department Store.

Table 2 shows the fatty acid composition of the feed fats and oil. Table 3 shows the percentage of saturated and unsaturated fatty acid in feed fats and oil.

II. Experimental Equipment

Microreactors and Sand Bath

Pyrolysis reactions were conducted in 15 ml batch microreactors (also referred to as the reactors) heated with a fluidized sand bath as shown in FIG. 1. The experimental set-up consisted of three main components including:
(1) stainless steel microreactors;
(2) microreactor purge system; and
(3) fluidized sand bath system for heating.

Batch Microreactors

Figure 2:
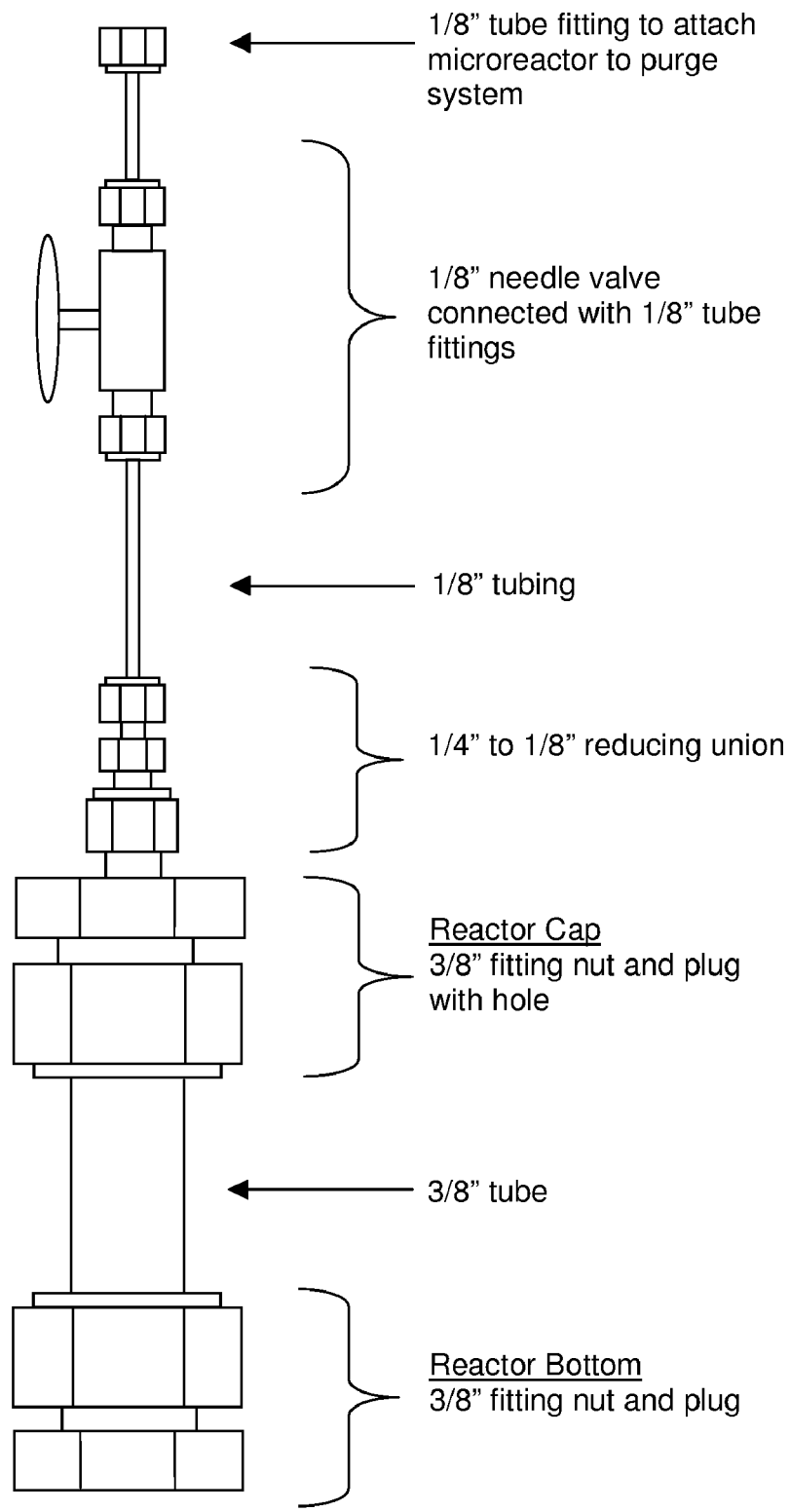
FIG. 2 shows a schematic of closed microreactor.

The 15 ml microreactors used in these experiments were constructed with stainless steel (S.S.) Swagelok® fittings and tubing. A schematic of the closed microreactor is shown in FIG. 2. The microreactors consisted of a bottom cap, central tube, and a top cap with a ¼" opening. Stainless steel tubing (⅛"), approximately 15 cm in length, was connected to this opening with a reducing union and a needle valve was situated near the end of this tube (approximately 13 cm above the reactor top) to open and close the reactor. A mount (not shown in schematic) was also attached to this tubing so that the microreactors could be attached to the sand bath system.

Replacing the Reactors

The microreactors were used until they could not be properly sealed or seized during the reaction and could not be opened, at which time they were replaced. Typically, microreactors lasted between 10-20 reactions.

Microreactor Purge System

Figure 3:
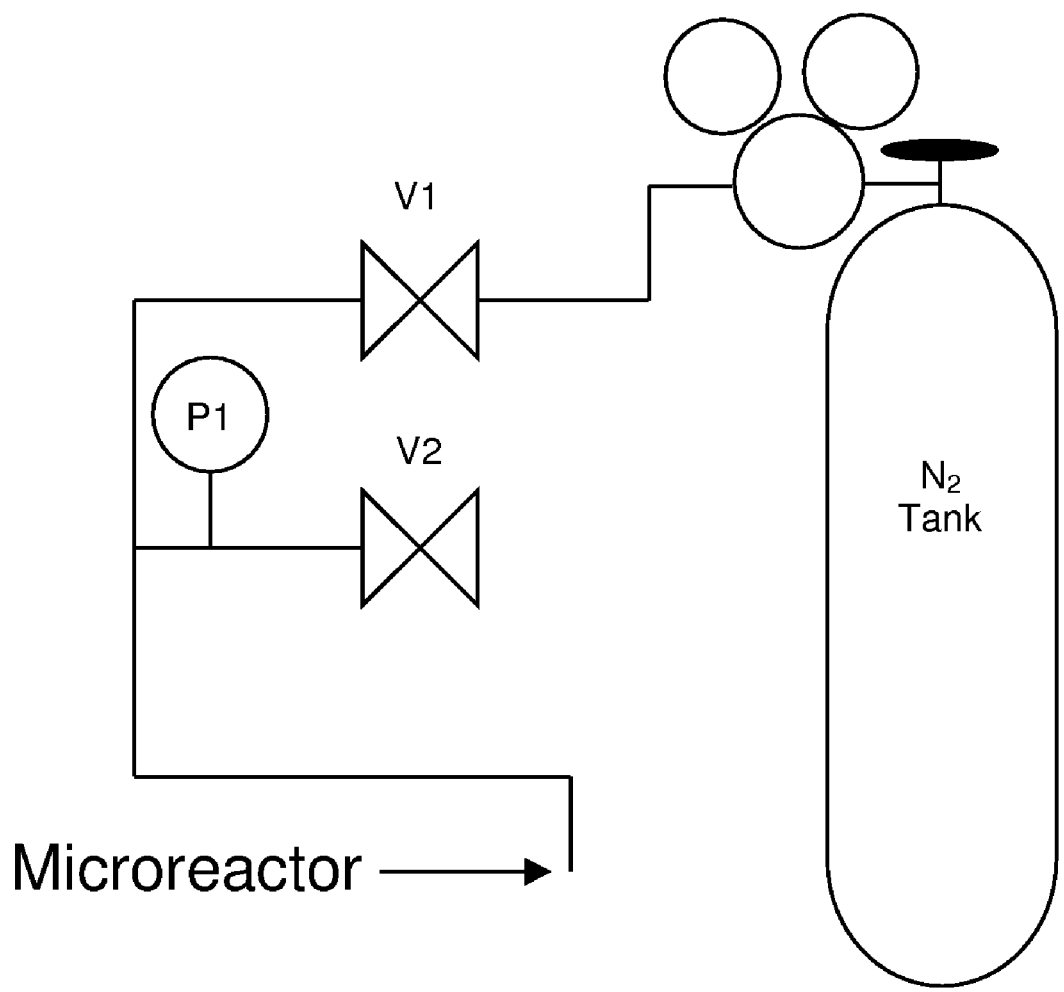
FIG. 3 shows a schematic of the microreactor purge system.

The microreactor design allows for connection to a gas cylinder for pressurization or purging. A schematic of the microreactor purge system used in this work is shown in FIG. 3. The pressure was set by reading P1 and adjusting the tank regulator. The microreactors were connected to the purge system and $V_1$, $V_2$ and the microreactor valve (not shown on schematic) were opened to allow nitrogen into the reactor.

Sand Bath System

Figure 4:
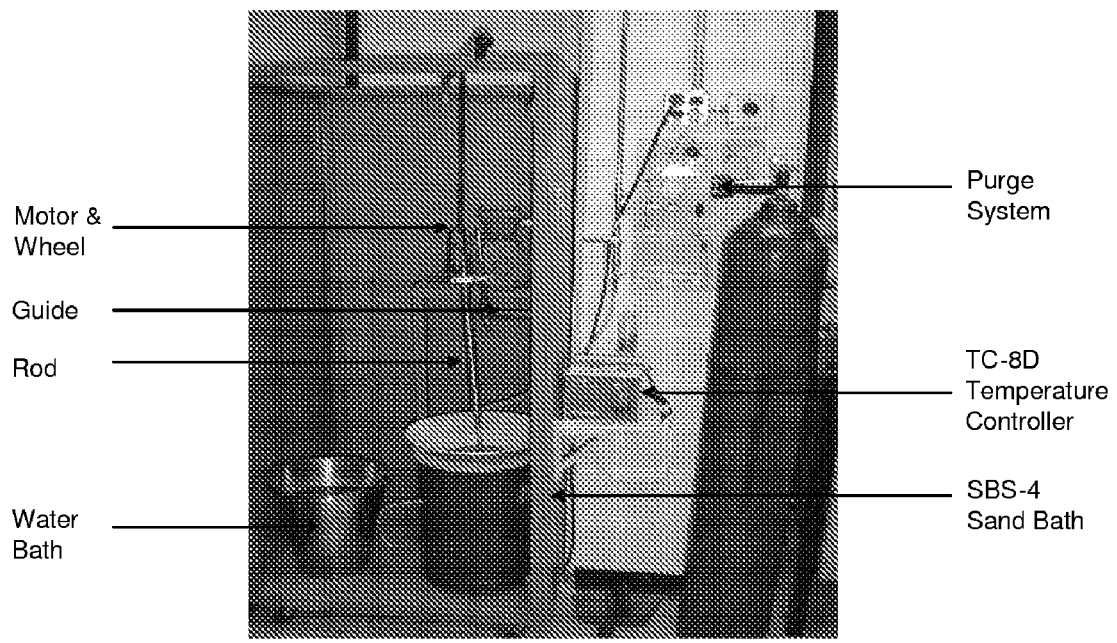
FIG. 4 shows a sand bath system.
Figure 5:
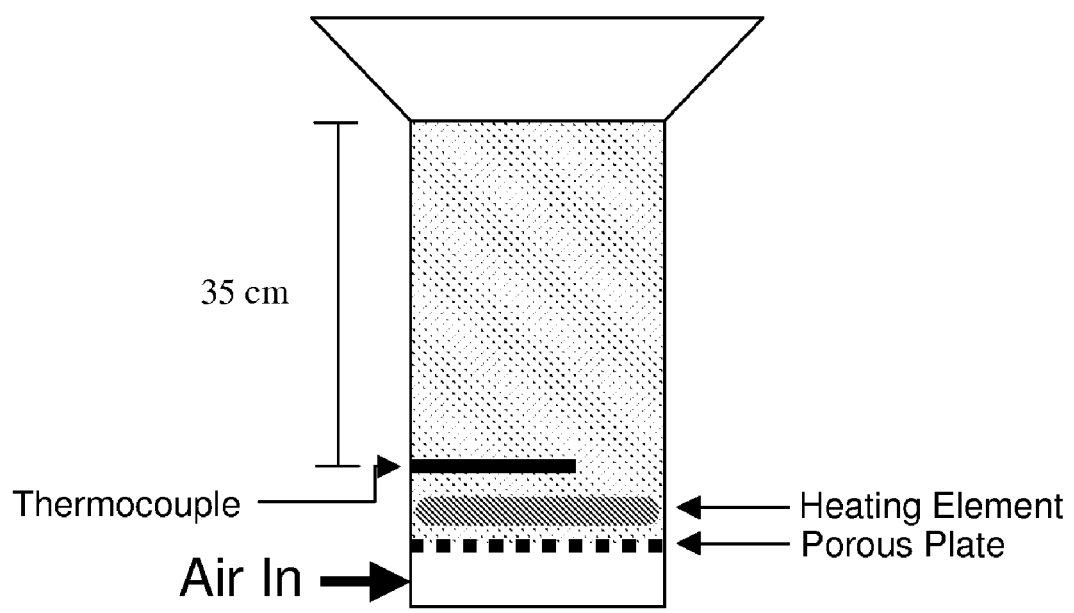
FIG. 5 shows a schematic of a Techne SBS-4 sand bath.

The microreactors were heated in a Techne Model SBS-4 fluidized sand bath (Burlington, N.J.). The main components of the sand bath system are highlighted in FIG. 4 and include the sand bath, motor and arm, air supply, and temperature controller. A schematic of the sand bath is shown in FIG. 5 and its dimensions are presented in Table 4. The sand bath was filled to approximately 1-2" below the top with aluminum oxide sand. To fluidize the sand, compressed air was blown into the bath near the bottom and through a porous plate for more uniform air distribution. A Techne TC-8D temperature controller (Burlington, N.J.) was used to maintain the bath at a constant temperature throughout the reaction. The temperature of the bath was measured by a K-type thermocouple located near the center of the bath. The heating elements were located at the bottom of the sand bath, above the porous plate. An off-center wheel connected to a motor and arm was used to agitate the microreactor for the duration of the reaction.

Modified Reactors for Measurement of Internal Reaction Conditions

Figure 6:
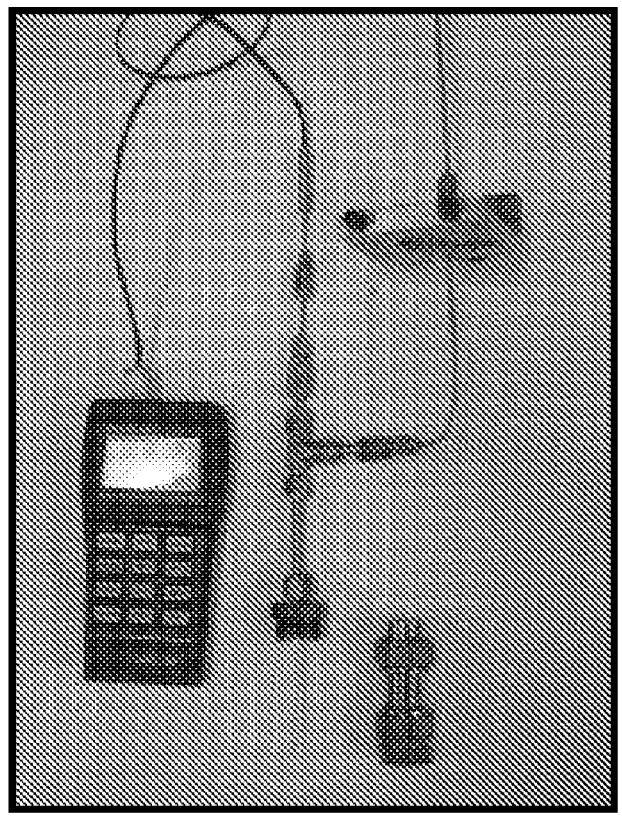
FIG. 6 shows a schematic of modified reactor for measuring internal reactor temperature.
Figure 7:
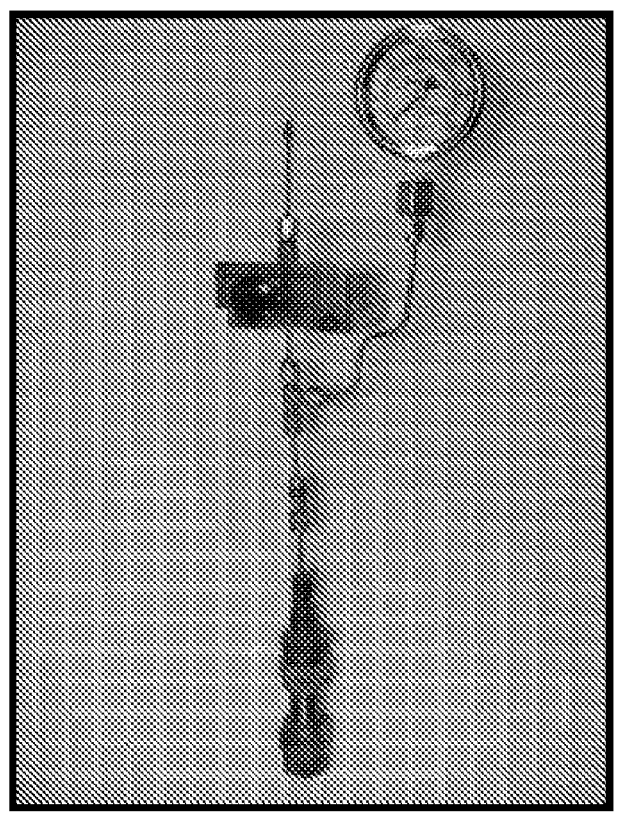
FIG. 7 shows a schematic of the modified reactor for measuring internal reactor pressure.

The batch microreactors were modified to allow measurement of temperature and pressure inside the reactors during the reaction runs. A 1/16" K-type thermocouple (Aircom Industries, Edmonton, AB) was inserted through the top of one of the reactors so the tip was situated approximately 1 mm above the reactor bottom. The thermocouple was connected to the reactor mount tubing using Swagelok® fittings as shown in FIG. 6. The thermocouple was connected to a Digi-Sense Dual JTEK thermocouple thermometer (Cole-Parmer Instrument Company, Vernon Hills, Ill.) to measure the temperature. FIG. 7 shows a second modified reactor for measuring pressure. A Swagelok® pressure gauge (Swagelok, Edmonton, AB) was attached to the reactor mount tubing with Swagelok® fittings.

III. Experimental Procedure

Pyrolysis Reactions

All pyrolysis reactions were conducted in the microreactors. Prior to loading the reactors, the fluidized sand bath was turned on and the temperature controller was set to the desired temperature for that particular reaction. The airflow into the reactor was adjusted so that the sand fluidized enough to form bubbles 1-2" in diameter or just even with the top of the sand bath. The sand bath was allowed to heat up until it reached the steady state temperature as determined by a stable temperature reading on the controller for at least 15 minutes. Heating times ranged between 1.5 and 2.5 hours depending on the set temperature. As the sand bath heats, the air also heats and expands causing the amount of fluidization and the bubble size to increase. To keep the bubble size constant, the airflow was adjusted manually throughout the heating process.

Between reactions the microreactors were scrubbed thoroughly with metal brushes, washed with soap and water, and rinsed with distilled water and wash acetone to ensure they were completely clean and free of residue from the previous reaction. After the microreactors were completely dry, feedstock was weighed into the reactor. Anti-seize lubricant was applied to the threading on the reactor cap and the reactor was closed and tightened. The microreactor was connected to the nitrogen purge system, all valves were opened, and the microreactors were tested for leaks using Swagelok Snoop®. If a leak was detected, the microreactor was removed from the purge system and re-tightened. If a seal could not be obtained after being re-tightened several times, the microreactor was replaced. Once the microreactor was completely sealed and free of leaks, it was purged three times (filled and emptied) before closing the microreactor valve and disconnecting from the purge system.

Once the microreactor was prepared for the reaction, it was attached to the sand bath rod and lowered into the center of the sand bath. The position of the microreactors on the rod was kept constant so that the microreactors were always in approximately the same location in the bath. The microreactors were positioned so they did not contact any part of the sand bath and were completely immersed in the sand. The motor was switched on and timing of the reaction commenced when the arm began agitating. Upon completion of the reaction, the microreactors were lifted from the sand bath and immediately quenched in a bucket of room temperature water to end the reaction. The reactors were vented in the fumehood to release any gaseous products formed during the reactions and opened for extraction unless the gas products were collected for analysis as described below.

To measure the internal reactor temperature and pressure reactors were loaded and purged as normal, however, the modified reactor mounts described below were used. The temperature was recorded by reading the digital thermometer every 30 seconds for the first 10 minutes of the reaction, at every minute from 10-15 minutes and then again at 30, 45, and 60 minutes. The pressure was recorded throughout the run as well as after quenching to determine the amount of pressure generated from the formation of gaseous product.

Extraction of Reaction Products

The reaction products were extracted from the microreactor using 10 ml of pentane spiked with internal standard unless otherwise specified. Nonadecanoic methyl ester was used as the internal standard and was prepared with pentane in concentrations of approximately 0.5 or 1 mg/ml. The pentane/internal standard mixture was measured into the microreactor using a displacement pipette and stirred so that any solid material in the microreactor was scraped off the microreactor sides and broken apart. After approximately 15 minutes, the liquid extract was transferred to a sample vial. All products were stored in dram vials with screw tops and Teflon® liners and stored at 4° C.

Nonadecanoic acid was chosen as an internal standard because it is similar in structure to the starting compound. When this standard was run on GC-FID it gave a sharp clean peak and did not overlap with any of the potential pyrolysis products.

Gas Chromatography (GC)

Liquid Extracts

Figure 8:
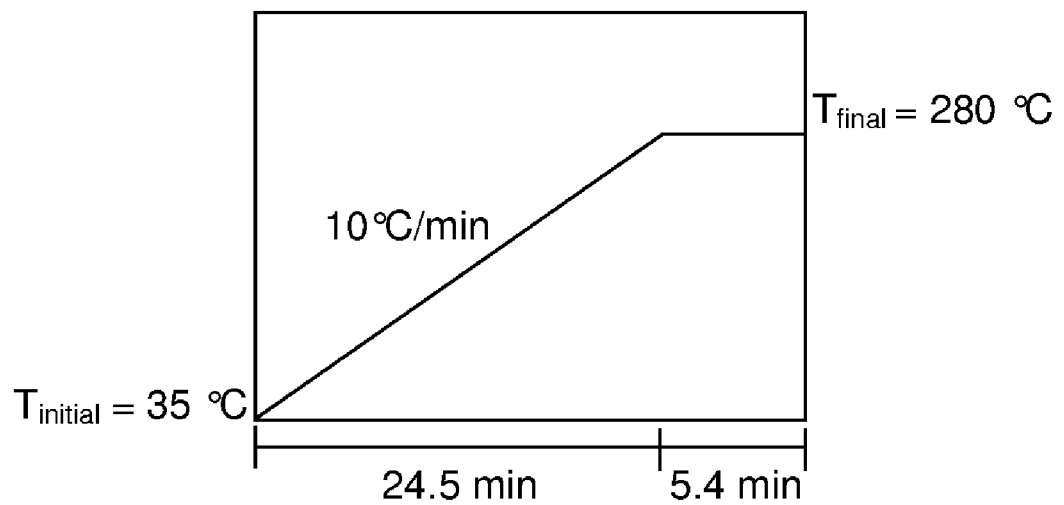
FIG. 8 shows the GC-FID temperature profile for liquid analysis.
Figure 9:
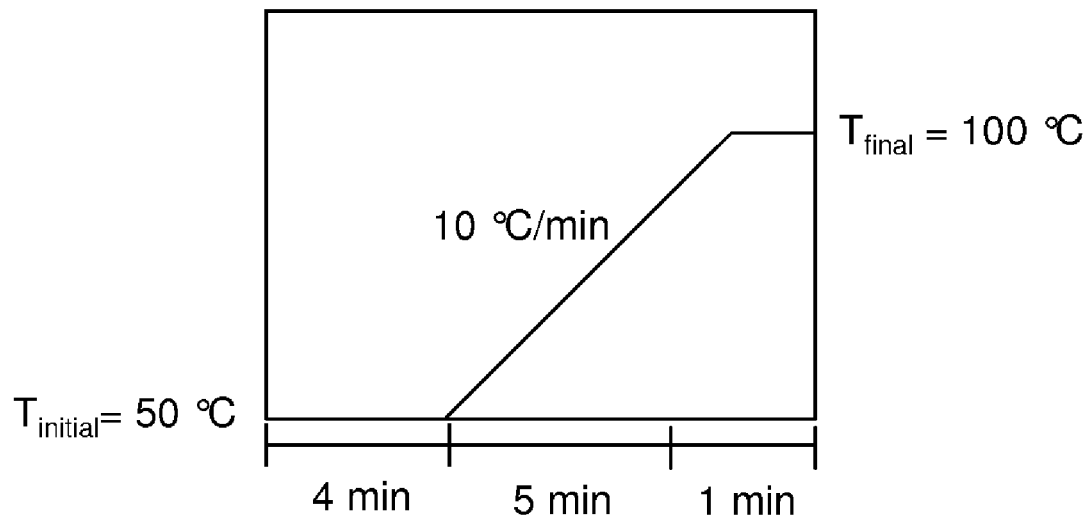
FIG. 9 shows the GC-TCD temperature profile for gas analysis.

The pentane extracts were analyzed on a Varian 3400 Gas Chromatograph equipped with a Varian 8200 auto-sampler (Palo Alto, Calif.) coupled with a flame-ionizing detector (FID) operated at 320° C. An RH1 column from Rose Scientific (Mississauga, Ontario, CA) was used for all analyses and the injection volume remained constant at 1 µl. The temperature profile is shown in FIG. 8. The initial column temperature was set at 35° C. and programmed to increase to 280° C. at a rate of 10° C./min. It was held at the final temperature for 5.4 minutes, for a total run time of 29.9 minutes.

Two external standards were run for product verification. These were (1) a $C_8$-$C_{20}$ alkane mixture (Fluka) and (2) a C3:0-C20:0 carboxylic acid mixture prepared in-house using carboxylic acids purchased from Sigma. These internal standards were run throughout the GC analysis to account for potential shifting of the peaks.

Gaseous Samples

To collect gas samples from the microreactor for analysis, a ¼ Swagelok® tube fitting with a septum was screwed into the fitting used to connect the microreactor to the purge system. A glass syringe and needle was inserted through the septum and the reactor valve was opened. Four ml of gas was drawn from the reactor using the syringe and expelled into a 5 ml vacutainer. This was repeated for a total of 8 ml of gas product in each 5 ml vacutainer. Gas fractions were analyzed on a Hewlett Packard Series II 5890 gas chromatograph coupled to a TCD (total composition detector) set at 80° C. 100 μL of the sample was manually injected onto a 30 m Agilent HP-plotq column with an I.D. of 0.53 μm. The temperature program used is shown in FIG. 8. Select gas samples were also run on GC-FID at the conditions outlined below.

Gas Chromatography-Mass Spectrometry (GC-MS)

Preliminary GC-MS analyses were conducted on select samples using a Waters (formerly Micromass, Milford, Mass.) Trio 2000 equipped with a HP5890 Series II GC in the University of Alberta's Chemistry Department. The temperature profile used was the same as shown in FIG. 8.

Extent of Reaction

To determine the extent of reaction it was necessary to dissolve all of the stearic acid feed remaining in the reactor. Chloroform was used as an extraction solvent because of the relatively high solubility of stearic acid in this solvent compared to pentane. Reaction products were washed out of the microreactors with chloroform into a round bottom flask until no product remained inside the reactor. The chloroform was then removed by roto-evaporation. During the evaporation/drying process, it is likely that some of the volatile products were lost, but because it is only the stearic acid that will be quantified, this should not affect the result. Thirty ml of chloroform spiked with internal standard was pipetted into the flask with the remaining products and swirled until all of the product had dissolved. Based on the solubility of stearic acid in chloroform, 30 ml is more than sufficient to dissolve the maximum possible stearic acid product (1 gram if no reaction occurred). Samples were taken and stored at 4° C. in dram vials with Teflon liners until analysis. Controls were conducted using the extraction procedure with no thermal treatment.

Derivatization with Diazomethane

A 250 μl aliquot of sample was added to a one dram vial and completely dried under $N_2$ before excess amounts of diazomethane, prepared in-house, was added to the vial. After the reaction was complete (i.e. no more bubble formation), the sample was dried again with $N_2$ and then resuspended with a known volume of chloroform before analysis on GC.

Percentage of Liquid and Gas Fractions

To get a crude estimate of the liquid yield, the reactor was opened and the liquid product was extracted with a Pasteur pipette and weighed. To get a crude estimate of the mass of the gas product, the reactor was weighted before and after venting the gas. For these reactions, 5.0 g of stearic acid were used as feed instead of the typical 1.0 g so that the difference could be readily measured.

Hydrolysis Reactions

Before the crude and vegetable oils were pyrolyzed, they were first hydrolyzed. Small-scale hydrolysis reactions were conducted in the same microreactors as the pyrolysis reactions. Approximately 3 grams of tallow or oil and 6 grams of distilled water were added to the microreactors for a 1:2 ratio (by weight) of oil/tallow to water. The reactors were sealed as described previously and pressurized with $N_2$ to 3.48 MPa (500 PSI). The hydrolysis reaction was conducted at 250° C. for 4 hours. When the reactors were opened, they were placed in a beaker of hot water so that the products remained in liquid state and were transferred to a glass sample vial with a Pasteur pipette. The fat layer was allowed to separate from the glycerol/water layer and was pipetted into a separate glass vial. Samples were stored at 4° C. until pyrolysis or derivatization. It was assumed that if any water remained in the sample, the rate of hydrolysis would be negligible at this low temperature. This fat or oil layer will herein be referred to as the oil or fat hydrolysates, so as not to confuse these products with the products formed after pyrolysis (i.e. the pyrolyzates or pyrolytic oil).

Fatty Acid Composition of the Feed

The fatty acid composition of the yellow grease tallow, bleached fancy tallow, poultry tallow, and canola oil was determined by derivatizing samples with boron-trifluoride and analyzing them on GC-FID. The derivatization procedure is outlined below and the GC analysis was the standard fatty acid protocol as described above.

Derivatization with Boron Trifluoride

For derivatization with boron trifluoride, approximately 30 mg of sample was weighed into a test tube and 5 mL of a 14% boron trifluoride-methanol/methanol/hexane mixture (35:45:20 V:V:V) was added. The tubes were tightly sealed and heated in boiling water for 45 minutes. After the tubes had cooled, 4 mL of water and 4 mL of hexane were added and the tube was shaken for 1-2 minutes. The layers were allowed to separate and the hexane layer was extracted with a Pasteur pipette and stored in a dram vial with Teflon liner at 4° C. until analysis.

Analysis of Hydrolysates Using TLC-FID

The composition of the hydrolysates was determined using thin layer chromatography coupled with an FID detector (TLC-FID). Samples were prepared for analysis by weighing approximately 0.03 g of the fatty hydrolysates into a screw cap vial and adding 5 ml of HPLC grade hexane. A specific volume of sample was spotted on silica gel Chromarods-SIII using a needle and syringe in 0.2 μL increments. The rods were then placed in a developing tank containing a mixture of hexane/diethyl ether/acetic acid (80:20:1 V:V:V) for 20 minutes and dried at 120° C. for 10 minutes. Lipid analysis was conducted using an Iatroscan TH-10 (IARON-Laboratories Inc., Tokyo, Japan) with a hydrogen pressure of 113 kPa, air flow rate of 2000 mL/min, and a scan speed of 30 s/rod. A reference standard containing 25% (w/w) each of oleic acid, monoolein, diolein and triolein was obtained from Nu-Chek Prep Inc. (Elysian, Minn.).

Analysis of Hydrolysates Using GC-FID

To determine the composition of unreacted or non-hydrolyzed feed, if any, GC-FID analysis was conducted using derivatized samples. Bleached fancy hydrolysates were derivatized by four different methods, which only methylate specific groups as outlined in Table 5. Diazomethane derivatization was conducted using the procedure outlined above.

The other three methods are discussed below.

Derivatization with Sodium Methoxide and Methanolic HCL

The same procedure was used for derivatization with sodium methoxide and methanolic HCL. A 10-30 mg oil or fat sample was weighed into the bottom of a test tube with 50 µL of benzene to solubilize the sample. The sample was allowed to sit for 20-30 minutes before 2 mL of either sodium methoxide or methanolic HCL was added to the test tube. The samples were then heated in a water bath (30 minutes for sodium methoxide, 50 minutes for methanolic HCL) at 50° C. The samples were allowed to cool before 100 µL of water and 2 mL of hexane were added to the test tubes. The tubes were shaken and allowed to sit while the organic and aqueous layers developed. The hexane (organic) layer was extracted and stored in a vial with a Teflon® liner at 4° C.

IV. Internal Reactor Temperature and Pressure for the Techne SBS-4 Sand Bath

Figure 10:
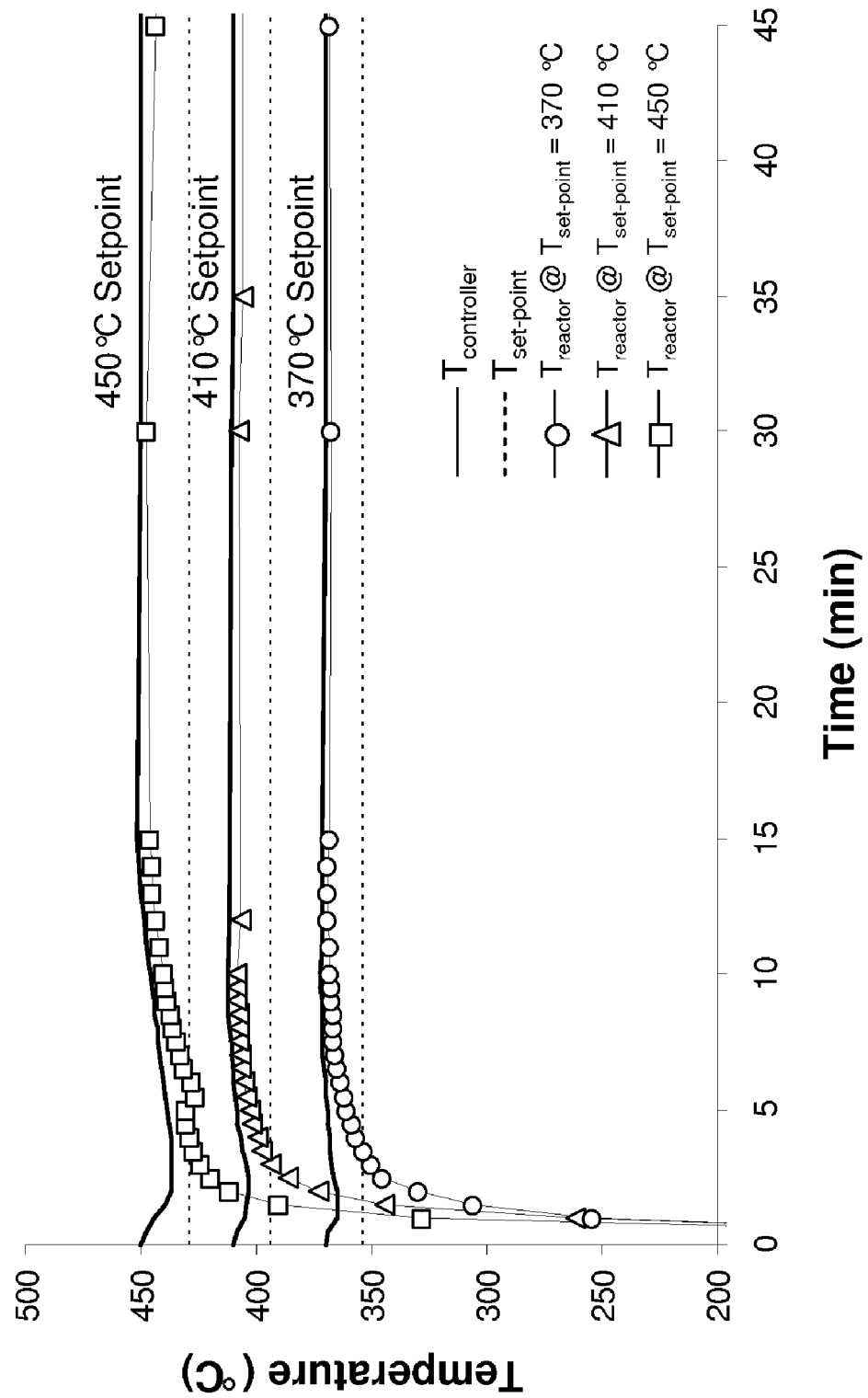
FIG. 10 shows the internal reactor temperature during stearic acid pyrolysis as a function of time for controller set-point temperatures of 370° C., 410° C., and 450° C., where the reactions were conducted in $N_2$ atmosphere and were initially at atmospheric pressure.

Temperature profiles representing heating of the microreactors at 370, 410, and 450° C. are presented in FIG. 10. The data represents the average between duplicate runs and the error bars (not visible) represent the standard error between these runs. The heating rate of the material inside the reactor appears to be fairly rapid as the reactor temperature, $T_{reactor}$, reaches 95% of the setpoint temperature (referenced from the starting temperature at time zero and shown on FIG. 10 as the dashed line) within 3.5, 3, and 4 minutes for the three setpoint temperatures, respectively. As expected, there is a drop in the controller temperature (solid line), at all three temperatures, after the reactors are dropped in the bath. At 370° C. it took approximately 6 minutes for the bath to heat back up to 370° C. while at 410° C. it took 5.5 minutes. It took between 12-14 minutes for the bath to heat back up to temperature during the runs conducted at 450° C.

The pressure gauge was checked throughout the reaction run, however the set-up made it difficult to read due to the agitation. At 370° C. one of the reaction runs resulted in no pressurization during the reaction but the second run resulted in a maximum pressure of 1,034 kPa (150 PSI). In both cases, the pressure gauge indicated zero pressure after quenching. At 450° C., the maximum pressure reached during separate runs was 2,586 kPa (375 PSI) and 3,103 kPa (450 PSI). After quenching, there was approximately 689 kPa (100 PSI) of pressure in the reactors. At 410° C., one of the runs exhibited an extremely large pressure increase at the end of the run to 4482 kPa (650 PSI). After quenching, the pressure inside the reactor was 689 kPa (100 PSI). Based on the results of the other runs, this appears to be unusual. The second run at 410° C. yielded results that would be expected based on the other temperatures. A maximum pressure of 1379 kPa (200 PSI) was reached but after quenching, the gauge indicated zero pressure inside the reactor.

V. Model Compound Work

Preliminary Pyrolysis Studies

The experimental set-up for the preliminary pyrolysis reactions is shown in Table 6. All reactions were conducted in nitrogen and were initially at atmospheric pressure. Immediately after quenching, the reactor was opened and 10 ml of pentane was added to the products, swirled, and the pentane soluble products were extracted with a pipette into a flask. Two subsequent 10 ml extractions were also conducted for a total of 3×10 ml extractions before an aliquot was transferred to a sample vial with a Teflon® lined screw cap. For this set of runs, no internal standard was added but unreacted stearic acid was analyzed as a control. The liquid extracts were analyzed on GC-FID. The results are shown in FIGS. 4.2 and 4.3. Duplicate chromatograms (not shown) are very similar for all the temperatures, indicating good consistency between reaction runs.

Figure 11:
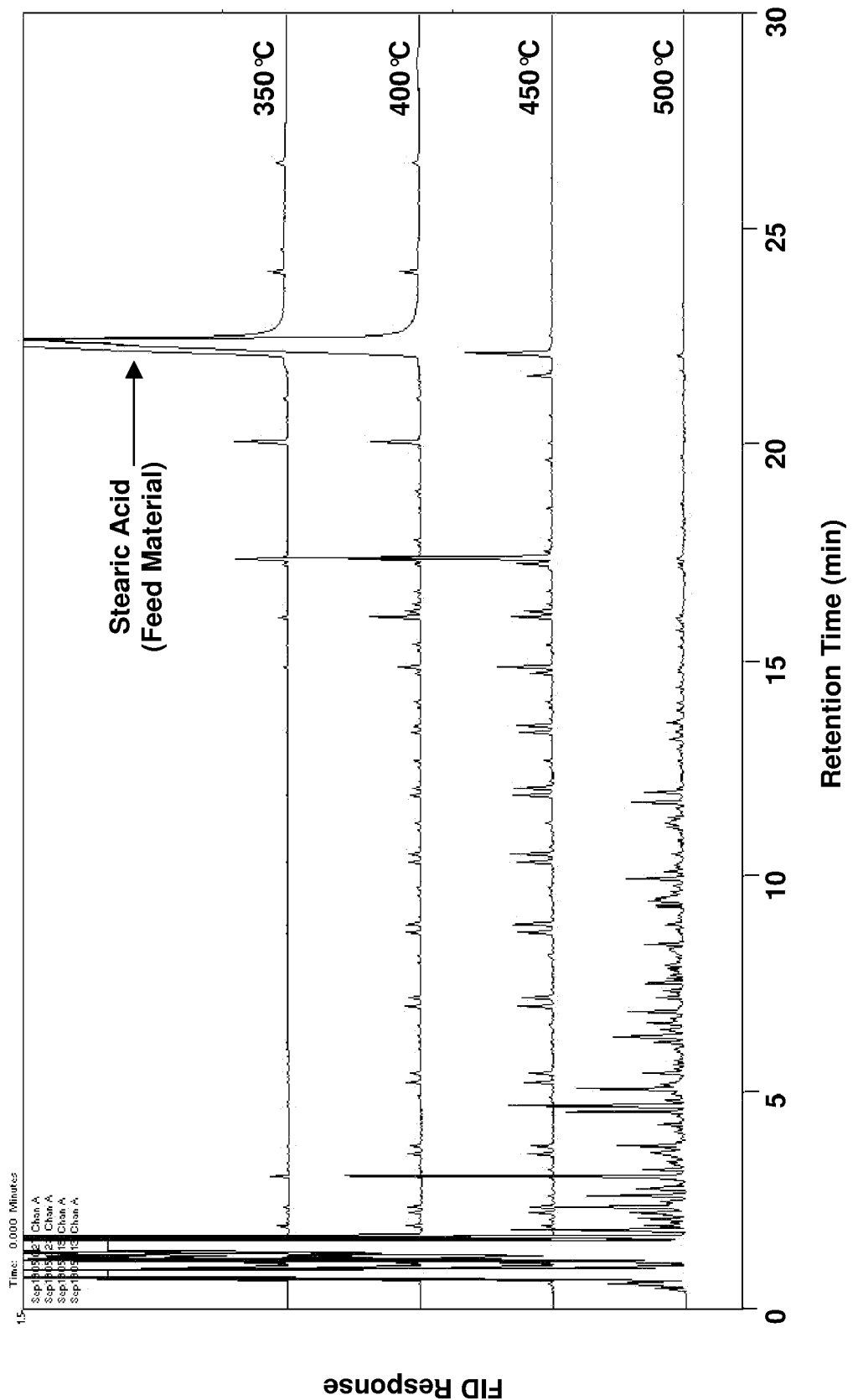
FIG. 11 shows the GC-FID chromatogram of the pentane soluble pyrolysis products of stearic acid after 30-minute reaction times at temperatures between 350° C. and 500° C., where the reactions were conducted in $N_2$ atmosphere and were initially at atmospheric pressure.
Figure 12:
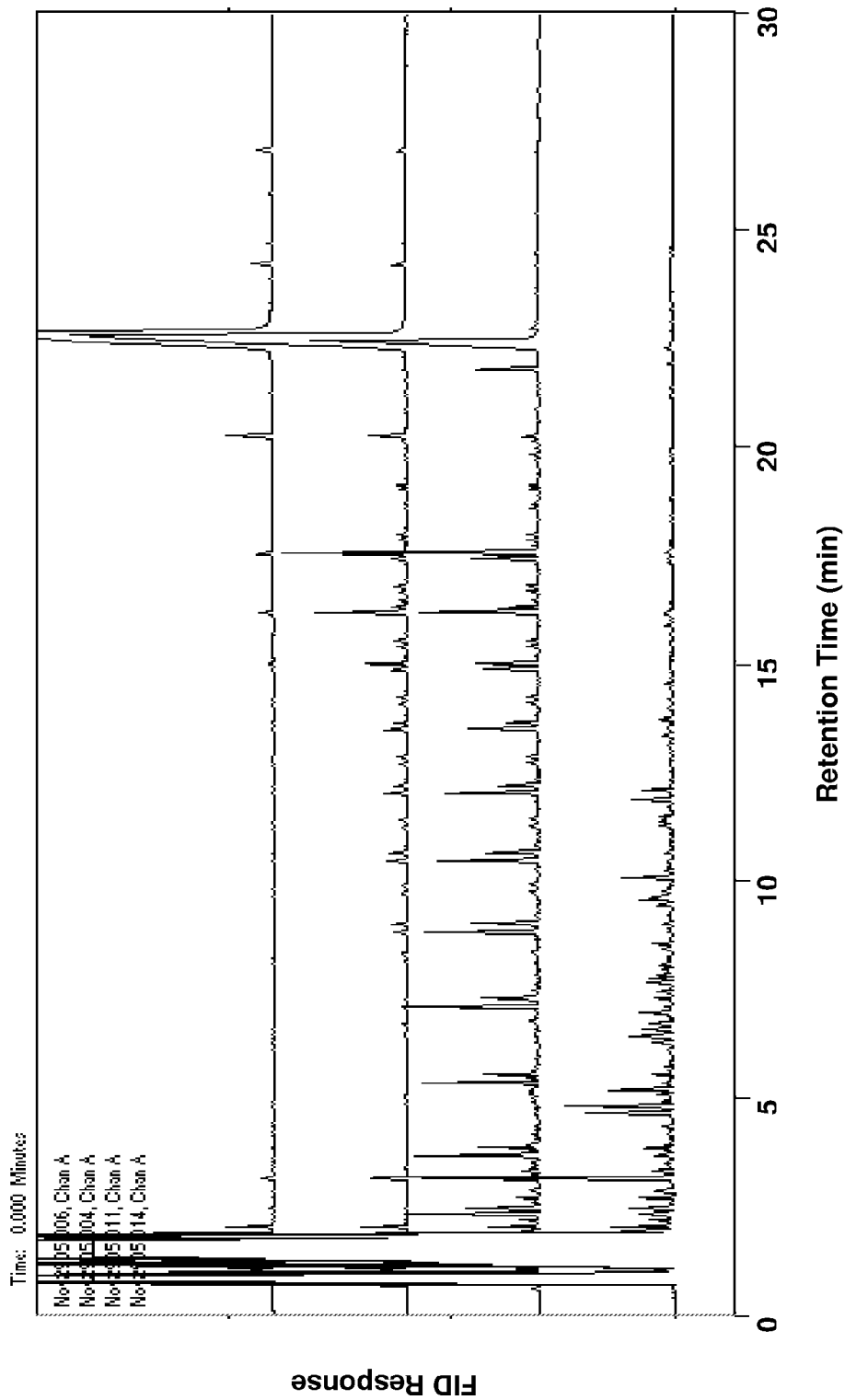
FIG. 12 shows the GC-FID chromatogram of the pentane soluble pyrolysis products of stearic acid after 5-minute reaction times at temperatures between 400° C. and 550° C., where the reactions were conducted in $N_2$ atmosphere and were initially at atmospheric pressure.

FIGS. 11 and 12 show that product distribution changes substantially with temperature and time. A 30-minute reaction at 350° C. (FIG. 11), results in little reaction as indicated by the absence of peaks in comparison to the other runs and the relatively large peak that was identified as the starting material, stearic acid. This was determined by comparing retention times of a sample of stearic acid in pentane with no thermal treatment. At 400° C., a distinct series of ladders begins to form and at 450° C., these ladder series continue to develop. At 500° C., these ladders begin to degenerate resulting in numerous peaks cluttered at low retention times. The same trend is evident for the 5 minute reactions but at slightly higher temperatures. At 400° C. (FIG. 12) the ladders are just starting to develop and increase in size at both 450° C. and 500° C. Although the ladders are still present at 500° C., more peaks are starting to form at retention times less than 5 minutes. At 550° C., these ladders have completely degenerated and result in a similar looking distribution as the 30-minute reaction at 500° C.

Identification of Peaks

GC/MS Analysis

Figure 13:
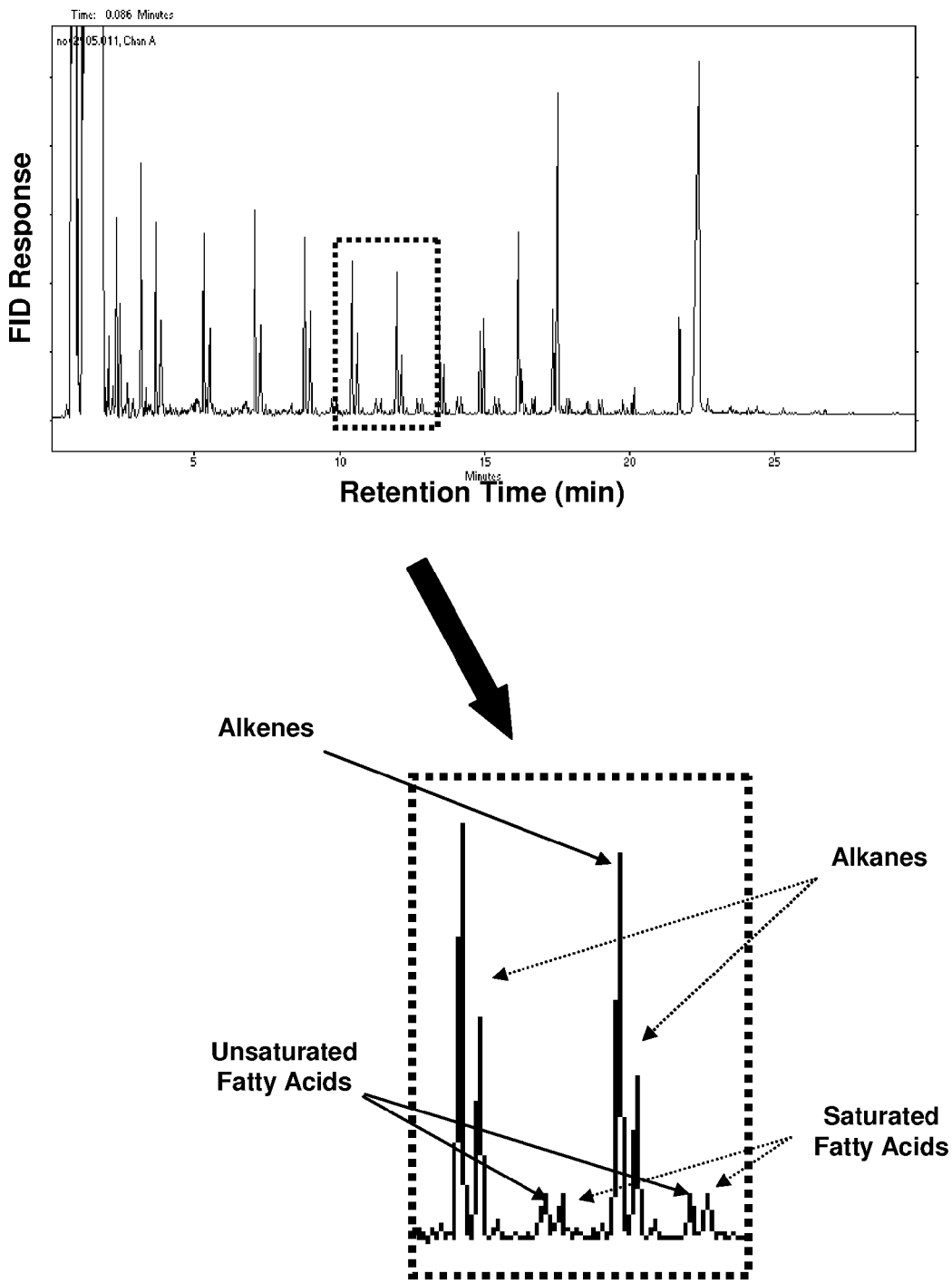
FIG. 13 shows the identification of the typical ladder series formed after heating stearic acid for 5 minutes at 500° (chromatogram in FIG. 12), where the reaction was conducted in $N_2$ atmosphere and was initially at atmospheric pressure.

The following samples were analyzed by mass spectrometry: (1) stearic acid breakdown products after a 5-minute reaction at 500° C. (chromatogram shown in FIG. 12) and (2) stearic acid breakdown products after a five minute reaction at 550° C. (chromatogram shown in FIG. 12). A search was conducted using the NIST (National Institute of Standards and Technology) mass spectra library and the best spectra matches were determined. The results show that after five minutes at 500° C., four series or ladders were formed including an alkane series, an alkene series, a carboxylic acid series, and an unsaturated carboxylic acid series with one double bond. The spectra indicate that it is likely that the double bond in the alkenes is at the one position and in the unsaturated carboxylic acids, is at the end position opposite the carboxyl group, however, this was not confirmed by NMR (nuclear magnetic resonance). These ladders are illustrated in FIG. 13. The results of the NIST search at 550° C. indicated that many of the compounds were likely aromatic.

Product Verification Using External Standards on GC-FID

Figure 14:
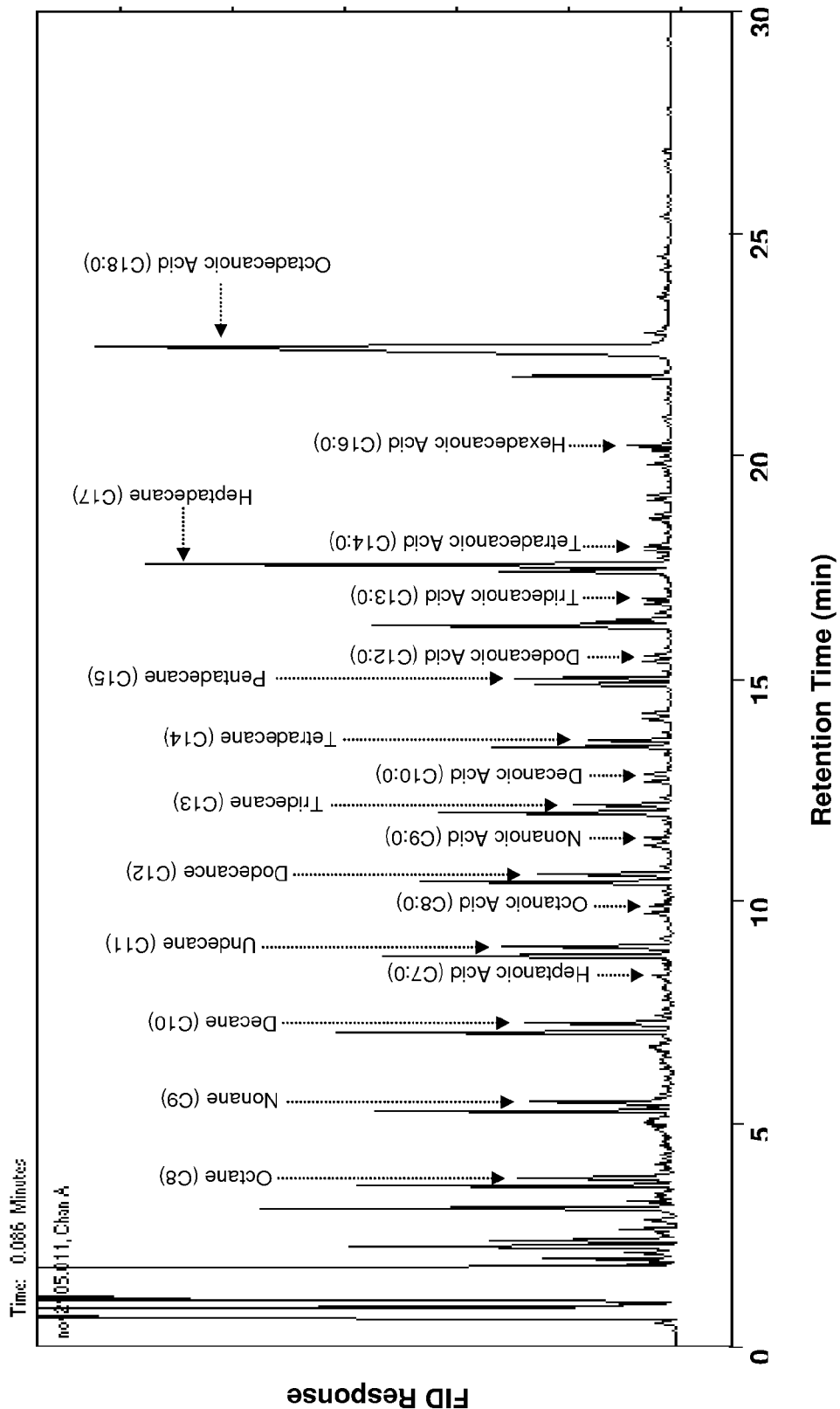
FIG. 14 shows the typical pentane soluble pyrolysis products of stearic acid after 5 minutes at 500° verified by running external standards, where the reaction was conducted in $N_2$ atmosphere and was initially at atmospheric pressure.
Figure 15:
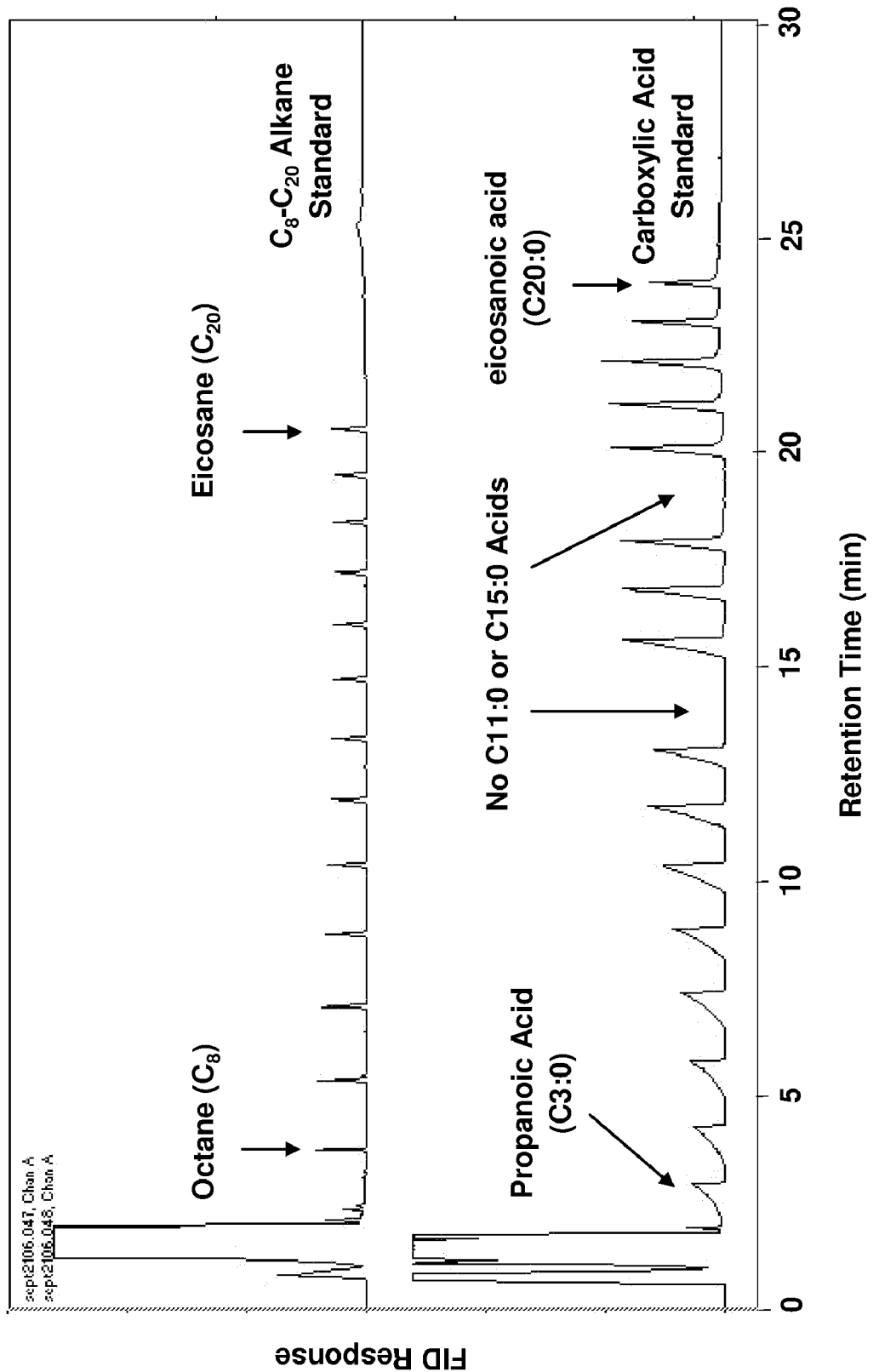
FIG. 15 is a GC-FID chromatogram showing the external standards run for verification of pyrolysis products, where the standards were (1) a $C_8$-$C_{20}$ alkane mixture purchased and (2) a carboxylic acid standard.

FIG. 14 shows a chromatogram of the breakdown products of stearic acid after a 5-minute reaction at 500° C. The compounds labeled were verified using external standards coupled with the results from the GC/MS. Two external standards including (1) a mixture of $C_8$-$C_{20}$ alkanes purchased from Fluka and (2) a mixture of carboxylic acids prepared in-house using carboxylic acids from Sigma, were run on GC-FID using identical conditions. The resulting chromatogram is shown in FIG. 15. A series of alkanes from octane ($C_8$) to heptadecane ($C_{17}$) as well as a series of carboxylic acids between C7:0 (heptanoic acid) and C18:0 (stearic acid) were identified in the pyrolysis mixture.

Pyrolysis with a Second Extraction Using Toluene

Figure 16:
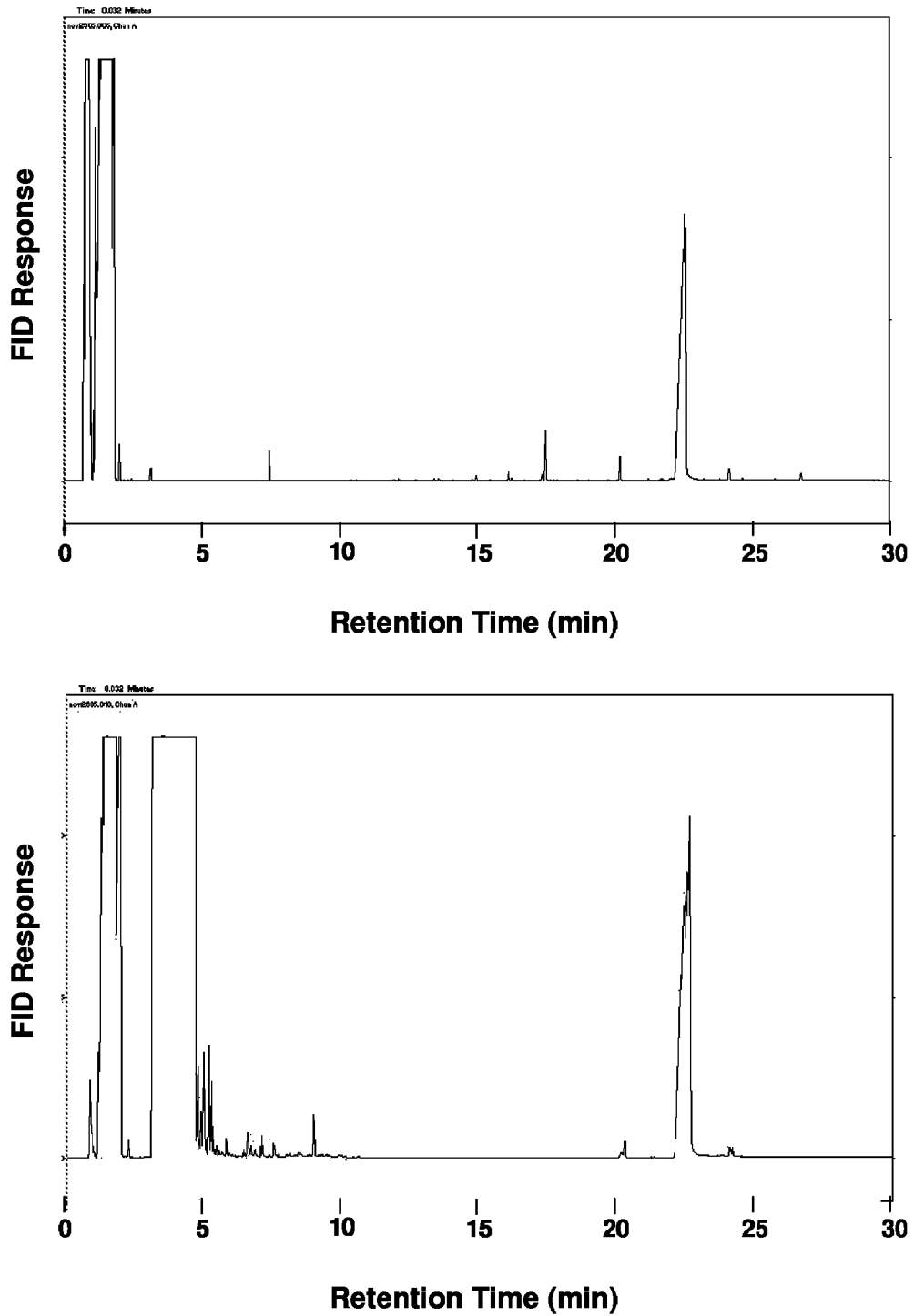
FIG. 16 is a GC-FID chromatogram showing pyrolysis products at 400° C. for 5 minutes in pentane (first extraction) and toluene (second extraction), where the reactions were conducted in $N_2$ atmosphere and were initially at atmospheric pressure.
Figure 17:
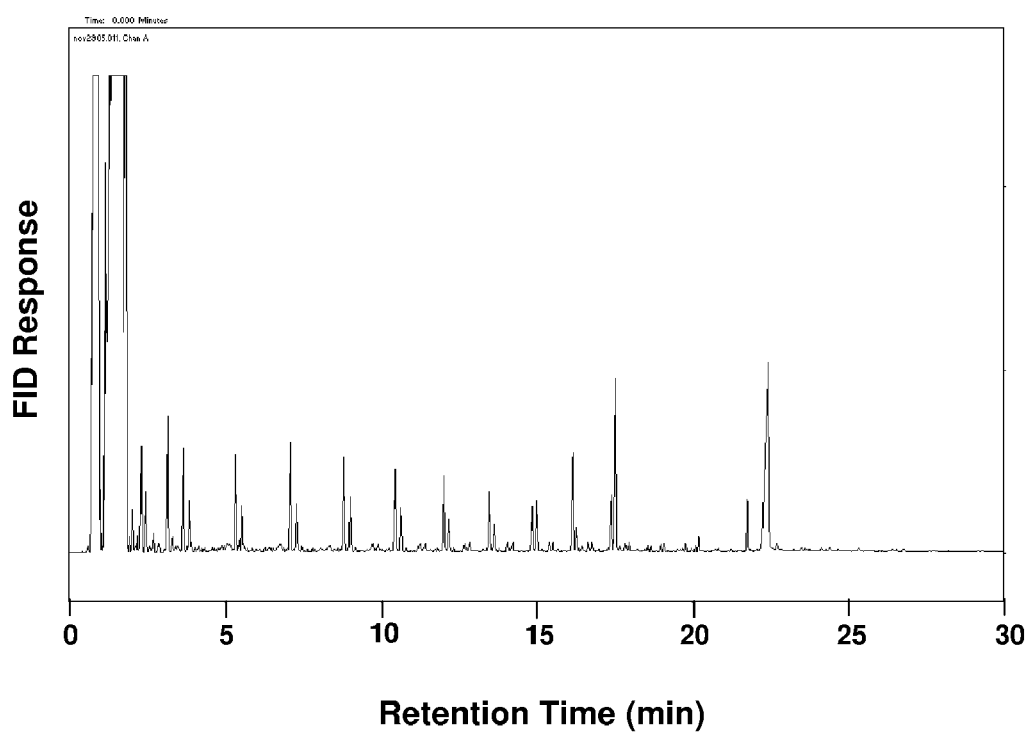
FIG. 17 is a GC-FID chromatogram showing pyrolysis products at 450° C. for 5 minutes in pentane (first extraction) and toluene (second extraction), where the reactions were conducted in $N_2$ atmosphere and were initially at atmospheric pressure.
Figure 17:
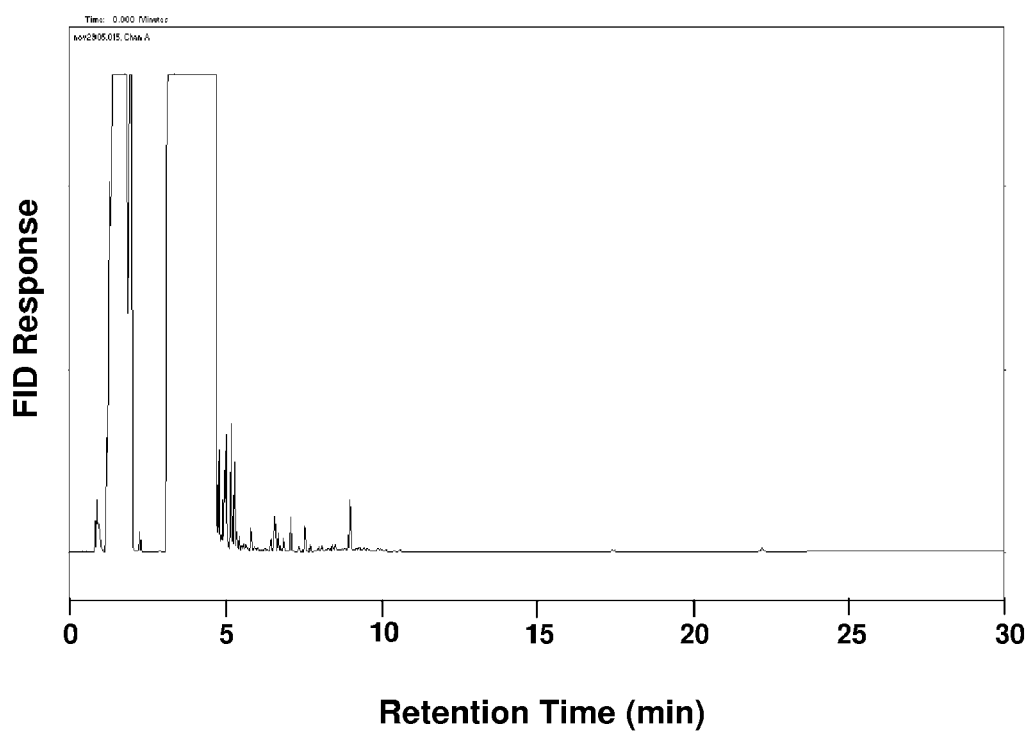

After the pentane extraction, there was still some material in the reactor. It is possible that this material is not soluble in pentane or that the solubility limit of the pentane had been reached. In other words, it was saturated with product and unable to dissolve anything more. Stearic acid is only somewhat soluble in pentane so it is possible that unreacted feed was also present in the reactor after the pentane extraction. In order to determine what types of products were still in the microreactor after the pentane extraction, a subsequent 3×10 ml toluene extraction was conducted for the 5-minute runs and collected for analysis. Select chromatograms are presented in FIGS. 16 and 17. FIG. 16 shows that the toluene extract contains only the starting stearic acid compound. The smaller peaks on either side of the largest peaks are impurities in the feedstock material (determined by running controls with no thermal treatment) and the peaks at retention times less than 10 minutes are impurities in the toluene (determined by running toluene through the GC). The reactor appeared to be empty after the toluene extraction indicating that the pentane dissolved all of the reaction products except for some of the uncreated acid feed. The results are similar at 450° C. (chromatograms not shown). At 500° C., more product was produced and there is less unreacted feed. At these conditions, the pentane dissolved the majority of the reactor products including all of the unreacted feed as shown by the absence of any compounds in the toluene fraction.

Effect of Drying Down Samples on the Product Profile

Figure 18:
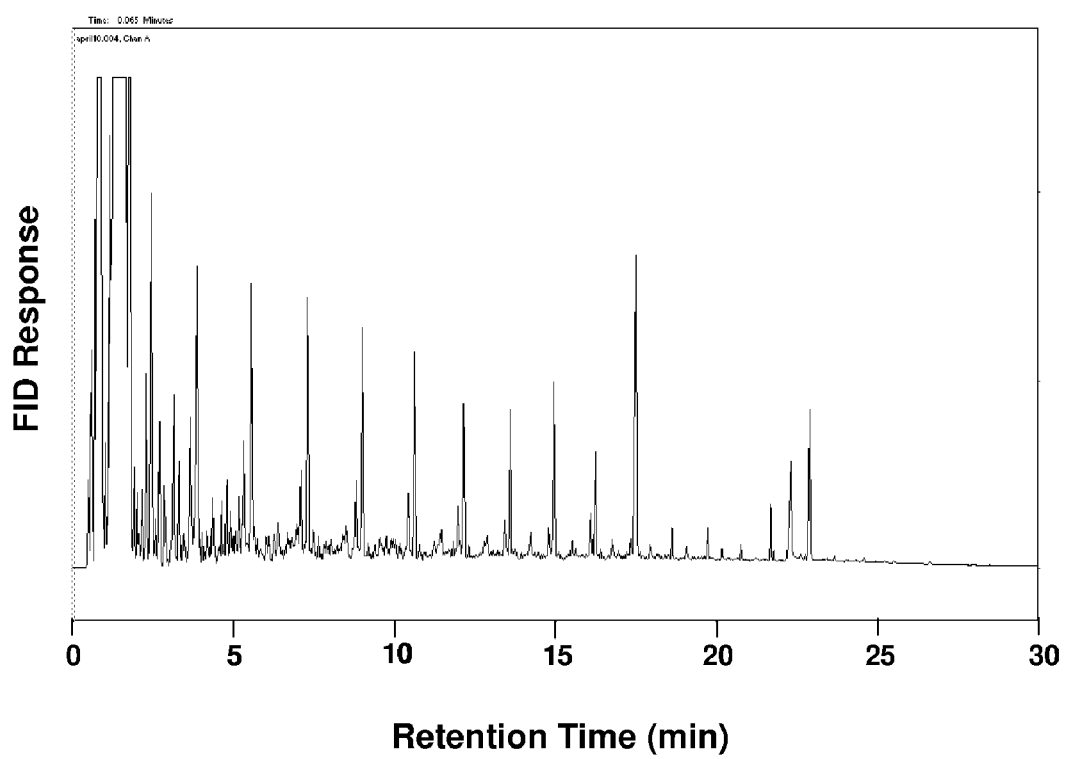
FIG. 18 is a GC-FID chromatogram showing the difference in product distributions before (a) and after drying and re-suspension (b) of stearic acid pyrolysis products for 1 hr reactions conducted at 450° C., where the reactions were conducted in $N_2$ atmosphere and were initially at atmospheric pressure.
Figure 18:
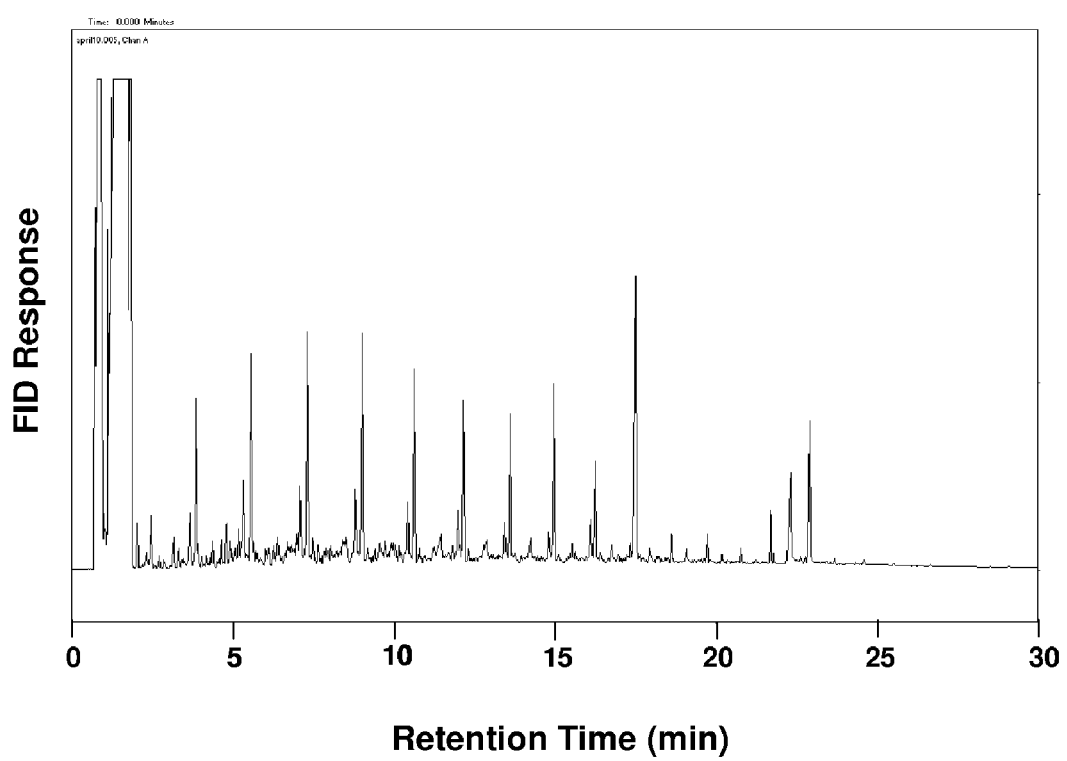

For mass balance and quantification, the weight of the pentane soluble product is most easily determined by drying down the sample under nitrogen gas and then weighing. The problem with this method is that many of the reaction products are volatile and have the potential to be evaporated during the dying process. Before developing extraction methodologies, it was of interest to determine if drying under nitrogen affected the product profile. Duplicate reactions were conducted for one hour at 450° C. and 500° C. The reactors were purged with nitrogen gas and were initially at atmospheric pressure. Ten ml of pentane was used to extract the reaction products and two 4 ml aliquots were transferred into sample vials. One of the samples was analyzed as-is while the other sample was dried down with nitrogen and then re-suspended with 4 ml of pentane before analysis. FIG. 18 shows chromatograms before and after drying at 450° C. The quantities and distribution of products changes substantially with drying, especially the lower retention compounds. At 500° C., where the products are mostly light ends and possibly aromatics, the drying process evaporates the majority of the compounds.

Pyrolysis at Different Times and Temperatures

Numerous reactions were conducted at various temperatures and times. These were conducted to see time and temperature effects on the pyrolysis products at a broader range of conditions as well as to modify the extraction procedure. A variety of runs were conducted at temperatures between 350-500° C. and times ranging from 1 to 6 hours. Results from these experiments helped select the conditions used for a larger time/temperature experiment.

Effects of Time and Temperature on Pyrolysis Products of Stearic Acid

Based on the results from the preliminary experiments, it was of interest to study the pyrolysis products of stearic acid over a wider range of temperatures and times to determine within which of these conditions the products of interest are formed. In this experiment, reactions were conducted at temperatures between 350-500° C. and times ranging from 0.5-8 hours. The times and temperatures chosen for this study were based on preliminary results and are outlined in Table 7. The conditions range from mild, where very little reaction took place to more severe where there is a substantial product breakdown and where the ladder series discussed in previous sections have degenerated. It is within these conditions that the products of interest are formed. All reactions were conducted in nitrogen atmosphere and the microreactors were initially at atmospheric pressure.

Product Distributions at Different Times and Temperatures

Figure 19:
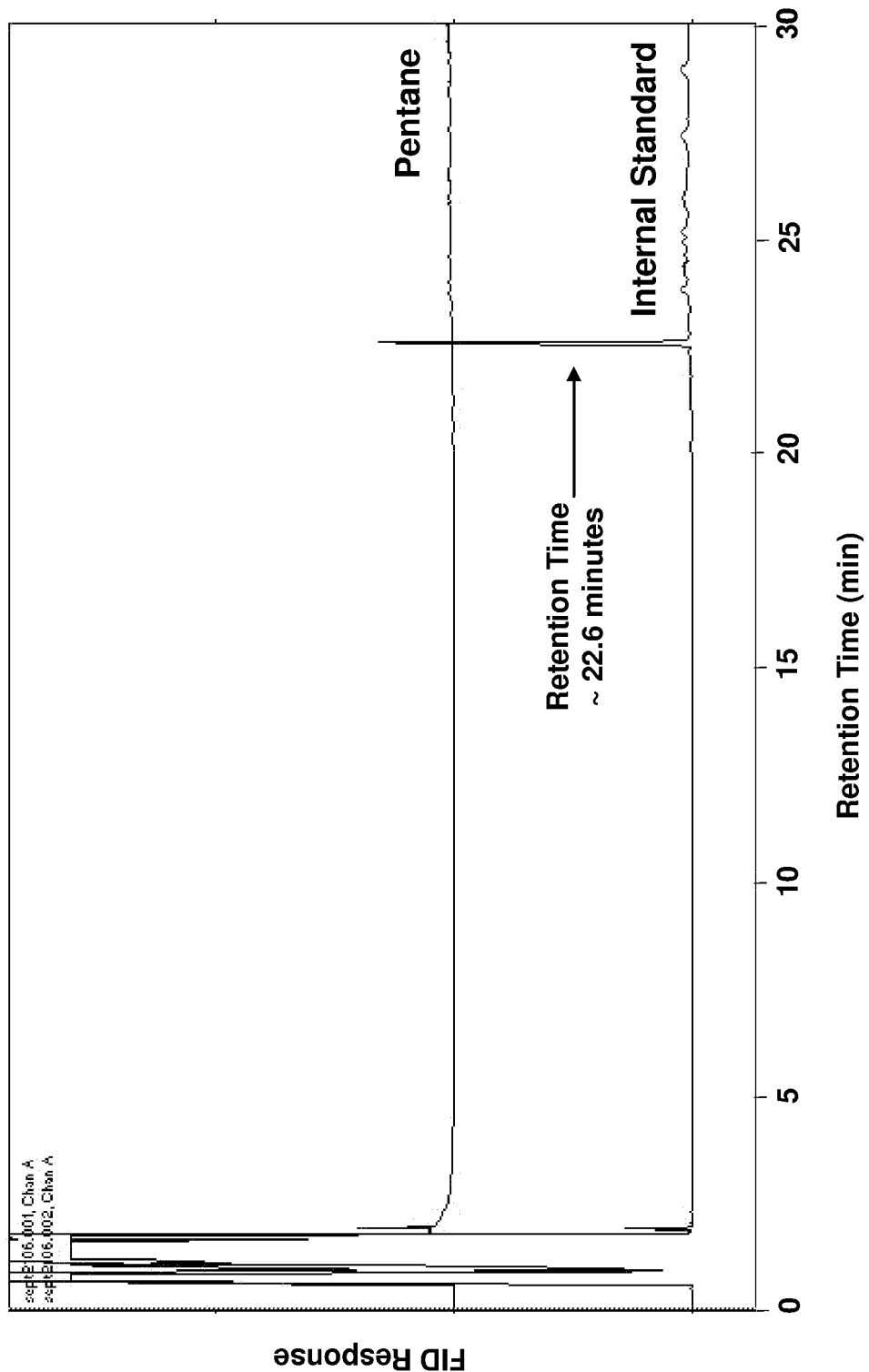
FIG. 19 is a GC-FID chromatogram showing the extraction solvent, pentane, and internal standard solution (nonadecanoic acid methyl ester in pentane).
Figure 20:
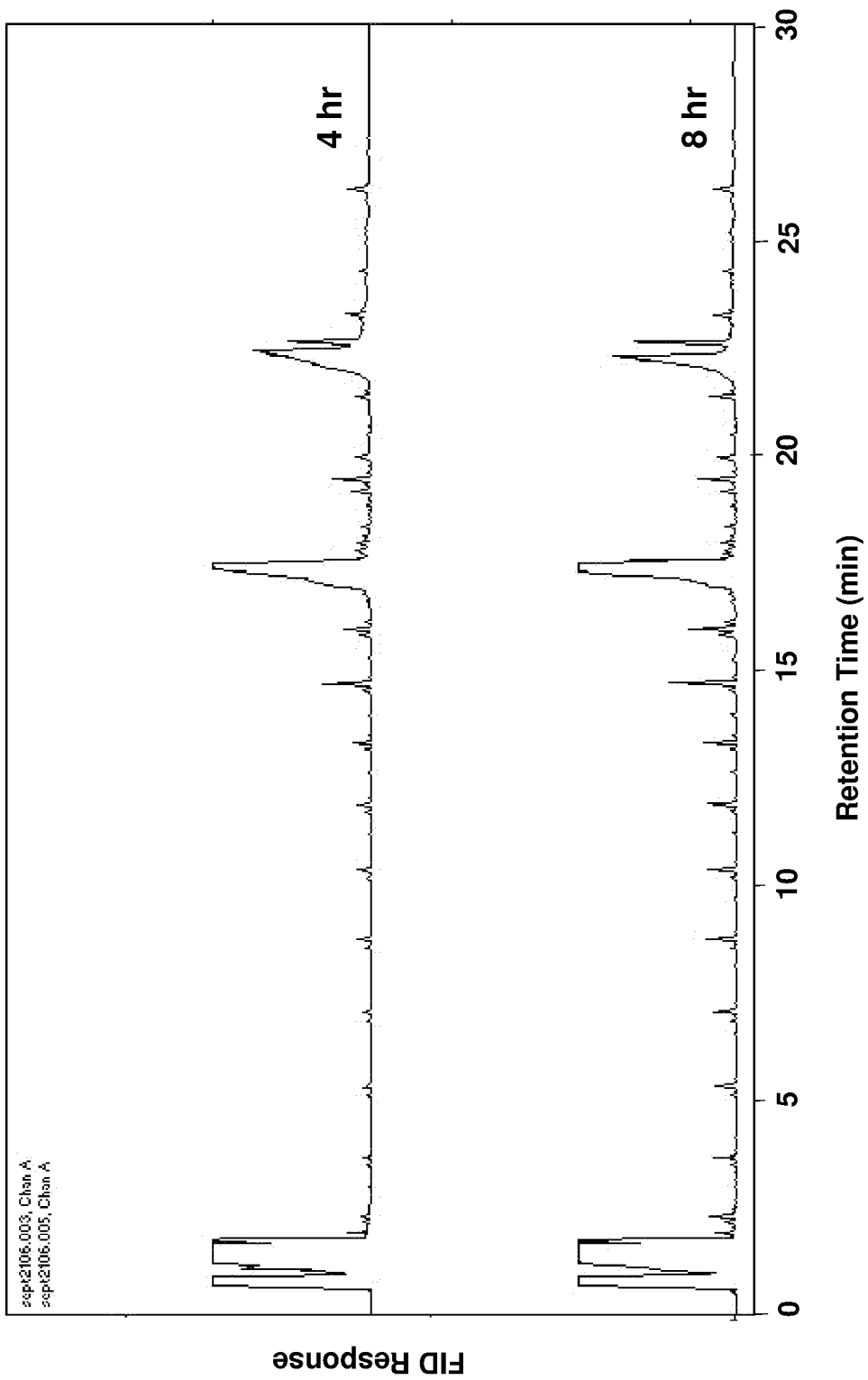
FIG. 20 is a GC-FID chromatogram showing pentane soluble stearic acid pyrolysis products from a batch reaction at T=350° C. and t=4 and 8 hours, where the reactions were conducted in $N_2$ atmosphere and were initially at atmospheric pressure.
Figure 21:
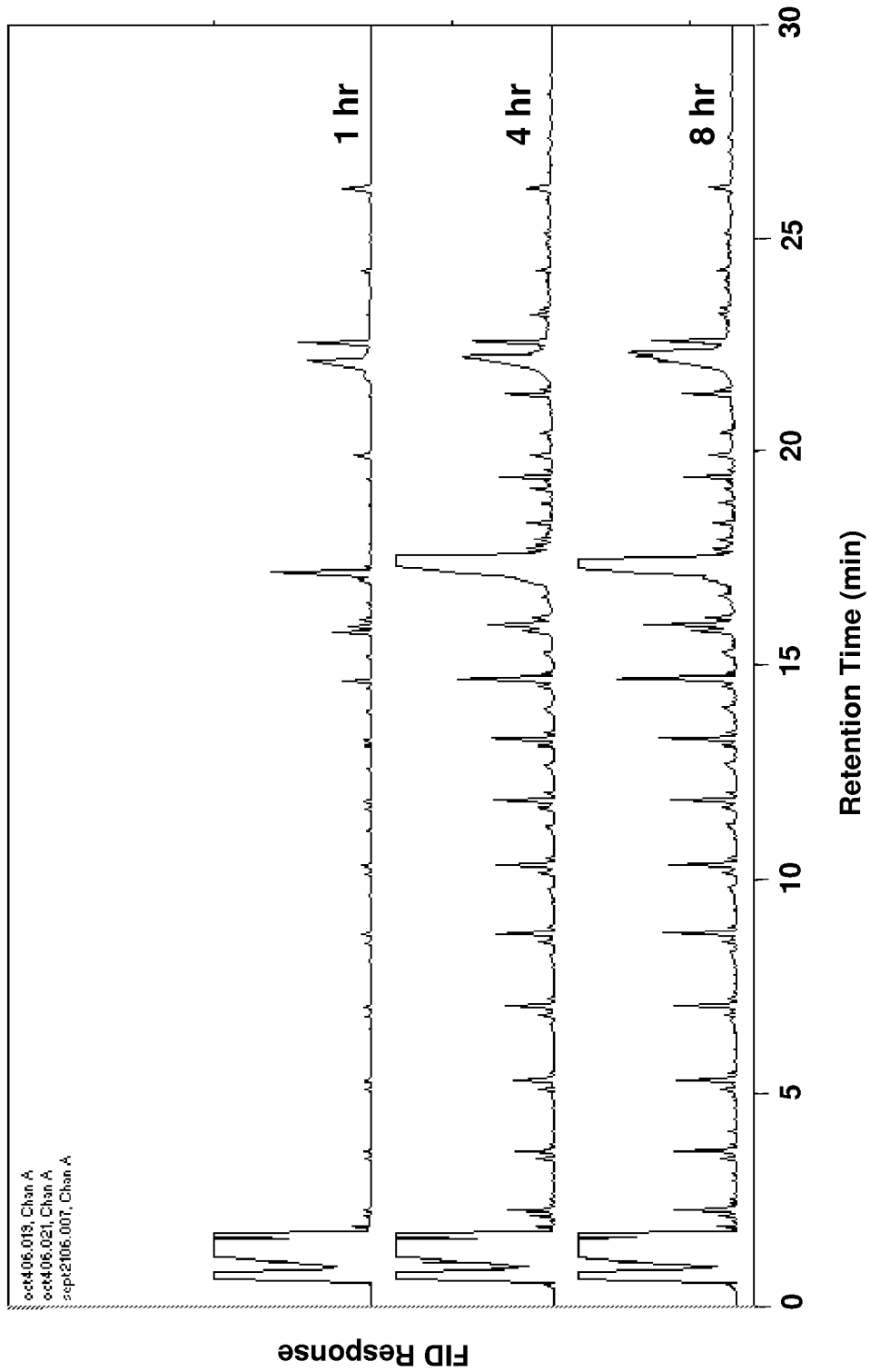
FIG. 21 is a GC-FID chromatogram showing pentane soluble stearic acid pyrolysis products from a batch reaction at T=370° C. and t=1-8 hours, where the reactions were conducted in $N_2$ atmosphere and were initially at atmospheric pressure.
Figure 22:
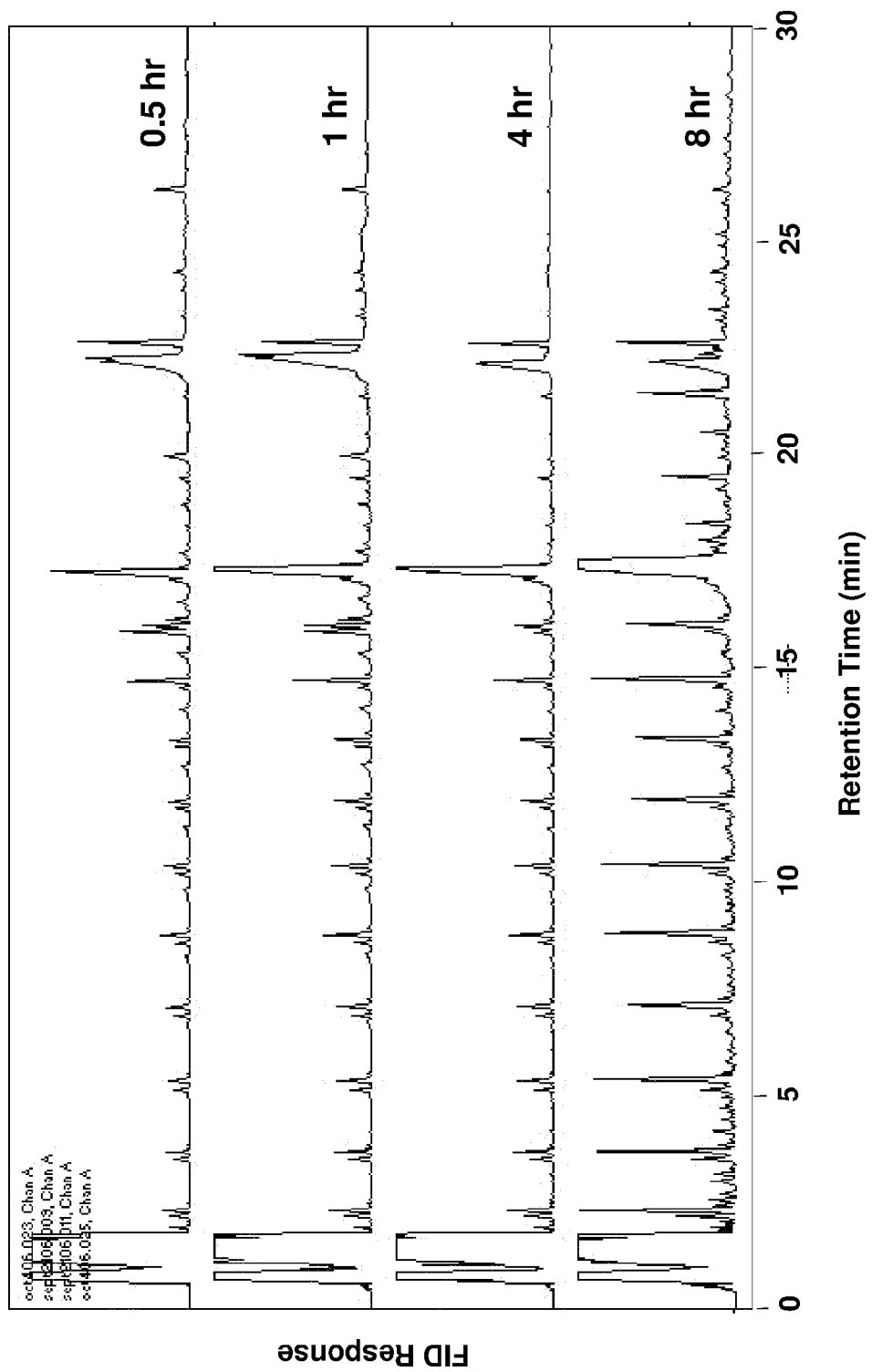
FIG. 22 is a GC-FID chromatogram showing pentane soluble stearic acid pyrolysis products from a batch reaction at T=390° C. and t=0.5-8 hours, where the reactions were conducted in $N_2$ atmosphere and were initially at atmospheric pressure.
Figure 23:
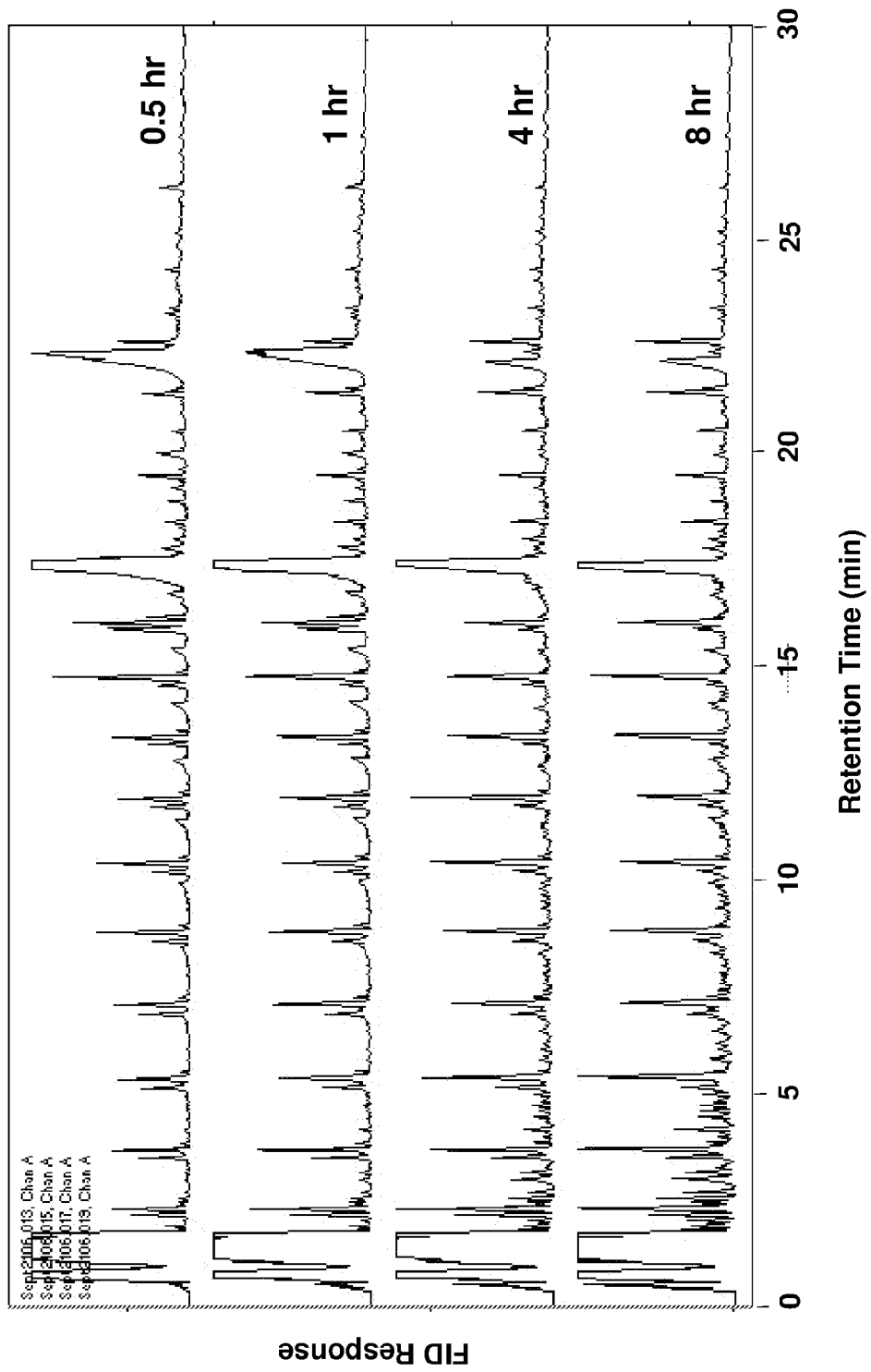
FIG. 23 is a GC-FID chromatogram showing pentane soluble stearic acid pyrolysis products from a batch reaction at T=410° C. and t=0.5-8 hours, where the reactions were conducted in $N_2$ atmosphere and were initially at atmospheric pressure.
Figure 24:
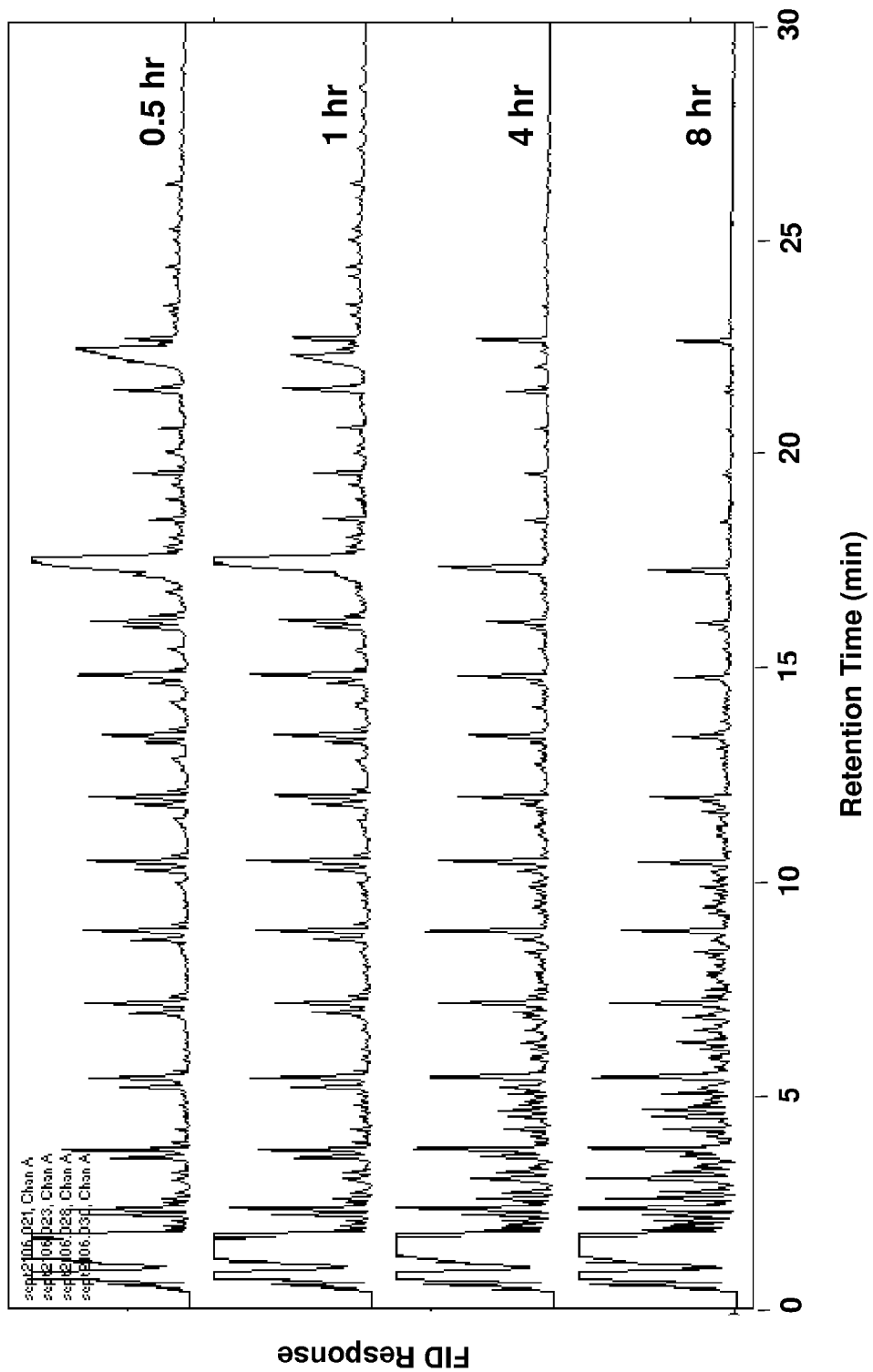
FIG. 24 is a GC-FID chromatogram showing pentane soluble stearic acid pyrolysis products from a batch reaction at T=430° C. and t=0.5-8 hours, where the reactions were conducted in $N_2$ atmosphere and were initially at atmospheric pressure.
Figure 25:
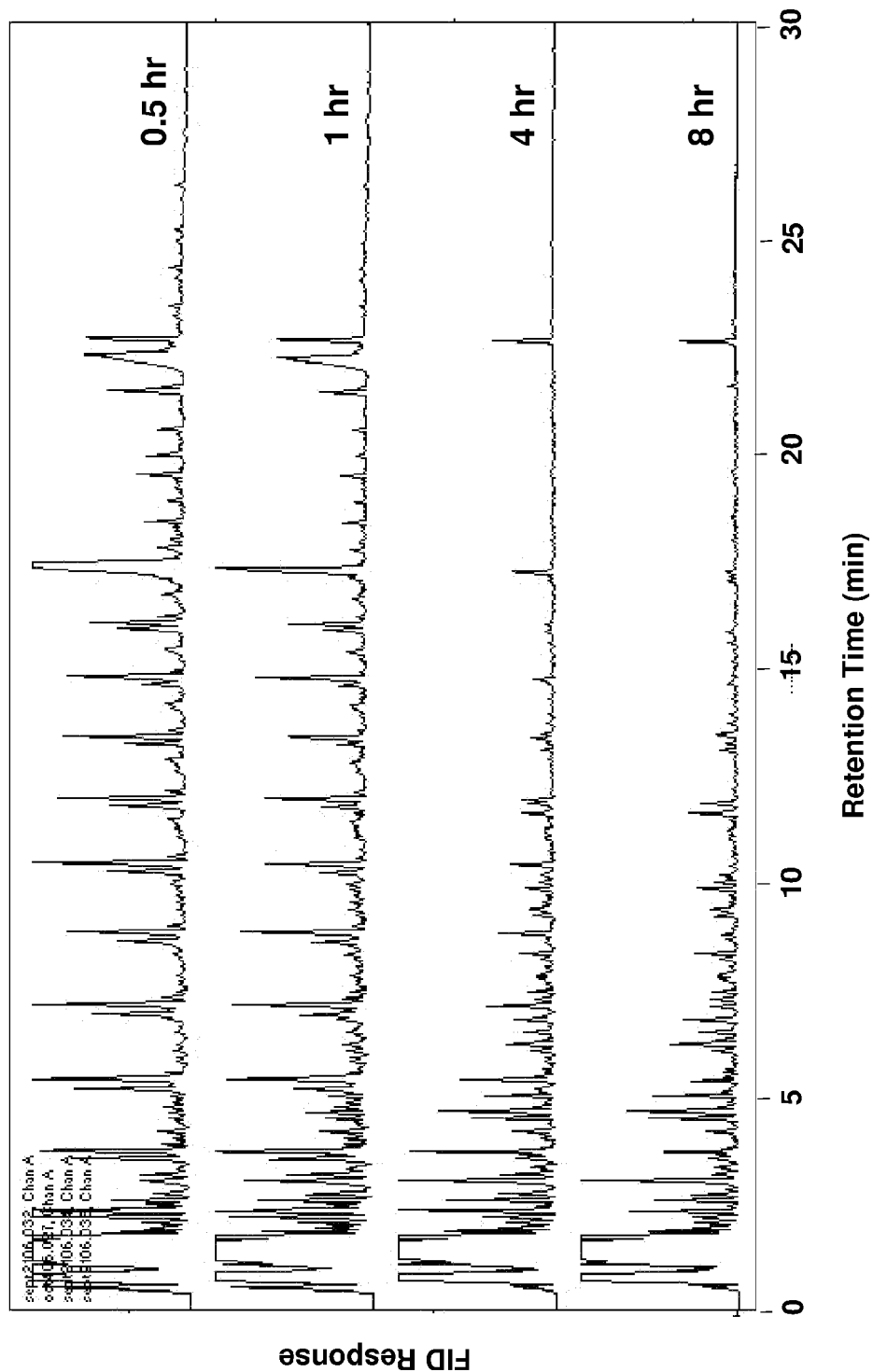
FIG. 25 is a GC-FID chromatogram showing pentane soluble stearic acid pyrolysis products from a batch reaction at T=450° C. and t=0.5-8 hours, where the reactions were conducted in $N_2$ atmosphere and were initially at atmospheric pressure.
Figure 26:
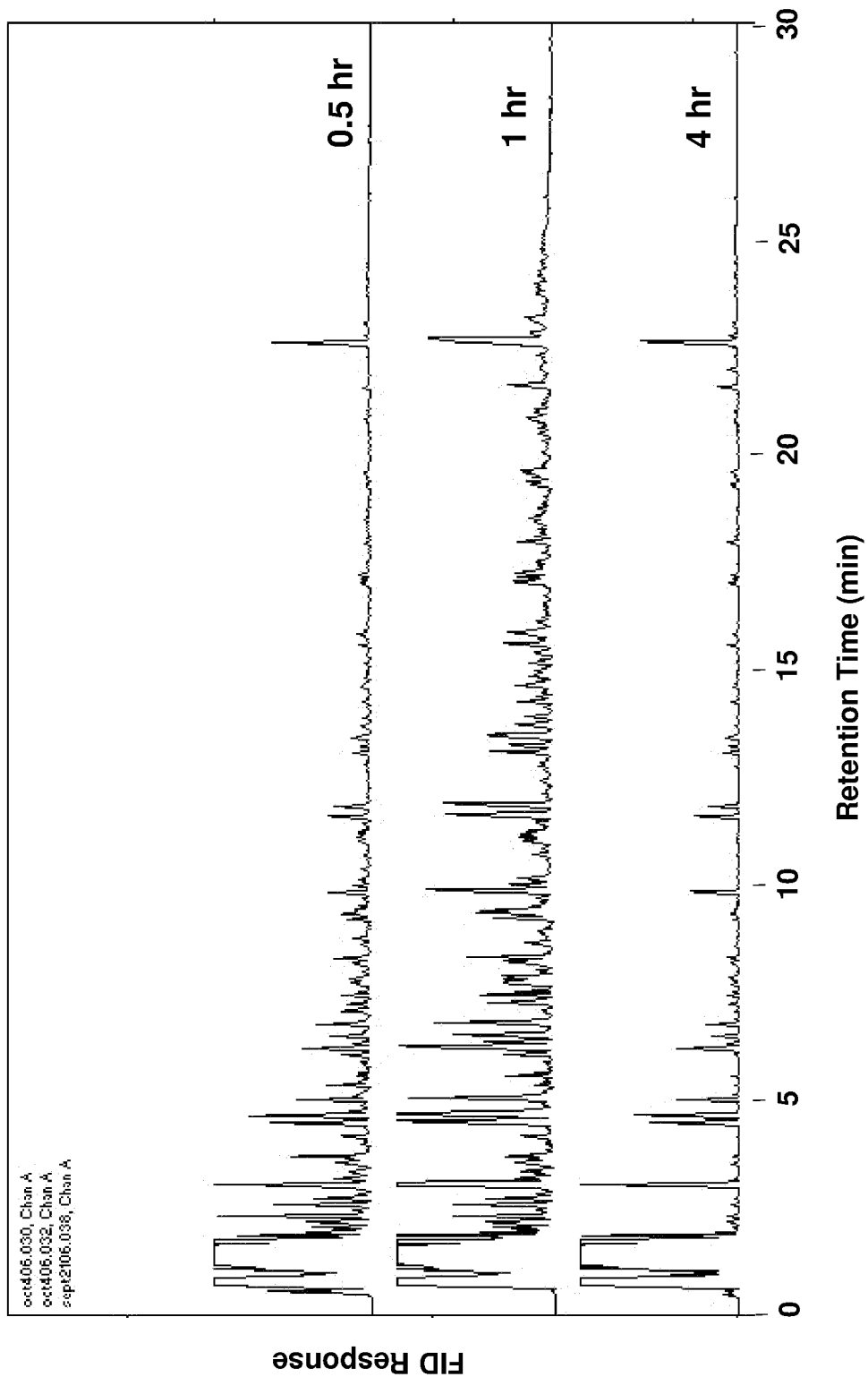
FIG. 26 is a GC-FID chromatogram showing pentane soluble stearic acid pyrolysis products from a batch reaction at T=500° C. and t=0.5-4 hours, where the reactions were conducted in $N_2$ atmosphere and were initially at atmospheric pressure.

For these reactions, nonadecanoic acid methyl ester was added as an internal standard at known concentrations. At the GC conditions used in this experiment, the nonadecanoic acid methyl ester elutes from the column at approximately 22.6 minutes as shown in FIG. 19. FIGS. 20-26 show the chromatograms from the reactions conducted at the conditions outlined in Table 7. These chromatograms give a good "snapshot profile" of the product distribution at various conditions. Due to the nature of the extraction solvent and the extraction method, it is possible that not all of the stearic acid, which is not very soluble in pentane, and heptadecane ($C_{17}$ alkane), which is solid at room temperature, was dissolved in the pentane. It is likely that these peaks are underestimated. In terms of the types of products formed at the various conditions, duplicate chromatograms (not shown) were virtually identical. The results from this experiment confirm previous results. Both time and temperature are shown to have a substantial effect on the product distribution. At 350° C. (FIG. 20), the main product is heptadecane ($C_{17}$ alkane). The alkane ladders are just starting to form at 4 hours and are slightly more developed at 8 hours. There is also some starting feed material remaining, however, the actual quantity cannot be estimated from the size of the peak area as explained previously. Analysis of the amount of unreacted feed at different conditions is discussed in later sections. As temperature and time increase, the development of the ladder series is evident. At 390° C. and 8 hours, 410° C. and 1, 4, and 8 hours, and 430° C. at 0.5 and 1 hour, these ladders appear to be the most developed. At 430° C., there is evidence of low retention compounds, possibly aromatics, starting to develop. At 450° C. after 4 hours and at 500° C., the ladder series have degenerated.

Estimation of $C_8$-$C_{20}$ Alkanes and Alkenes

Figure 27:
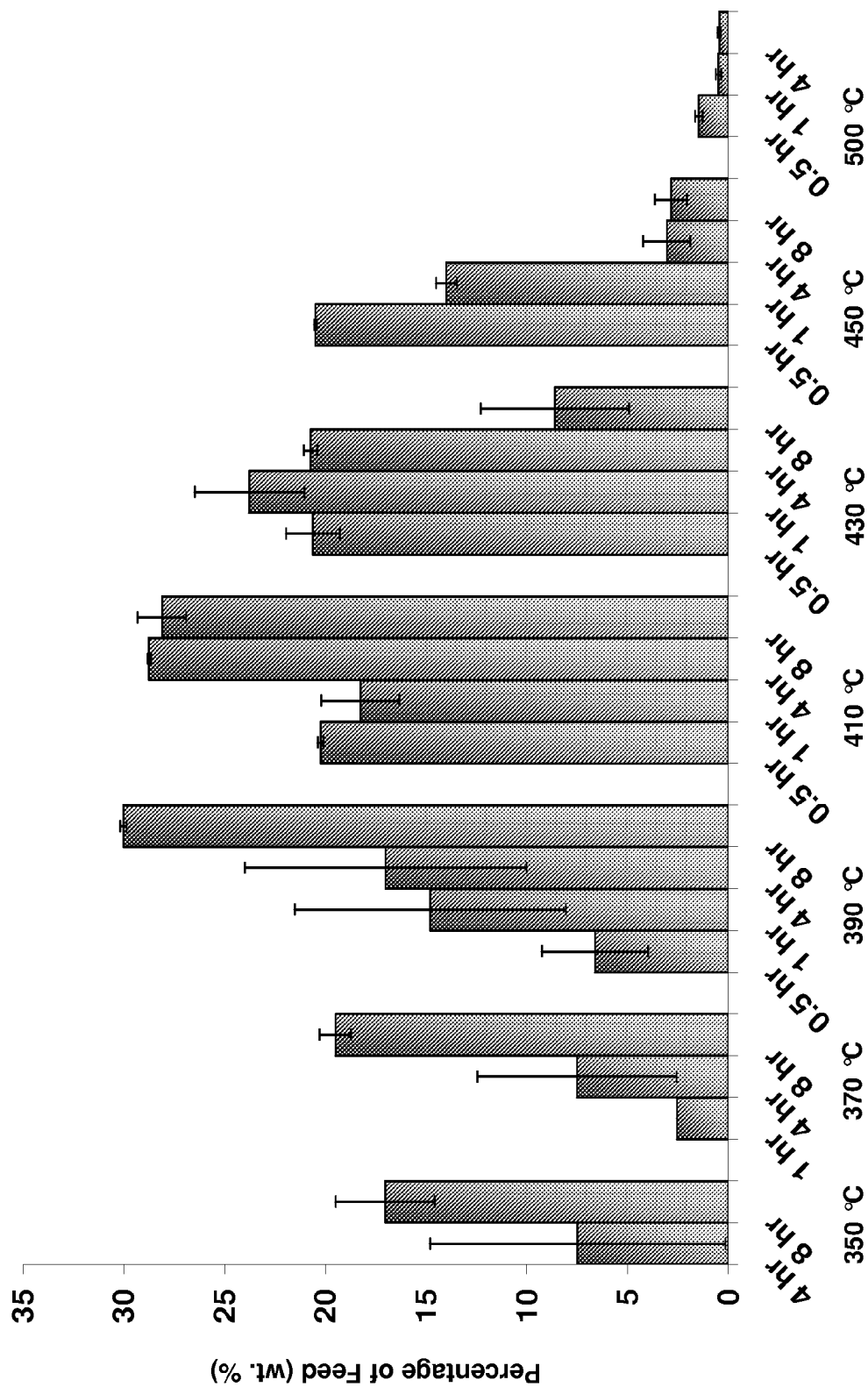
FIG. 27 shows the percentage of $C_8$-$C_{20}$ alkanes formed as a function of temperature and time.
Figure 28:
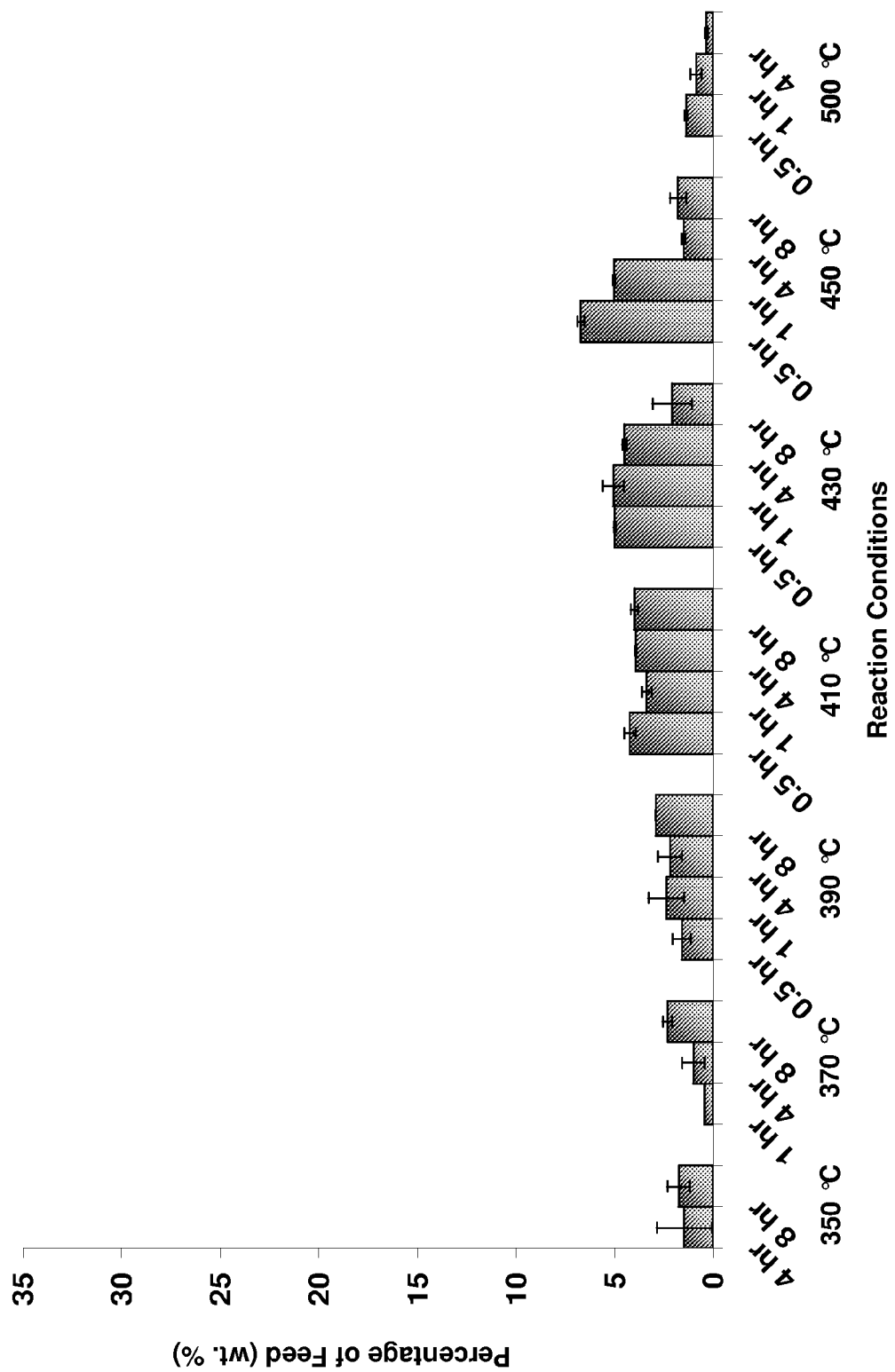
FIG. 28 shows the percentage of $C_8$-$C_{20}$ alkenes formed as a function of temperature and time.
Figure 29:
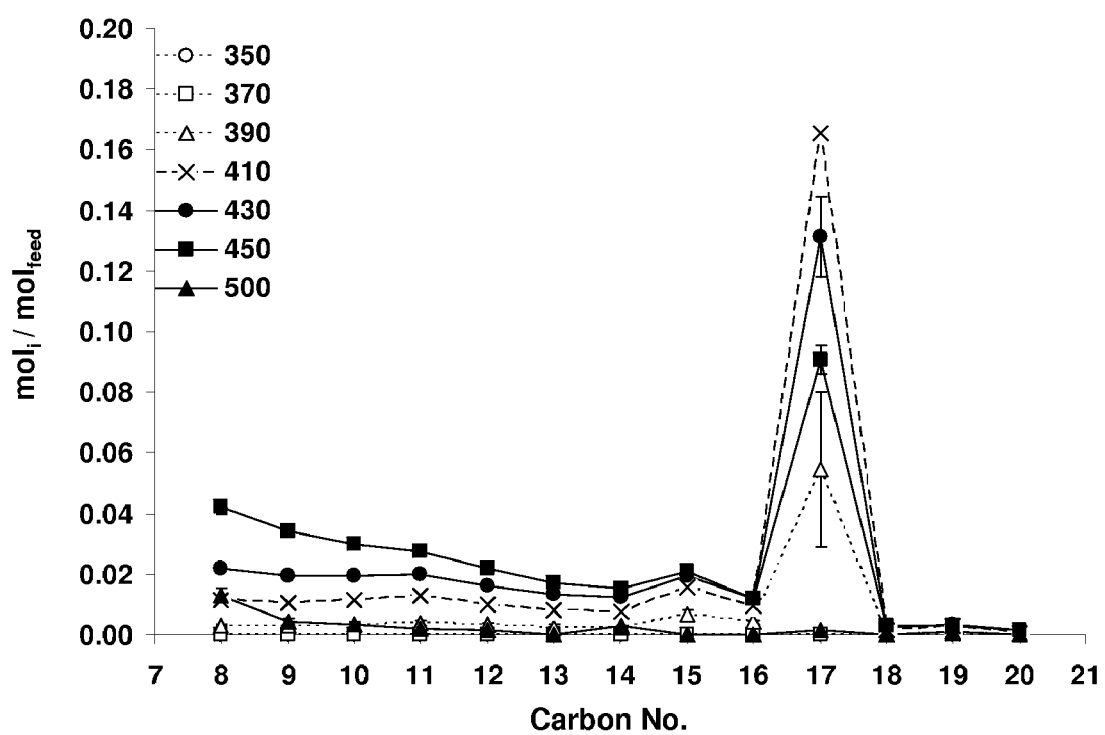
FIG. 29 shows the molar yields of $C_8$-$C_{20}$ alkanes as a function of temperature for 0.5 hr reactions
Figure 30:
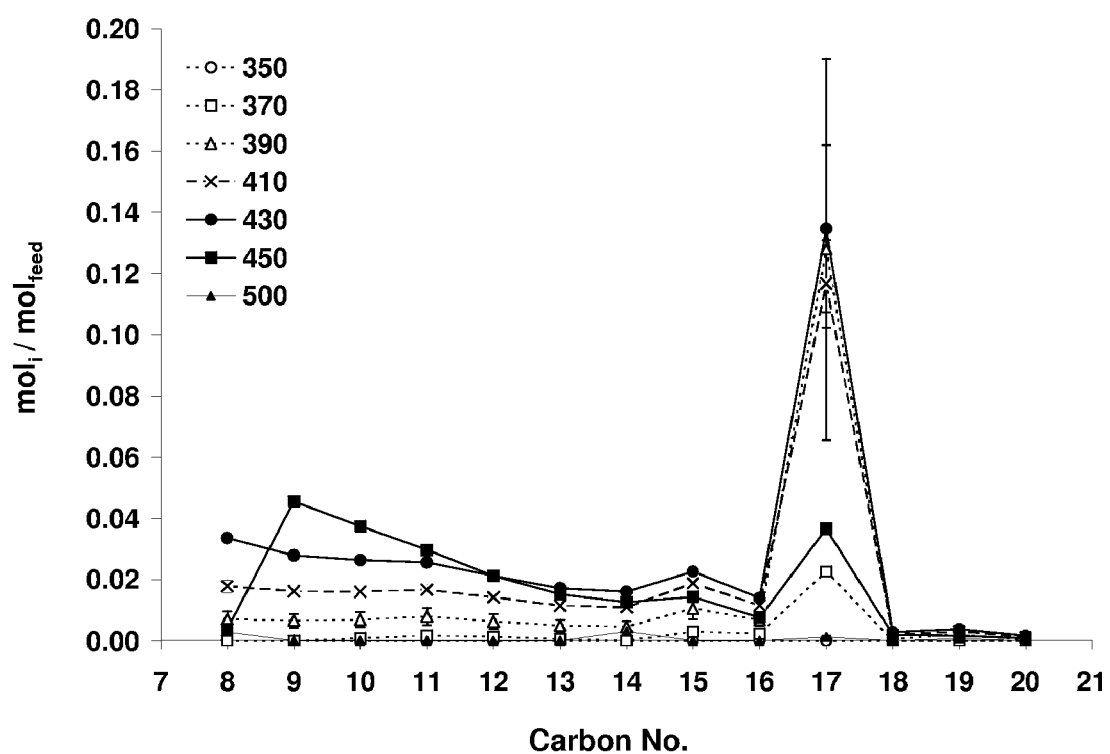
FIG. 30 shows the molar yields of $C_8$-$C_{20}$ alkanes as a function of temperature for 1 hr reactions.
Figure 31:
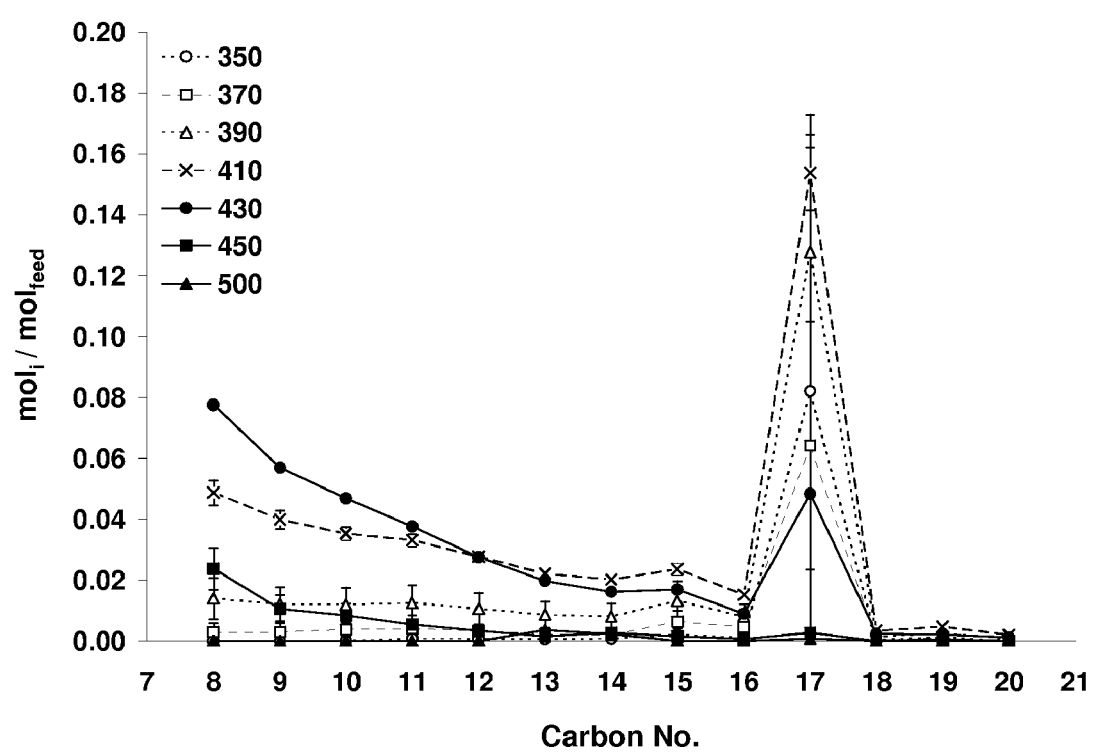
FIG. 31 shows the molar yields of $C_8$-$C_{20}$ alkanes as a function of temperature for 4 hr reactions.
Figure 32:
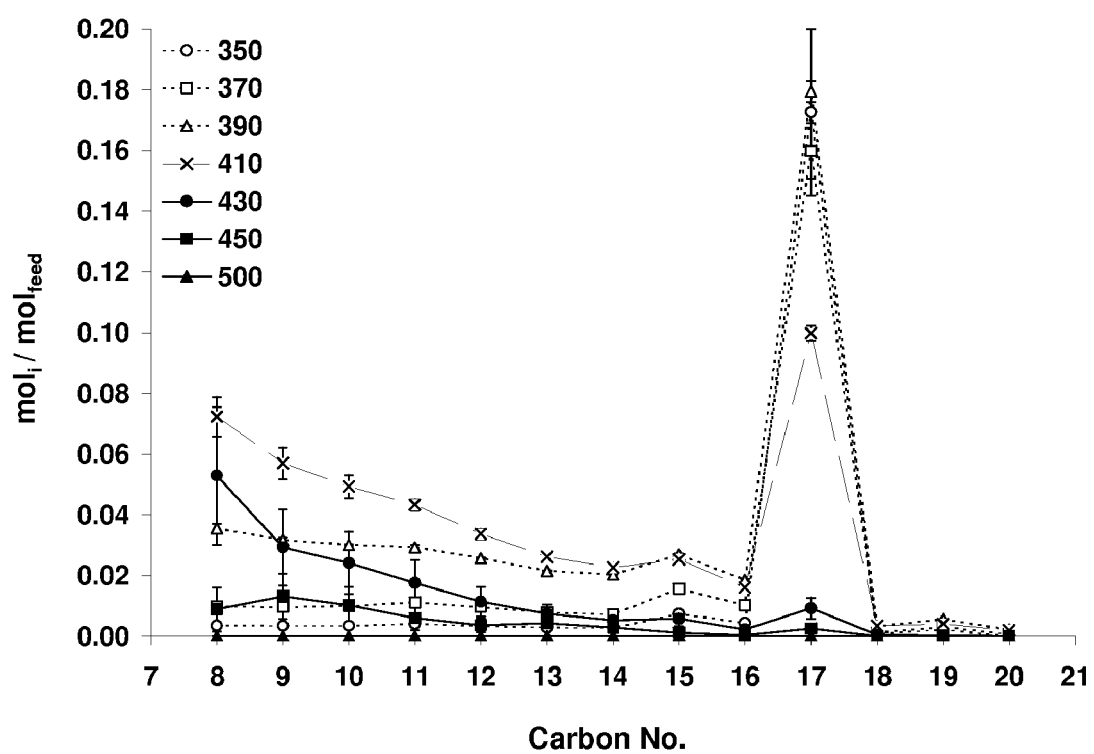
FIG. 32 shows the molar yields of $C_8$-$C_{20}$ alkanes as a function of temperature for 8 hr reactions.
Figure 33:
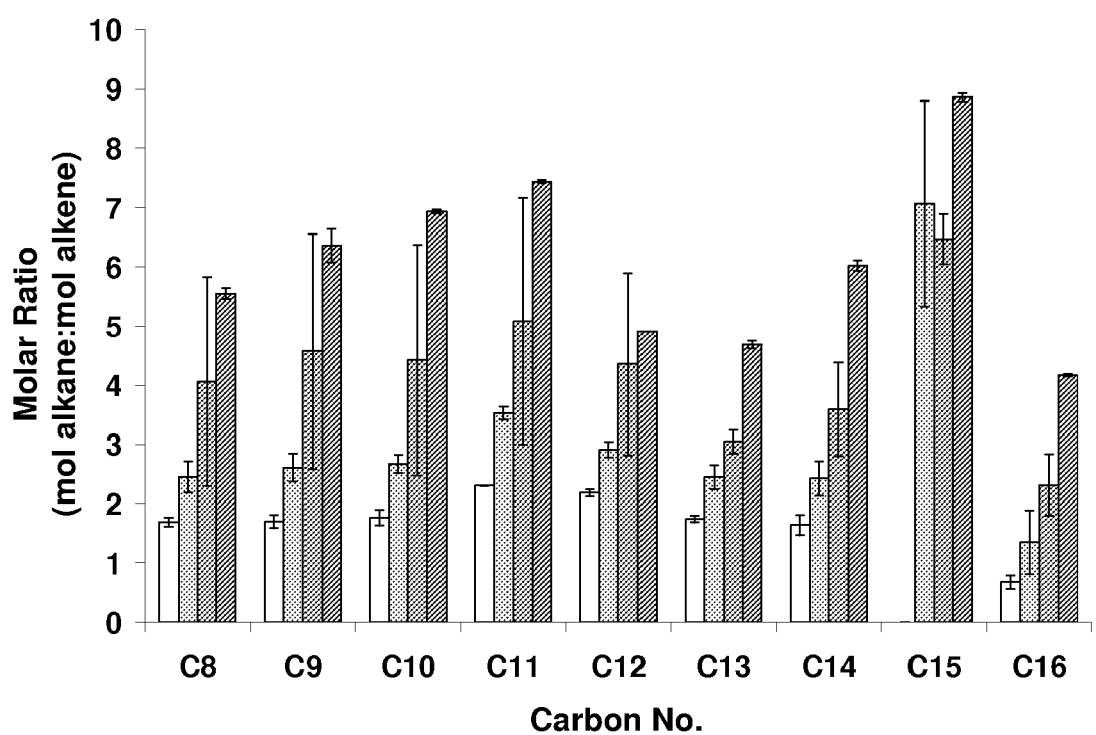
FIG. 33 shows the molar ratio of alkanes to alkenes as a function of carbon number and reaction time at T=390° C.
Figure 34:
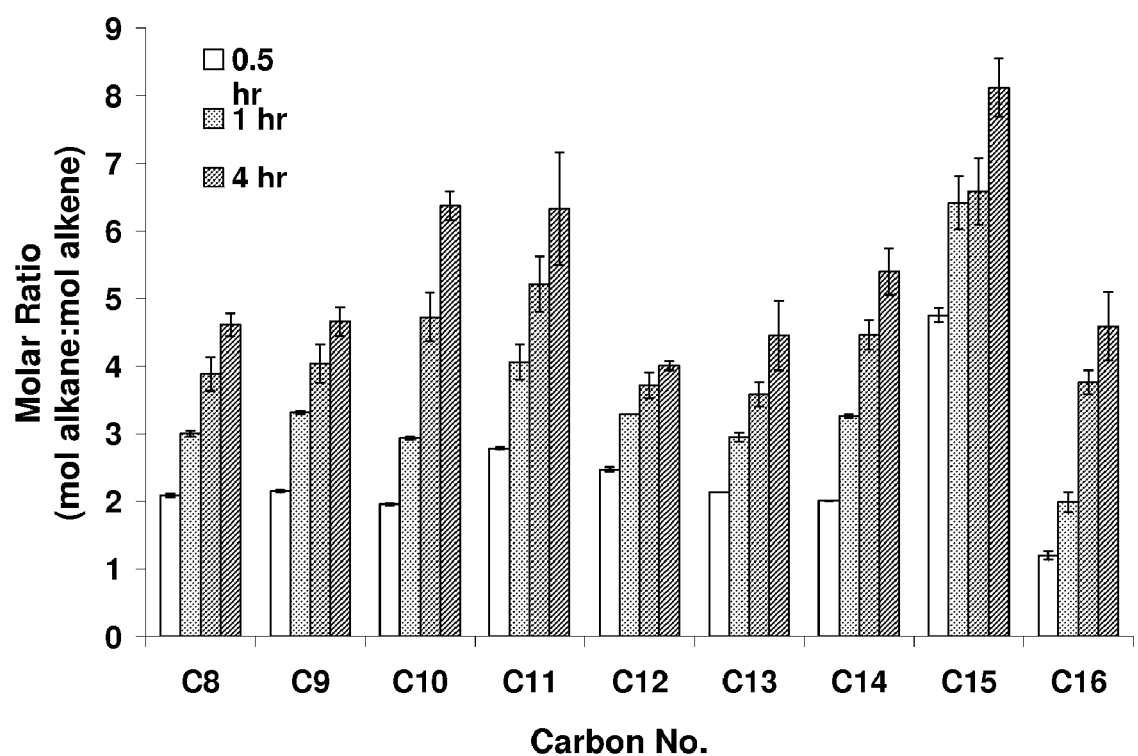
FIG. 34 shows the molar ratio of alkanes to alkenes as a function of carbon number and reaction time at T=410° C.
Figure 35:
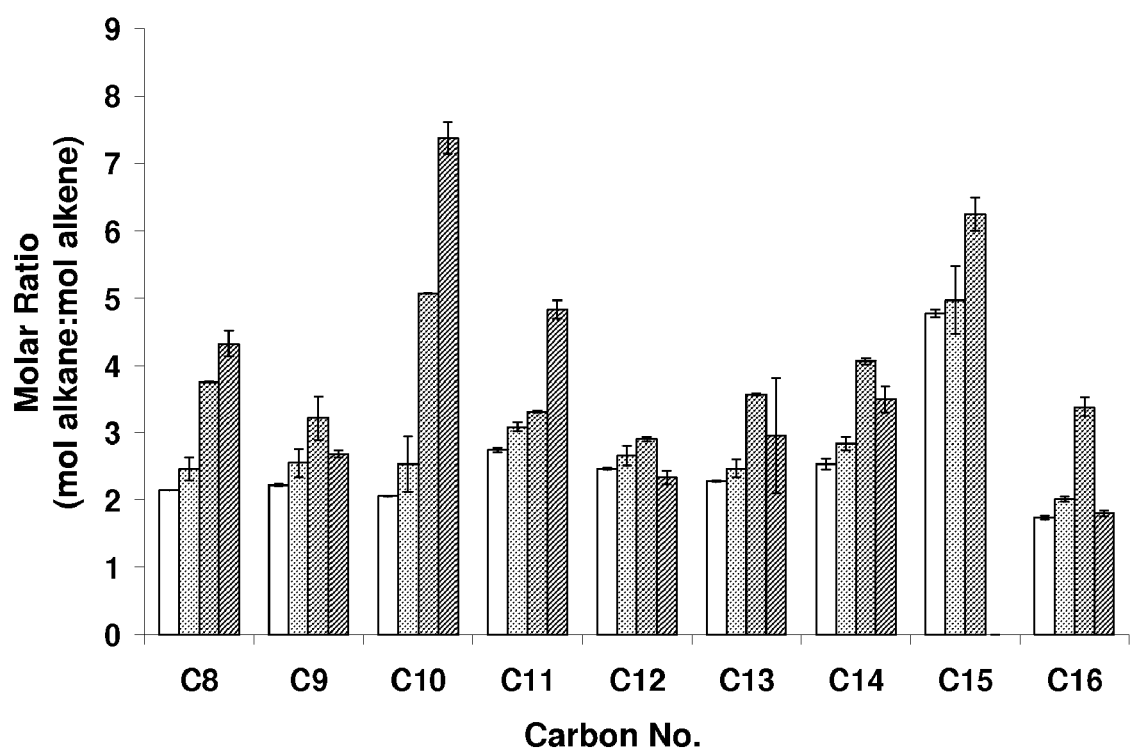
FIG. 35 shows the molar ratio of alkanes to alkenes as a function of carbon number and reaction time at T=430° C.
Figure 36:
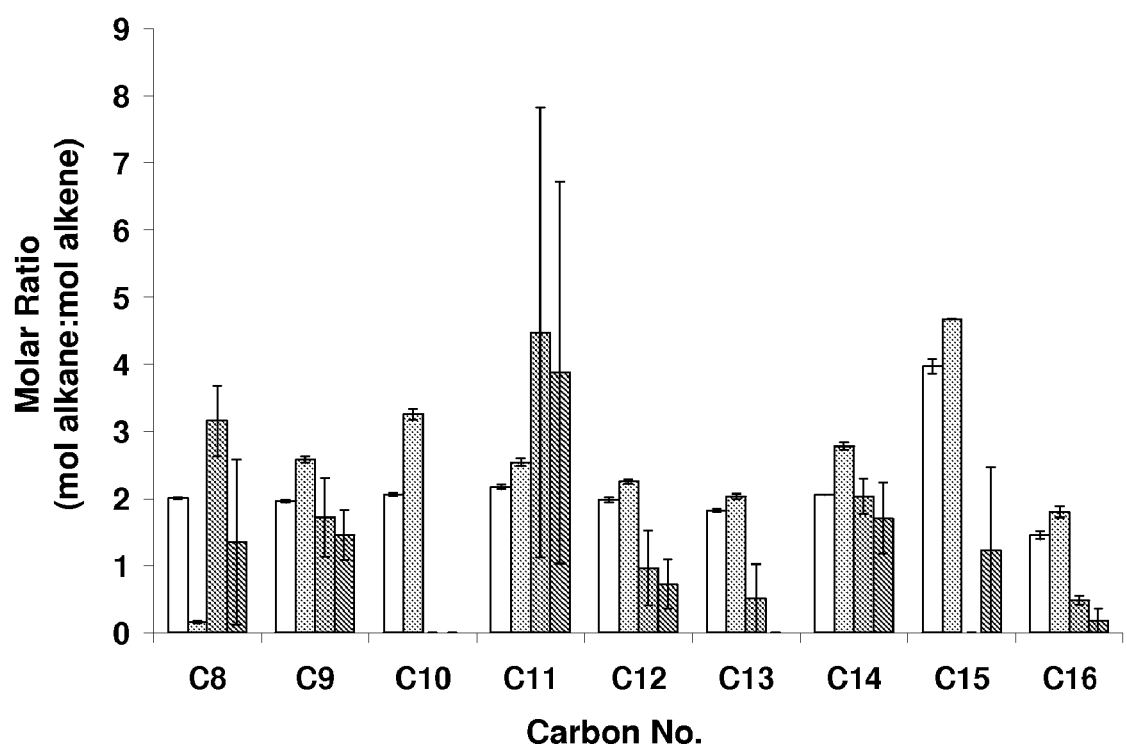
FIG. 36 shows the molar ratio of alkanes to alkenes as a function of carbon number and reaction time at T=450° C.

The main products of interest are the alkanes and alkenes. These compounds form the two most prominent ladder series in the pyrolysis products. Alkanes and alkenes from $C_8$-$C_{20}$ were identified on the chromatograms using the GC/MS data and external standards. Peak areas were used to semi-quantitatively determine the amount of each compound in the product mixture relative to the internal standard of known concentration. It is possible that at the milder reaction conditions that heptadecane ($C_{17}$) is underestimated as described in the previous section. Although it might not be completely accurate, the data should still provide, at worst, a conservative estimate of yield. FIGS. 27 and 28 show the percentage of $C_8$-$C_{20}$ alkanes and alkenes respectively, formed at different temperatures and times. It is important to note that the alkene that was quantified was the alkene peak that directly preceded the alkane peak. As explained earlier, data from GC/MS suggest that is likely a 1-alkene, however this has not been confirmed by other methods. Data from the GC/MS also suggest that the small peaks following the alkane (another "ladder") is also an alkene with the double bond in a different position. When the data was first analyzed, these peaks were diluted out. The GC vials were diluted prior to analysis because the $C_{17}$ peak overloaded the GC when a more concentrated sample was analyzed. FIGS. 20-26 represent analysis from the more concentrated samples (i.e. all reaction product dissolved in 10 ml of pentane); however, peak integrations were conducted using the diluted samples. Because the method used to quantitate the compounds is relative to the internal standard that was added during extraction of the products from the reactor, it should not affect the result. As such, the small alkene peak that appears after the alkane in the chromatogram is not considered in this analysis but will be discussed briefly later. The data represents the averages of duplicate runs and the error bars represent the standard error between the two runs. Looking at the FIGS. 27 and 28, it is clear that more alkanes are formed compared to alkenes. As well, the error bars at the more severe reaction conditions are smaller than at the milder conditions as has been observed in other results.

At 350, 370, 390, and 410° C., the amount of alkanes and alkenes formed increases with time. At 430° C. and above, the amount of alkanes and alkenes in the $C_8$-$C_{20}$ range start to decrease as the reaction time is increased. For example, at 430° C. a 4-hour reaction results in a combined total of 25.% $C_8$-$C_{20}$ alkanes and alkenes while after 8 hrs of reaction, this values decreases to 10.7%. At 450° C., and reactions longer than 4 hours, and 500° C. relatively little product in the $C_8$-$C_{20}$ range is formed. The maximum amounts of $C_8$-$C_{20}$ alkane and alkenes are formed at 410° C. after 4 hr (32.7%) and 8 hr (32.1%) reactions and at 390° C. after 8 hrs (32.9%).

Cracking Patterns of $C_8$-$C_{17}$ Hydrocarbons

The data from the chromatograms provides a decent estimation of yields but it can also be used to study the cracking behavior. Both molar selectivity and alkane to alkene ratio can give a good understanding of cracking behavior. This section will focus on the molar yields of the alkanes while the next section will look at the molar ratio. Peak areas from GC integration were converted into molar yields for $C_8$-$C_{20}$ alkanes. This data is presented in FIGS. 29-32. The figures represent the average of duplicate runs and the error bars represent the standard error between these runs. For clarity, the lower temperatures (350-390° C.) are illustrated with open data point markers and dashed lines while the higher temperatures (430-500° C.) are illustrated with solid data point markers and solid lines. The middle temperature, 410° C. is illustrated with x's and a longer dashed line (see legend). The cracking pattern of alkanes is of important because alkanes are the primary products of interest. The cracking behavior of alkenes is also important and is addressed in the next section on molar ratios between alkanes and alkenes.

In FIGS. 29-32, similar trends occur at each reaction time of 0.5, 1, 4, and 8 hours, however they occur at different temperatures. At the mildest conditions (low temperature, low time), very little reaction product is formed. For example at 350° C., products do not start forming until 4 hours.

Alkane:Alkene Ratio

The data from this experiment can be used to analyze the molar ratio of alkanes to alkenes, an important parameter in hydrocarbon cracking. Peak areas were used to calculate the alkane:alkene ratio. FIGS. 33-36 show the molar ratios of alkanes to alkenes as a function of carbon number and time at different reaction temperatures. Chains with 17 carbons (heptadecane/heptadecene ratio) were excluded from these figures because the ratio was so large that it made it difficult to see the changes in $C_8$-$C_{16}$ ratios. This ratio is discussed separately in the next section. As in the previous section, the figures represent the averages from duplicate runs and the error bars represent the standard error between the runs. Errors were generally smaller for this data than for the estimations of yield. It is likely that a large percentage of the error between the two samples is due to the extraction method and the amount of compound that is extracted. This would likely affect the amount of compound in the extracts, but unlikely to affect the ratio of alkanes to alkenes, which should be independent of concentration.

It is important to note that because this data represents the average of only duplicate runs significance tests cannot be conducted. General trends will be noted based on the graphs but it is not known whether or not any of the differences mentioned have true statistical merit. For this set of experiments, the molar ratios are almost always greater than 1, meaning that more alkanes are produced than alkenes. Looking back at the results of the initial studies (FIG. 11), it is clear that during the five-minute reactions at 500° C., the alkenes were produced in greater quantities than the alkanes. This is also evident for the 0.5-hour reactions at 450° C., but to a lesser extent. The results of the current experiment show that the molar ratio is less than one at only a few conditions, most noticeably at 450° C. for the 4 and 8 hour reactions and only for certain carbon numbers, namely $C_{12}$-$C_{14}$ and $C_{16}$.

Changes in Molar Ratio Over Time

In FIGS. 30-33, the trend is that at 390° C. and 410° C., the molar ratio increases with time. A higher molar ratio indicates that more alkanes are produced relative to alkenes, or alkanes are produced preferentially to alkenes. For example, at 390° C. the molar ratio of $C_8$ increases from 1.69±0.07 after 0.5 hours to 5.55±0.09 after 8 hours. Likewise, the molar ratio of $C_{16}$ increases from 0.69 0.11±after 0.5 hours to 4.17±0.22 after 8 hours. Similar trends are observed for the carbon numbers in between. At 430° C., some compounds ($C_8$, $C_{10}$, $C_{11}$, and $C_{15}$) show increasing molar ratio with time, however others ($C_9$, $C_{12}$, $C_{14}$, $C_{16}$) show a decrease in molar ratio between the 4 and 8 hr reactions. At 450° C., it looks as if the molar ratio begins to decrease even earlier, between the 1 and 4 hr reaction. In summary, the molar ratio increases with time from 0.5-8 hrs until a certain temperature where the longer reaction times result in a decrease in molar ratio.

Changes in Molar Ratio with Temperature

The temperature does not have as much of an influence on the molar ratio as time does at temperatures between 390° C. and 430° C. At each reaction time there appears to be a maximum ratio at a certain temperature and as the reaction time is increased the temperature at which the maximum occurs decreases. For example, for 0.5 minute reactions, the maximum ratios appear to be at 410° C. or 430° C. while for 8 hr reactions, the maximum ratios occur at much lower temperatures around 370° C. or 390° C.

Time and Temperature Effects

Although statistical analysis was not conducted, it is clear that both temperature and time affect the molar ratio. The mildest conditions (low temperatures and times) results in a relatively low molar ratio but so do the most severe (longest times and highest temperatures). The optimal ratio lies somewhere in between these two extremes. At the conditions tested, the largest ratio occurred at 370° C. for 8 hr reactions. The 8 hr reaction at 350° C. did result in slightly lower ratios, however since reactions were not conducted at times longer than 8 hrs, it is possible that reactions longer than this at 350 or 370° C. could result in higher molar ratios.

Changes in Molar Ratio with Carbon Number

Another variable to consider is the number of carbons that the alkane and alkene chains have. For this analysis, $C_8$-$C_{16}$ carbons were investigated. The distributions of molar ratios for each compound relative to one another appears to be consistent at the different times and temperatures aside from the fact that at higher temperatures (430° C. and above) the molar ratios of $C_8$ and $C_9$ decrease more, relative to the other compounds. For most of the temperatures, $C_8$-$C_{11}$ and $C_{15}$ have larger molar ratios than $C_{12}$-$C_{14}$, and $C_{16}$. It is evident that $C_{15}$ has the highest molar ratio, while $C_{16}$ has the lowest. For example at 410° C. a 1 hr reaction results in a molar ratio of 4.75±0.06 for $C_{15}$ but only 1.20±1.16 for $C_{16}$. At 390° C. an 8 hr reaction results in a molar ratio of 8.86±0.07 for $C_{15}$ and 4.17±0.02 for $C_{16}$.

Molar Ratios of $C_{17}$

Figure 37:
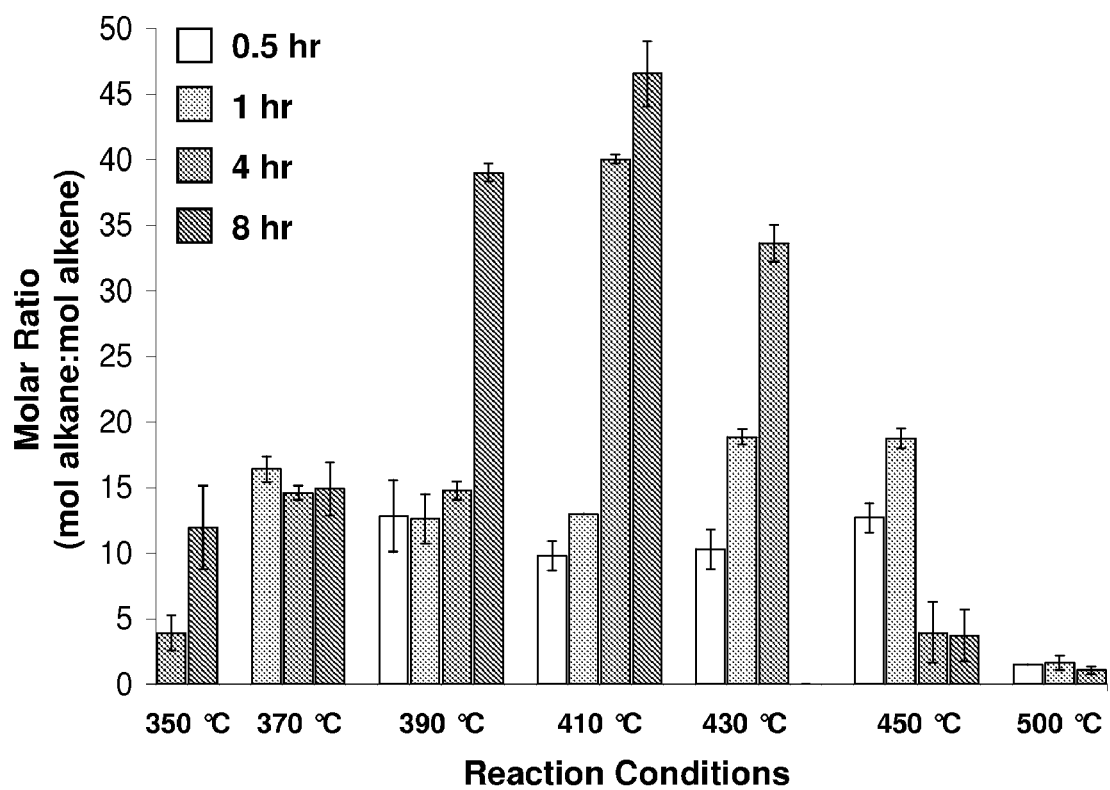
FIG. 37 shows the molar ratio of alkanes to alkenes for $C_{17}$ as a function of temperature and time.

FIG. 37 shows the molar ratio for $C_{17}$, or heptadecane to heptadecene. It has been established that heptadecane is the major reaction product and that there is very little heptadecene. The molar ratios, which are substantially higher for $C_{17}$ than for $C_8$-$C_{16}$, reflect this. In the $C_8$-$C_{16}$ range, $C_{15}$ had the highest molar ratios. At 390° C. the molar ratio after an 8-hour reaction was 8.86±0.07. In contrast, at the same condition the molar ratio for $C_{17}$ was 39.0±0.71. Again, because reactions longer than 8 hours were not conducted, it is possible that the maximum molar ratio lies outside the conditions tested. The largest molar ratio for $C_{17}$, 43.53±3.59, occurred at 410° C. for an 8 hr reaction. The data suggests $C_{17}$ follows the same trends as the $C_8$-$C_{16}$ hydrocarbons. For example at 390-430° C., the molar ratio increases with time, but at higher temperatures such as 450° C., longer times (4 and 8 hours) result in decreased ratios. At 500° C., the ratios are low for all of the times tested.

Analysis of Light Ends (Gas Fraction)

Composition

Figure 38:
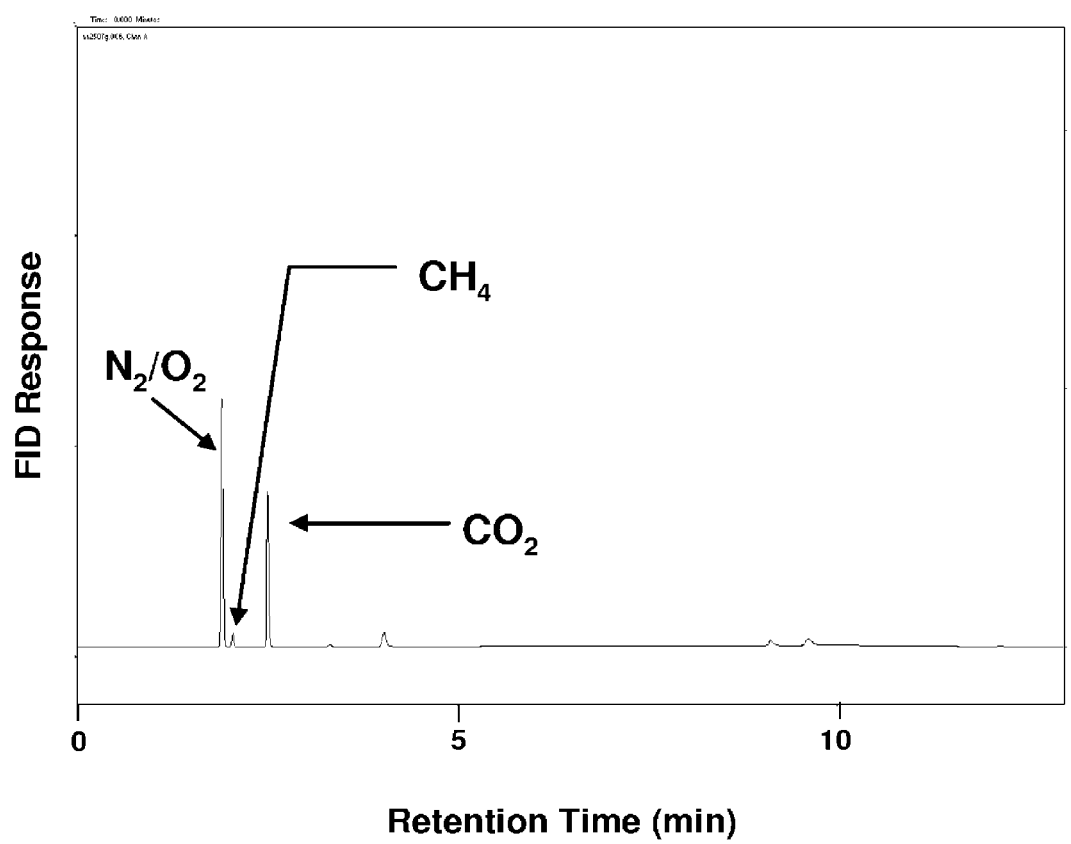
FIG. 38 shows the typical gas composition from stearic acid pyrolysis from a 1 hr reaction at 410° C. as analyzed on GC-TCD.
Figure 39:
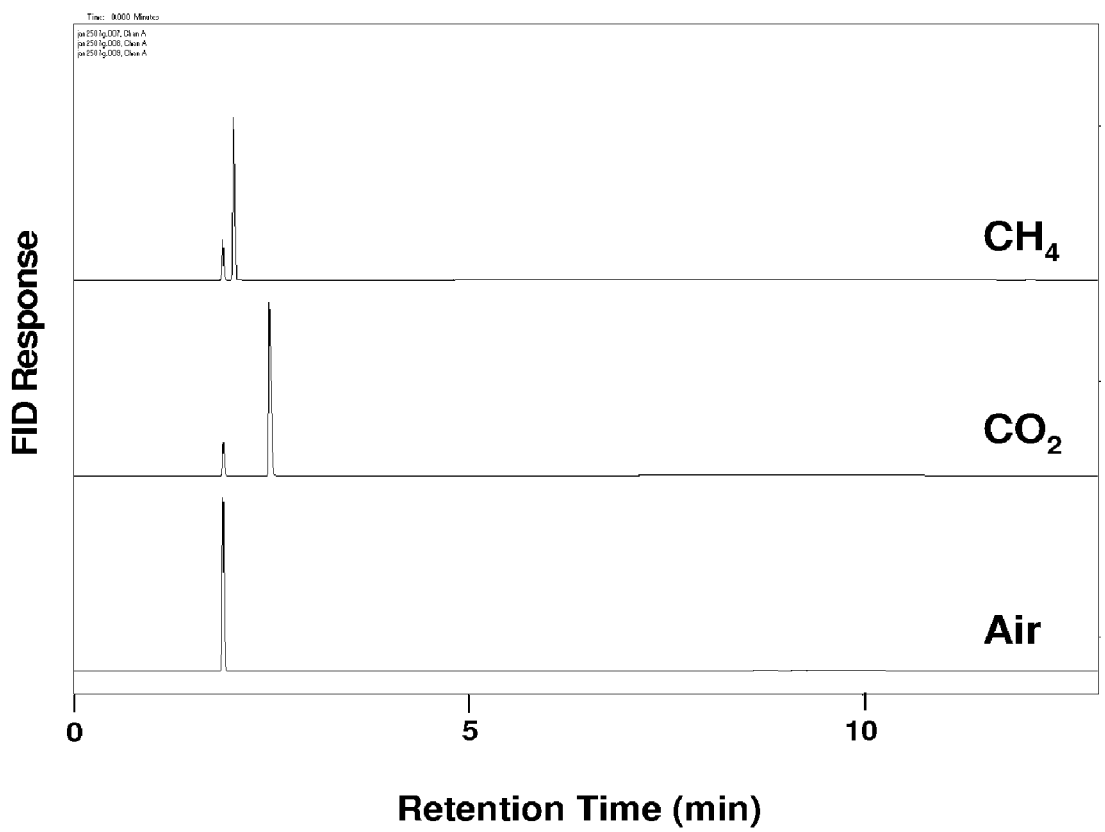
FIG. 39 shows methane ($CH_4$), carbon dioxide ($CO_2$), and air standards as analyzed on GC-TCD.

Typical chromatograms showing the composition of the gas fraction as analyzed on GC-TCD are presented in FIG. 38. Methane ($CH_4$), carbon dioxide ($CO_2$), and room air standards were also analyzed and are shown in FIG. 39. Due to the sensitivity of the detector, $N_2$ and $O_2$ are detected as single peak. This means that the first peak in the chromatograms can be $N_2$, $O_2$, air or any combination of the three. For simplicity, this will be referred to as the "$N_2/O_2$ peak". Comparing peak retention times from the sample (FIG. 37) with the peak retention times from the standards (FIG. 38) it is evident the gaseous fractions contain "$N_2/O_2$", $CH_4$, and $CO_2$. The majority of the $N_2/O_2$ peak can likely be attributed to the $N_2$ atmosphere inside the reactor and small amounts of air from the sample vacutainer or the injection syringe. There are small amounts of air present in the $CO_2$ and $CH_4$ standards (FIG. 39), indicating that small amounts of air are entering the GC, likely through the syringe. There are also two sets of smaller peaks at later retention times, which appear to be in doublets. These peaks are likely light hydrocarbon gases such as ethane and propane, however this was not confirmed analytically. Analysis of the gaseous fraction was analyzed numerous times and compositions obtained from the fractions after one hour reactions at 390° C. and 410° C. as well as a 30 minute reaction at 500° C. all yielded similar results.

Percentage of Feed

Figure 40:
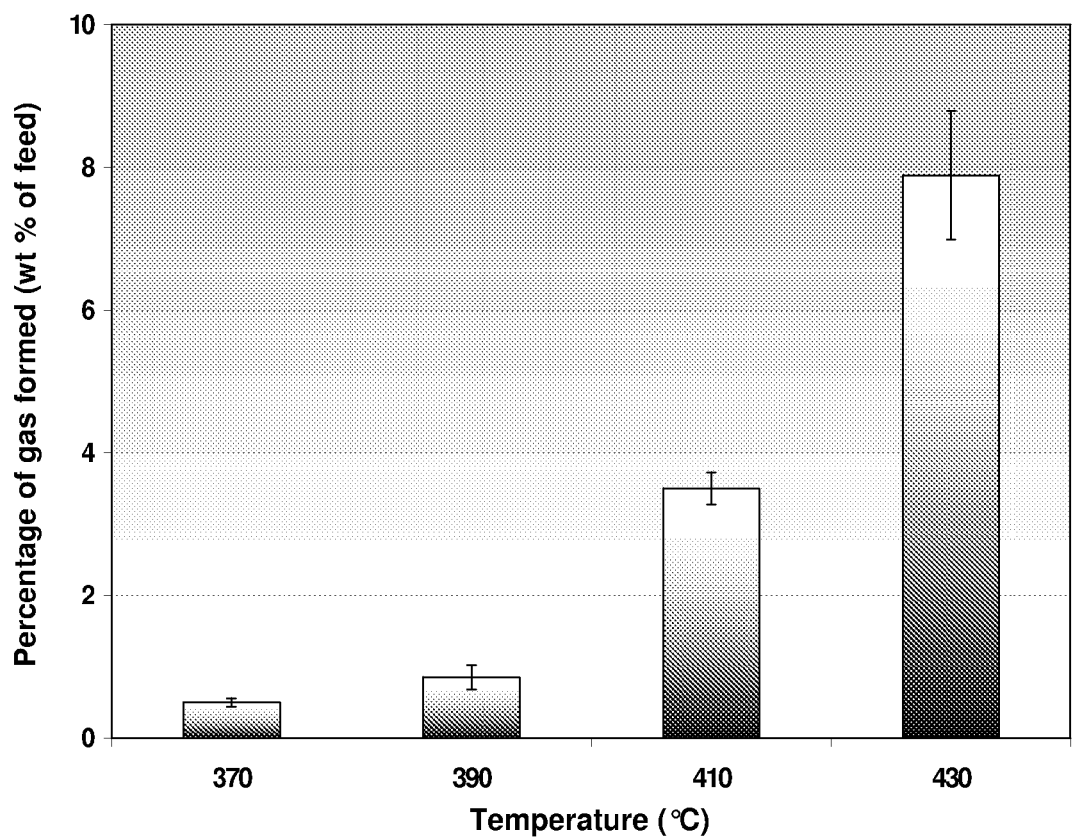
FIG. 40 shows the percent of gas products formed during 1 hr stearic acid pyrolysis reactions as a function of temperature, where the initial pressure was atmospheric and the reactions were conducted in $N_2$.

FIG. 40 shows the percentage of gas formed at various temperatures during 1 hr reactions. For this experiment, reactions were conducted using approximately 5.0 g of stearic acid feed instead of the usual 1.0 g. More starting feed was used so that the difference in the weight of the gas, measured by weighing the reactor before and after venting, was detectable on the scales available in the lab. FIG. 40 shows that as the temperature increases, the amount of gas products formed also increases. At 370° C., only 0.50 wt. % of gas is formed but at 430° C., an average of 7.89 wt. % of gas product is formed. Reactions were conducted at 450° C.; however, with that much feed the pressure build-up was so high that two of the reactors leaked and two of the reactors spewed oil during venting despite the fact that the samples were allowed to cool overnight and the vent valve was turned slowly. Because this resulted in a loss of oil, no accurate data was obtained. The shape of this graph indicated that in the temperature range tested, the formation of gas is not linear with respect to temperature.

Estimate of Liquid Yield

Figure 41:
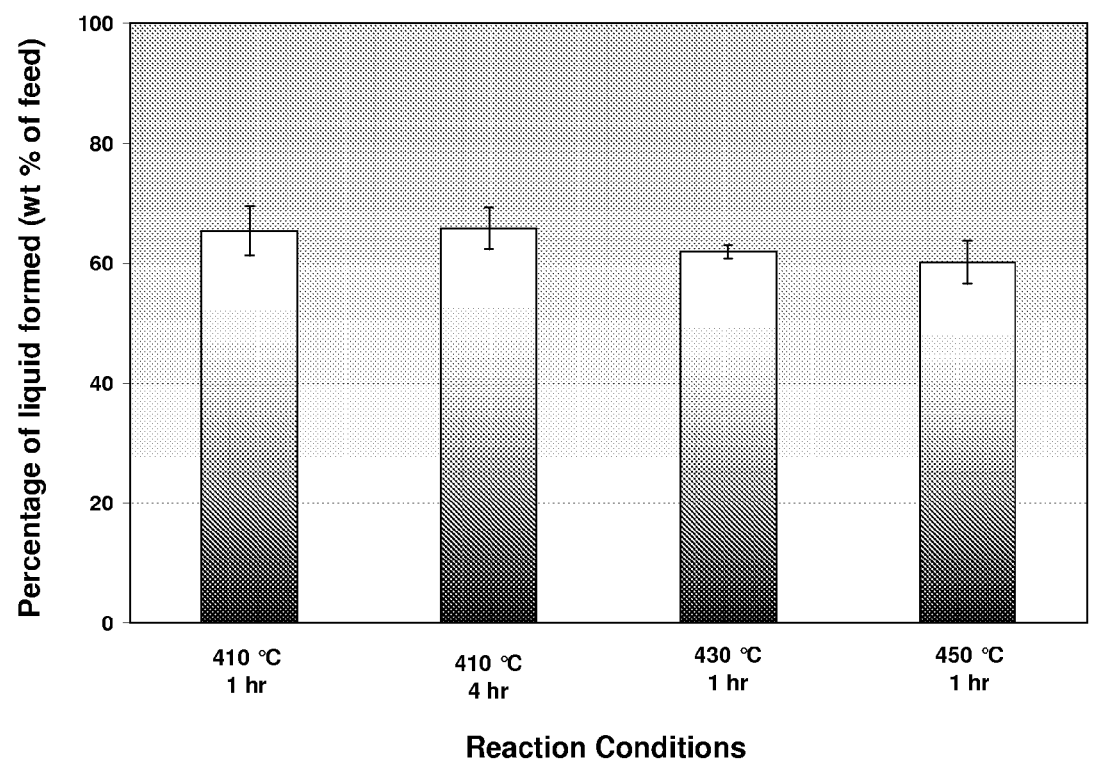
FIG. 41 shows the percent of liquid products formed during stearic acid pyrolysis as a function of temperature and time, where the initial pressure was atmospheric and the reactions were conducted in $N_2$.

To get a crude estimate of liquid yield, the liquid product was extracted with a Pasteur pipette from the reactor (no solvent was added) and weighed. Results are presented in FIG. 41. At 390° C., there was no liquid product in the reactor. The product consisted of white-brown powder. At 410° C., after a one-hour reaction, three runs (data not shown) also resulted in no liquid product, however the other 3 runs resulted in liquid products between 58-71%.

Extent of Reaction

Figure 42:
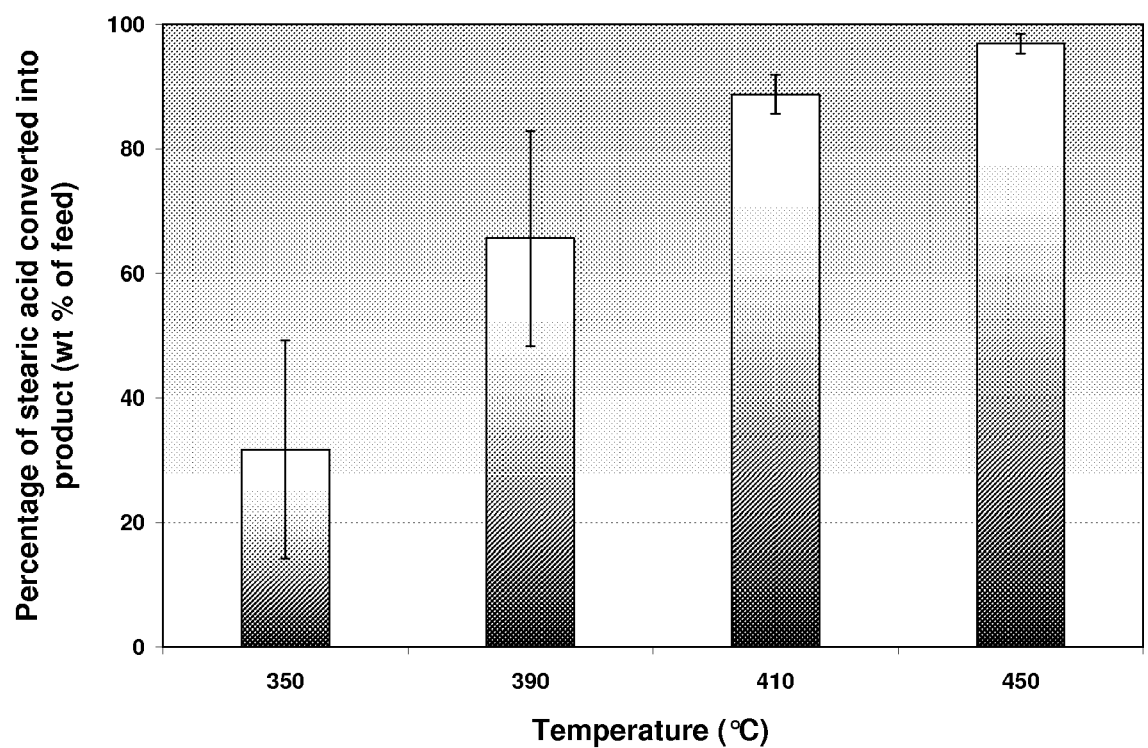
FIG. 42 shows the percentage of initial stearic acid feed that was converted during 1 hr pyrolysis reactions as a function of temperature, where the initial pressure was atmospheric and the reactions were conducted in $N_2$.

Generally, fatty acids do not create sharp peaks on the GC. They have a tendency to spread on the column resulting in wide, "shark fin" peaks that are difficult to quantify. For this reason, fatty acids are first derivatized into methyl esters before GC analysis. To avoid changing the structure of the other sample products, none of the samples were derivatized prior to analysis. Therefore, quantitation of unreacted feed based on the underivatized samples is not likely to be accurate. Furthermore, pentane was used as the primary extraction solvent, which is not the best choice for dissolving fatty acids. The stearic acid peak is not likely to be totally representative of the actual amount of unreacted material. FIG. 42 shows the percentage of stearic acid feed converted into product during the reactions (i.e. 100% of unreacted stearic acid). The data represents the average of fours runs. As expected, as the temperature increases, more feed is converted. At the lowest temperature, 350° C., only 31.70% of the stearic acid is converted. At the highest temperature, 450° C., nearly 95% of the product was converted. It is also worthwhile to note that at the higher temperatures, the error bars were much smaller than at the lower temperatures. This is likely due to the nature of the reaction product as well as the extraction method. At lower temperatures where the product is mostly solid, it sticks to the reactor and is difficult to extract. Despite stirring this material during the extractions, it is more likely that some of the compound may not have been dissolved in the pentane. At higher temperatures, when the reaction products are liquid, they dissolve easily into the pentane.

Minimum Cracking Temperature

Figure 43:
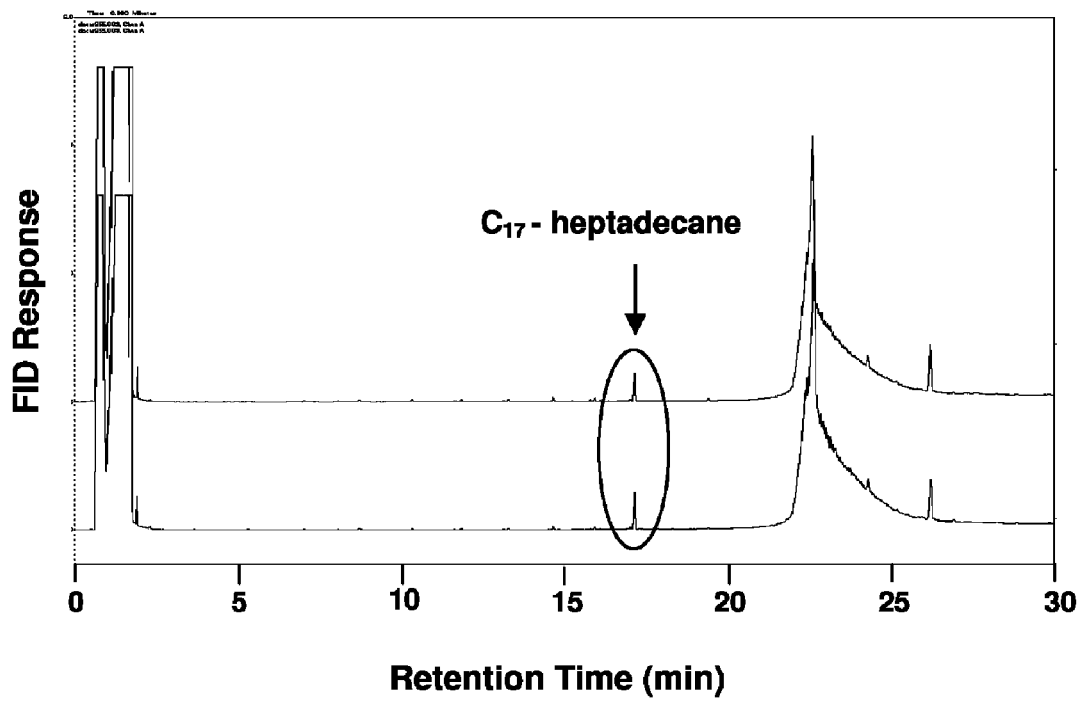
FIG. 43 is a chromatogram (GC-FID) showing stearic acid pyrolysis products after a 4 hr reaction at 255° C., where the initial pressure was atmospheric and the reactions were conducted in $N_2$.
Figure 44:
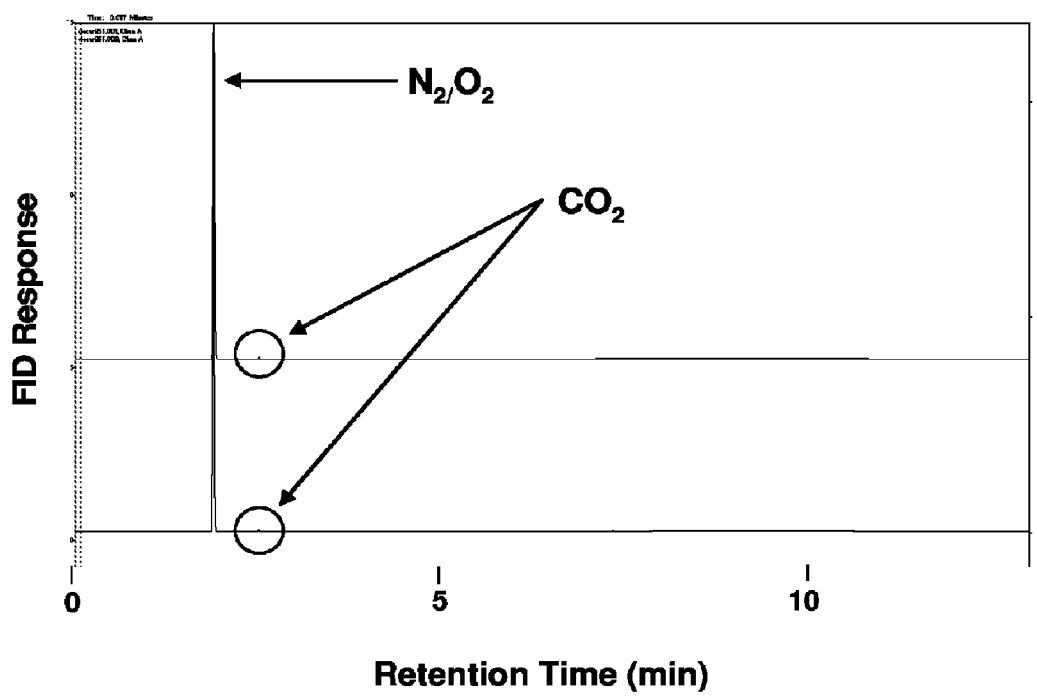
FIG. 44 is a chromatogram (GC-TCD) showing gaseous reaction products after a 4 hr reaction at 255° C., where the initial pressure was atmospheric and the reactions were conducted in $N_2$.

To determine the minimum temperature at which decarboxylation occurs, 4-hour reactions were conducted starting at 350° C. and decreasing therefrom. Duplicate runs at 255° C. still showed a $C_{17}$ peak (FIG. 43). Analysis of a gas sample taken from this reaction showed an extremely small, but evident $CO_2$ peak as shown in FIG. 44.

Pyrolysis of Oleic Acids

Figure 45:
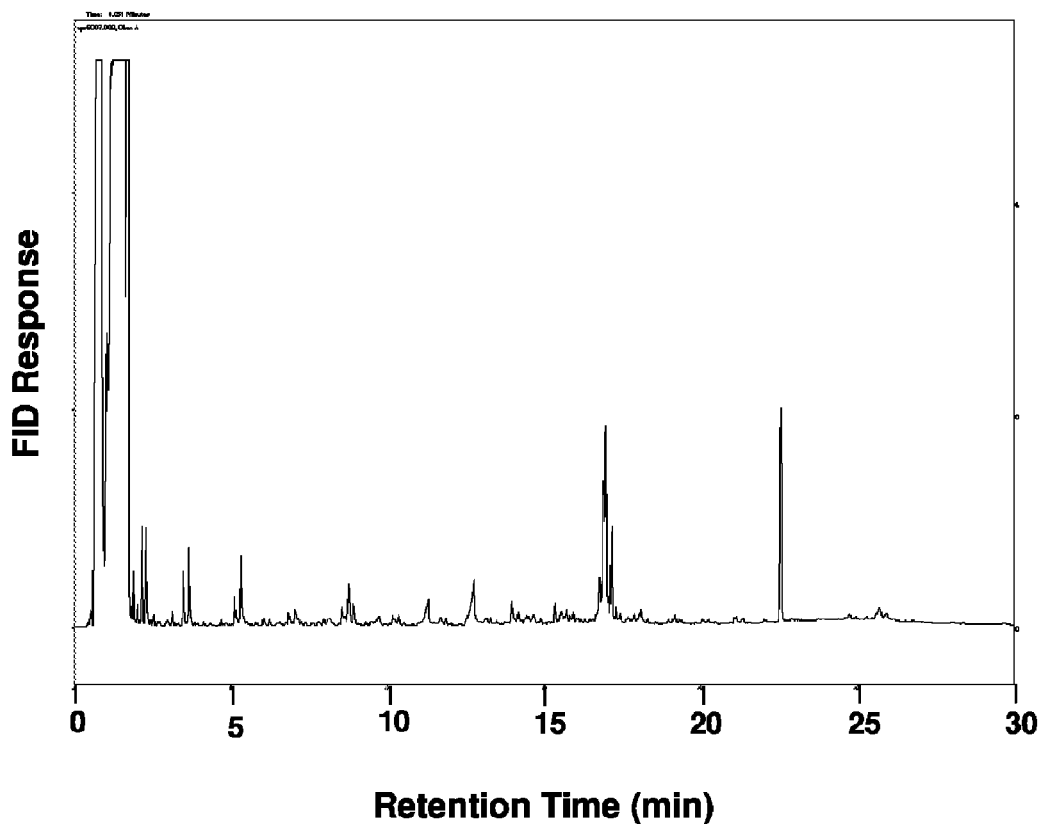
FIG. 45 is a chromatogram (GC-FID) showing oleic acid pyrolysis products after a 1 hr reaction at 410° C., where the initial pressure was atmospheric and the reactions were conducted in $N_2$.
Figure 46:
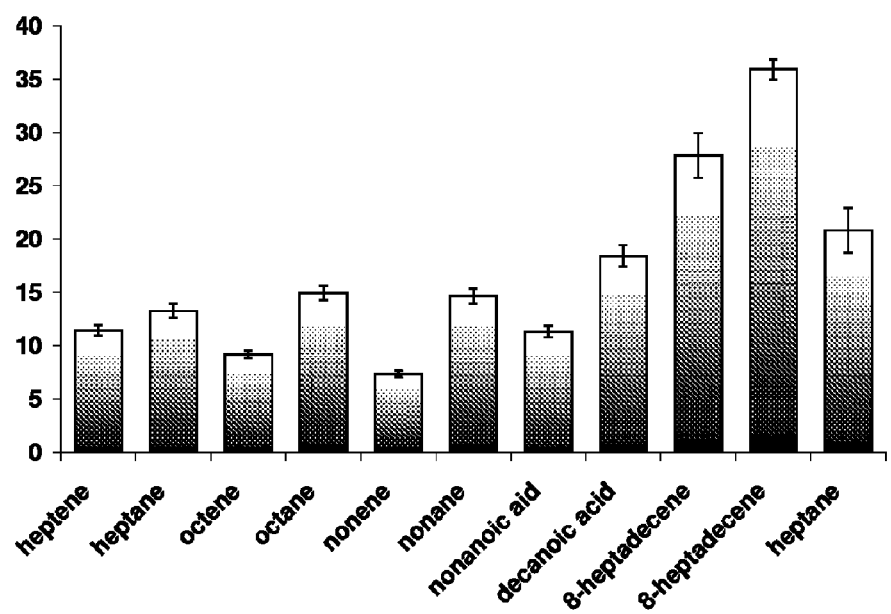
FIG. 46 shows the main products of oleic acid pyrolysis after 1 hr at 410° C.

It is of interest to see if the cracking behavior of an unsaturated fatty acid differs from that of a saturated fatty acid. Oleic acid, a free fatty acid with cis-double bond in the 9-position, was pyrolyzed for one hour at 410° C. using standard reaction and extraction procedures. The GC-FID chromatogram is shown in FIG. 45. The main products were identified using the GC-FID chromatograms and comparing them to the external alkane and fatty acid mixtures as well as GC/MS. The amounts of various compounds were determined semi-quantitatively and are presented in FIG. 46. This graph shows the averages of the fours runs and the error bars represent standard error. FIG. 46 shows the primary reaction products resulting from the thermal cracking of oleic acid at 410° C. after 1 hr. The largest amount of product formed was 8-heptadecene. Two bars show 8-heptadecene, possible due to a difference in conformation. This indicates that decarboxylation is likely an initial step in the thermal cracking of oleic acid. The most notable difference between oleic acid and stearic acid cracking is the absence of the prominent alkane/alkene ladder series at higher carbon numbers. This ladder is evident at lower carbon numbers, $C_9$ and lower and FIG. 46 shows that heptane/heptene, octane/octane, and nonane/nonene were among the primary reaction products formed. This would be consistent with cracking at the double bond of the decarboxylated chain. It is also interesting to note the presence of nonanoic and decanoic acid, at concentrations of 11.31±0.52 and 18.41±1.01 mg/g feed, respectively.

The sum of the products identified in FIG. 46 only represents 18.4% of the total products formed (including the gas products). Looking at the chromatogram (FIG. 45), it is evident that there are a number of minor peaks. Analysis of these peaks by GC/MS indicated that several of the peaks are likely cyclic components such as cyclopentanes and cyclohexanes with different methyl and ethyl groups attached.

Figure 47:
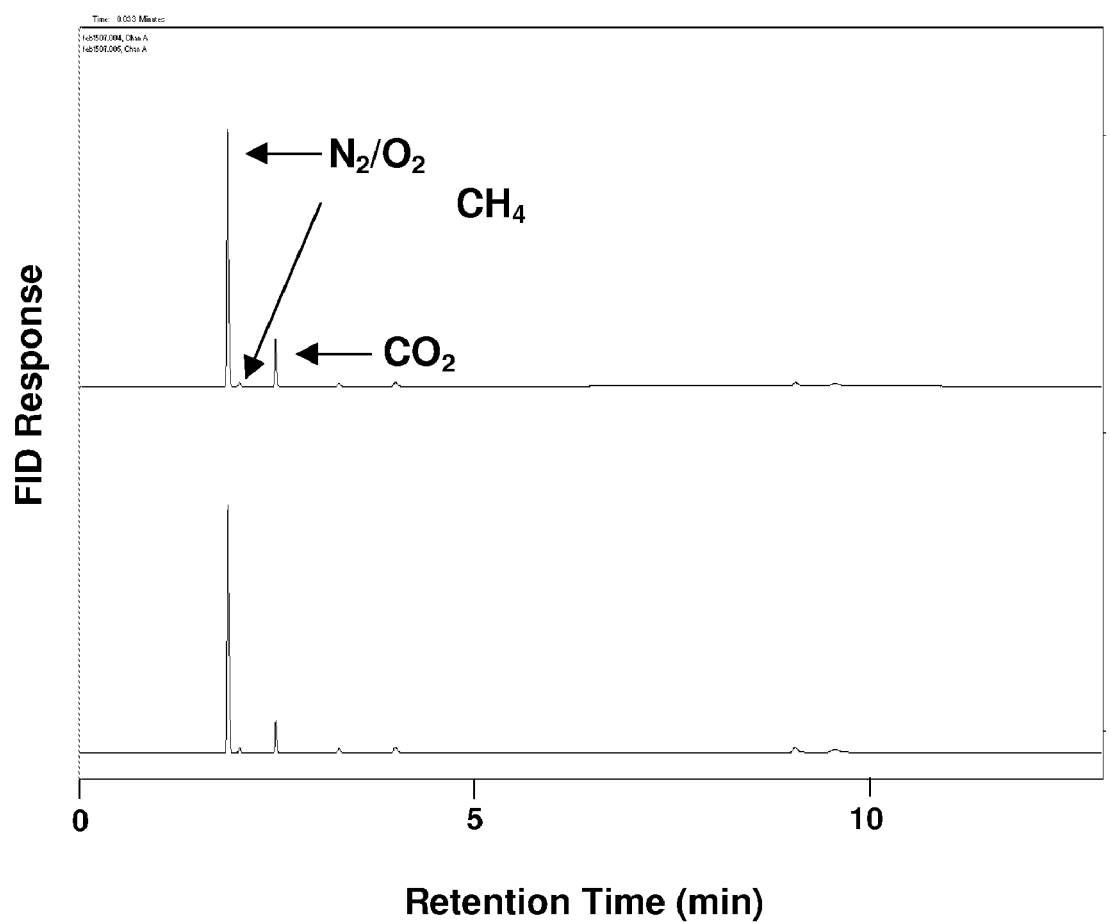
FIG. 47 are duplicate chromatograms (GC-TCD) showing the gas products from oleic acid pyrolysis after 1 hr at 410° C., where the initial pressure was atmospheric and the reactions were conducted in $N_2$.

Gas samples were also collected from the pyrolysis of oleic acid. Duplicate chromatograms from the GC-TCD analysis are shown in FIG. 47. Results are similar to the gas products formed during pyrolysis of oleic acid. The results show a large $N_2/O_2$ peak, a small $CH_4$ (methane) peak as well as a $CO_2$ (carbon dioxide) peak.

Figure 48:
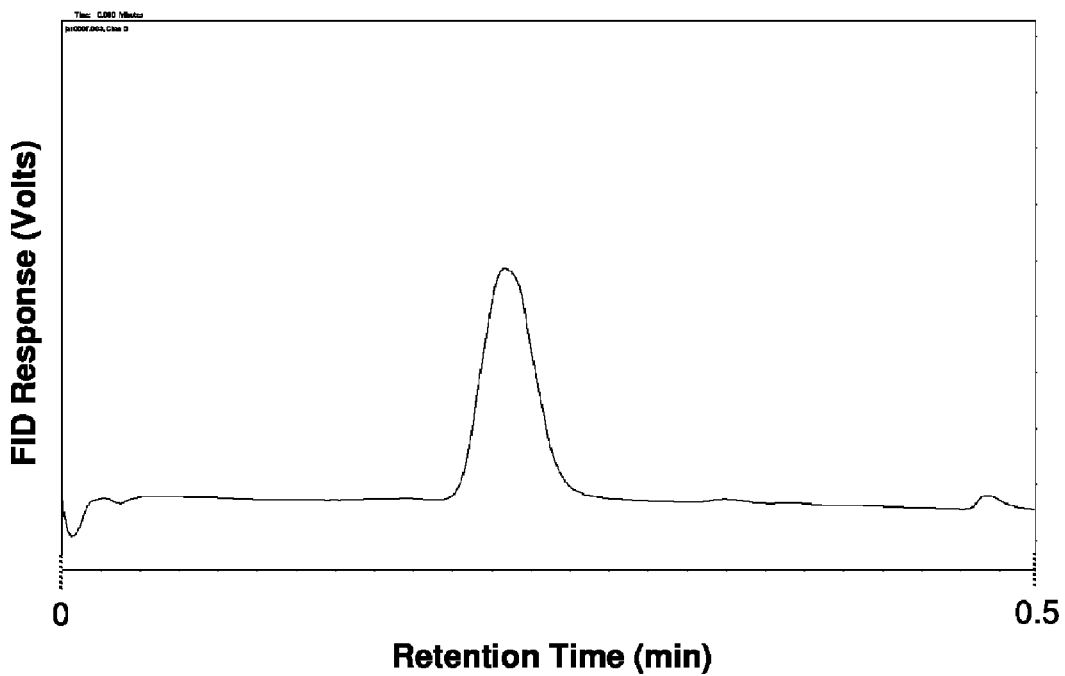
FIG. 48 is a chromatogram showing canola oil hydrolysates.
Figure 49:
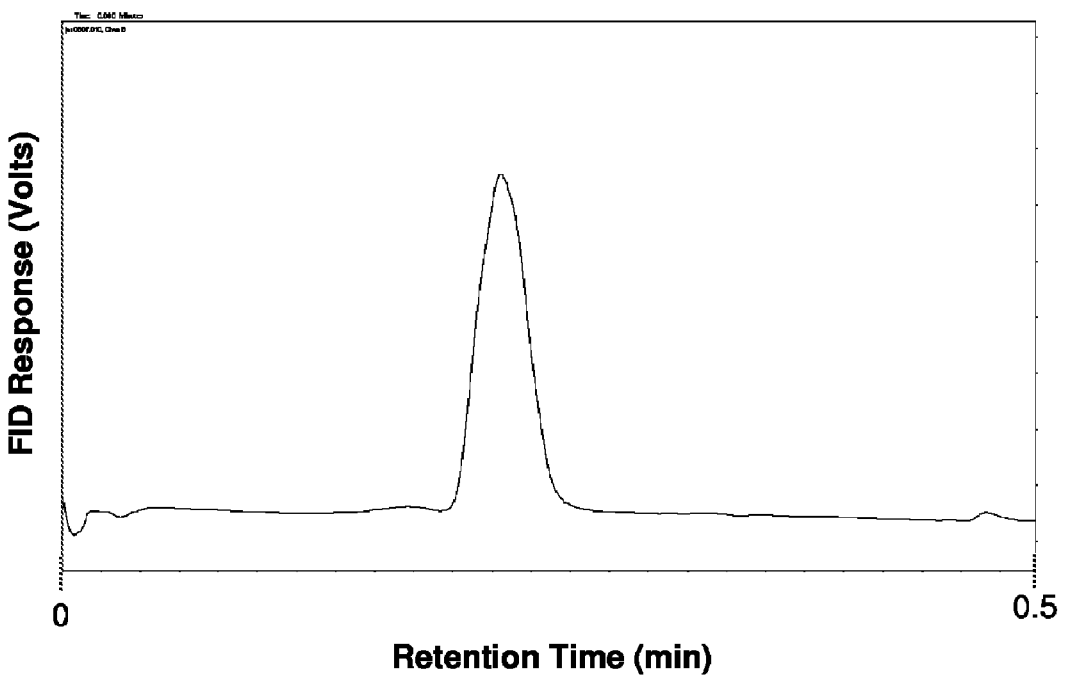
FIG. 49 is a TLC-FID chromatogram showing the bleached fancy hydrolysates.
Figure 50:
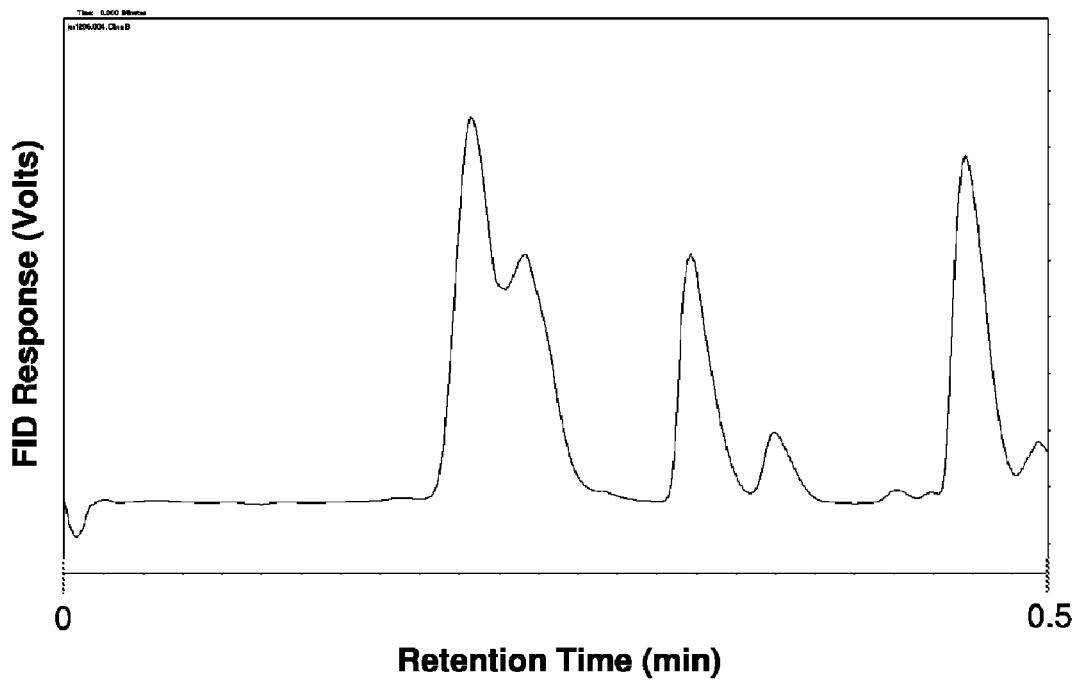
FIG. 50 is a TLC-FID chromatogram showing the oleic acid standard mixture.

VI. Hydrolysis and Pyrolysis of Neat Oils and Fats
Hydrolysate Analysis
TLC-FID Analysis FIGS. 48-52 show select chromatograms from the TLC-FID analysis of the hydrolysate fractions. FIG. 49 shows the chromatogram for the bleached fancy hydrolysates and FIG. 48 shows the chromatogram for the canola oil hydrolysates. It is clear that a single peak results likely indicating that only one type or class of lipid is present. Duplicate chromatograms (not shown) showed the same results. Because the conditions were severe and a single peak is evident, it is very likely that all of the TAG's are converted to FFAs. To confirm this, the retention times of different types of lipids were determined by analyzing a standard mixture of oleic acid TAG, DAG, MAG, and FFAs using the same method. These results are presented in FIG. 50. The chromarod analysis is such that the FID detector will scan down the rod. This means that the first peak to appear on the chromatogram (lowest scan time) will be the one that travels furthest up the rod during the TLC. In this case, the TAG fraction should appear first followed by the FFAs, DAGs and then MAGs. This is labeled on the standard curve and has been verified several times in other studies. The DAG and MAG peaks are clear, however, there is not great separation between the TAG and FFA peaks. It is evident that there are two separate peaks and that the TAG peak is larger than the FFA peak. The same trend has been shown in duplicate samples. Comparing the single peak from the samples and the standard, it is clear that the single peak aligns with the TAG and FFA peaks, however, because of the poor separation, it can not be stated conclusively that the samples contain nearly 100% FFA.

Figure 51:
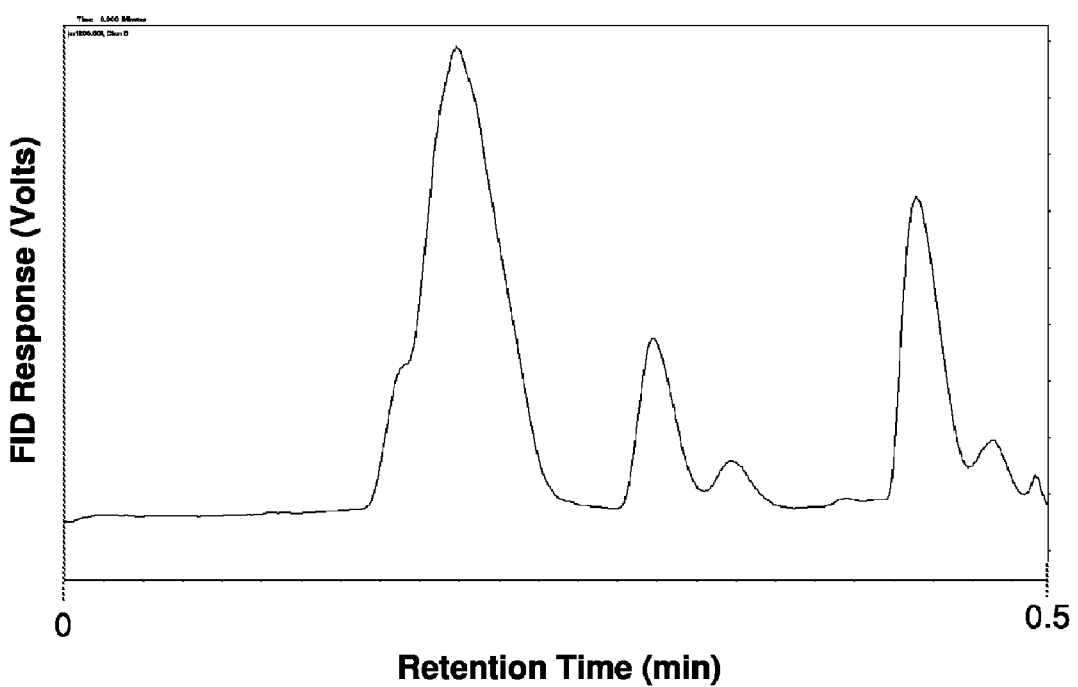
FIG. 51 is a TLC-FID chromatogram showing the oleic acid standard mixture spiked with bleached fancy hydrolysates (1:1 by volume standard:sample).
Figure 52:
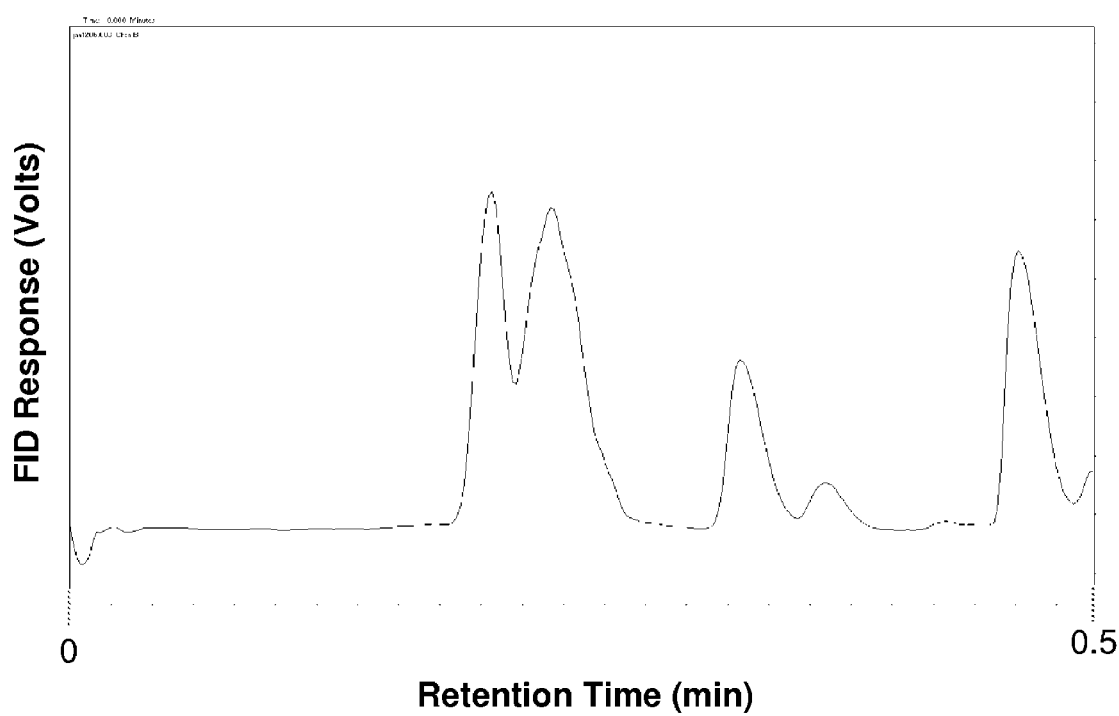
FIG. 52 is a TLC-FID chromatogram showing the oleic acid standard mixture spiked with bleached fancy hydrolysates (2:1 by volume standard:sample).

Because the results indicate that there are no intermediate DAG or MAG, the only other possibility is that the peak represents unreacted triglycerides. To confirm that the single peak does indeed represent FFA, samples were plotted on the chromarods and then spiked with standard. FIGS. 51 and 52 show that the when the sample is spiked with standard, the height of the FFA peak increases relative to the height of the triglyceride peak. In FIG. 51, equal volumes of sample and standard are plotted on the chromarods. Again there is not good separation, however, it does look like there are two peaks and that the second one is so large that it almost completely overlaps the first. This would indicate that the single peak from the sample is adding itself to the second FFA peak of the standard. FIG. 52 shows standard plotted with the standard with a ratio of 2:1 by volume standard/sample. In this case, there is better separation between the TAG and FFA peaks and the peaks appear to be nearly equal in size. Comparing this to the standard chromatogram, where the TAG peak is clearly larger than the FFA peak, it is evident that the single peak is adding itself to the second FFA peak from the standard. This indicates that the canola oil and bleached fancy hydrolysates are composed almost completely of FFA. It is assumed that the hydrolysates of the poultry tallow and the yellow grease are also composed predominantly of FFA. Although no lipid analysis was run on these hydrolysates, analysis of the pyrolysis fractions of all four oils and fats appeared similar.

GC-FID Analysis

Figure 53:
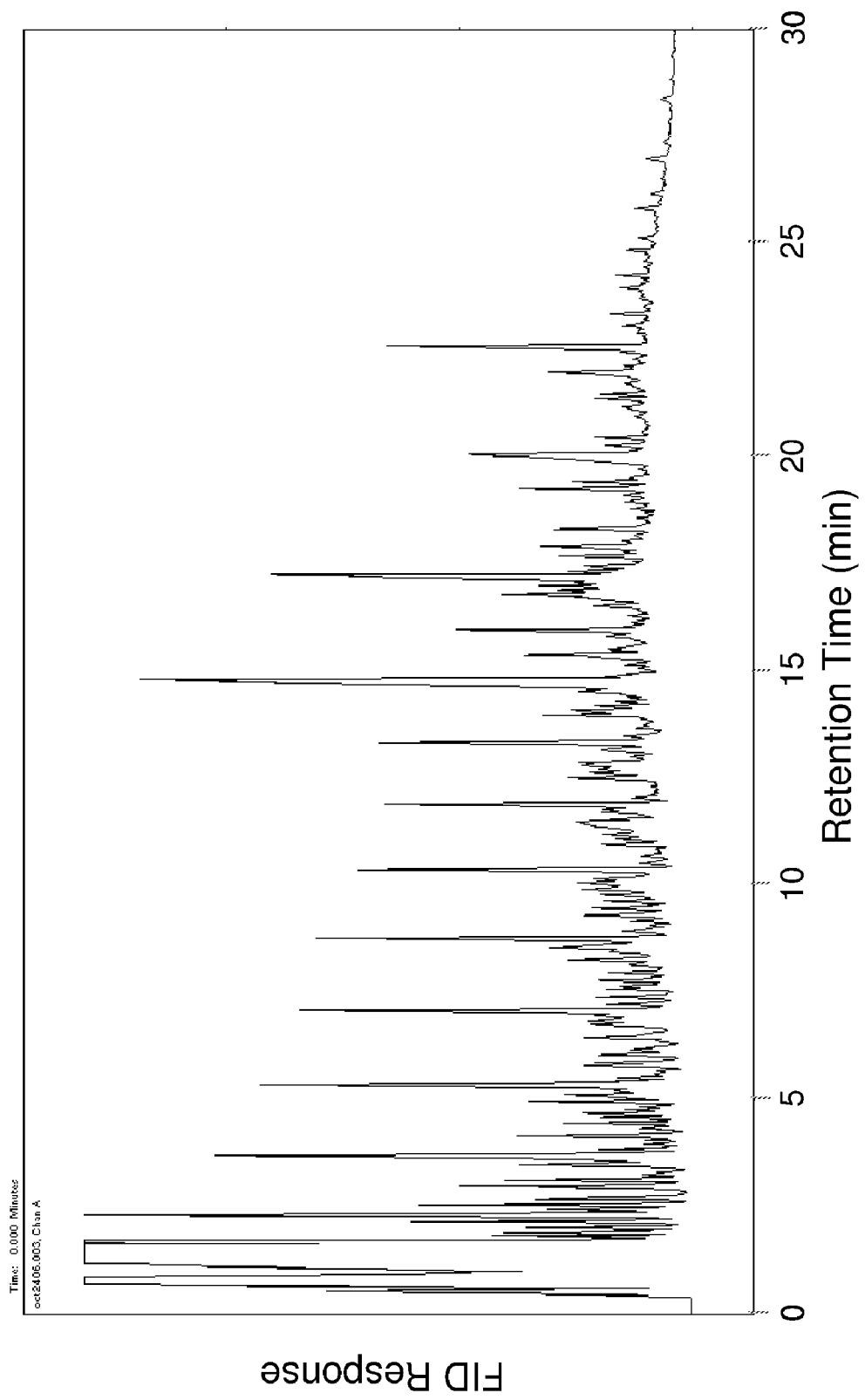
FIG. 53 is a GC-FID chromatogram showing poultry tallow pyrolysis products from a 4 hr reaction at 410° C., where reactions were conducted in $N_2$ atmosphere and were initially at atmospheric pressure.
Figure 54:
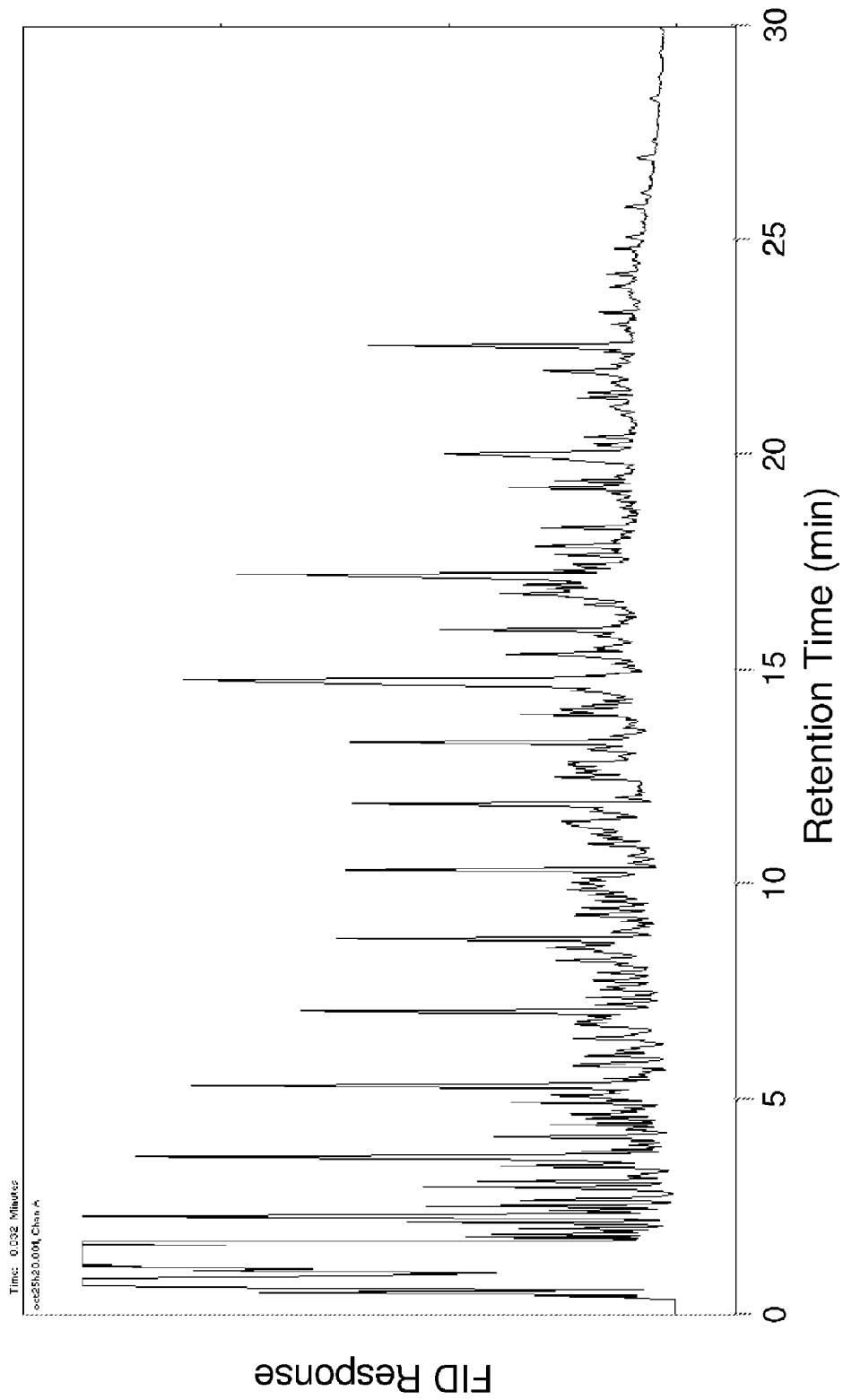
FIG. 54 is a GC-FID chromatogram showing poultry tallow pyrolysis products from a 4 hr reaction at 410° C. after a water extraction step, where the reactions were conducted in $N_2$ atmosphere and were initially at atmospheric pressure.
Figure 55:
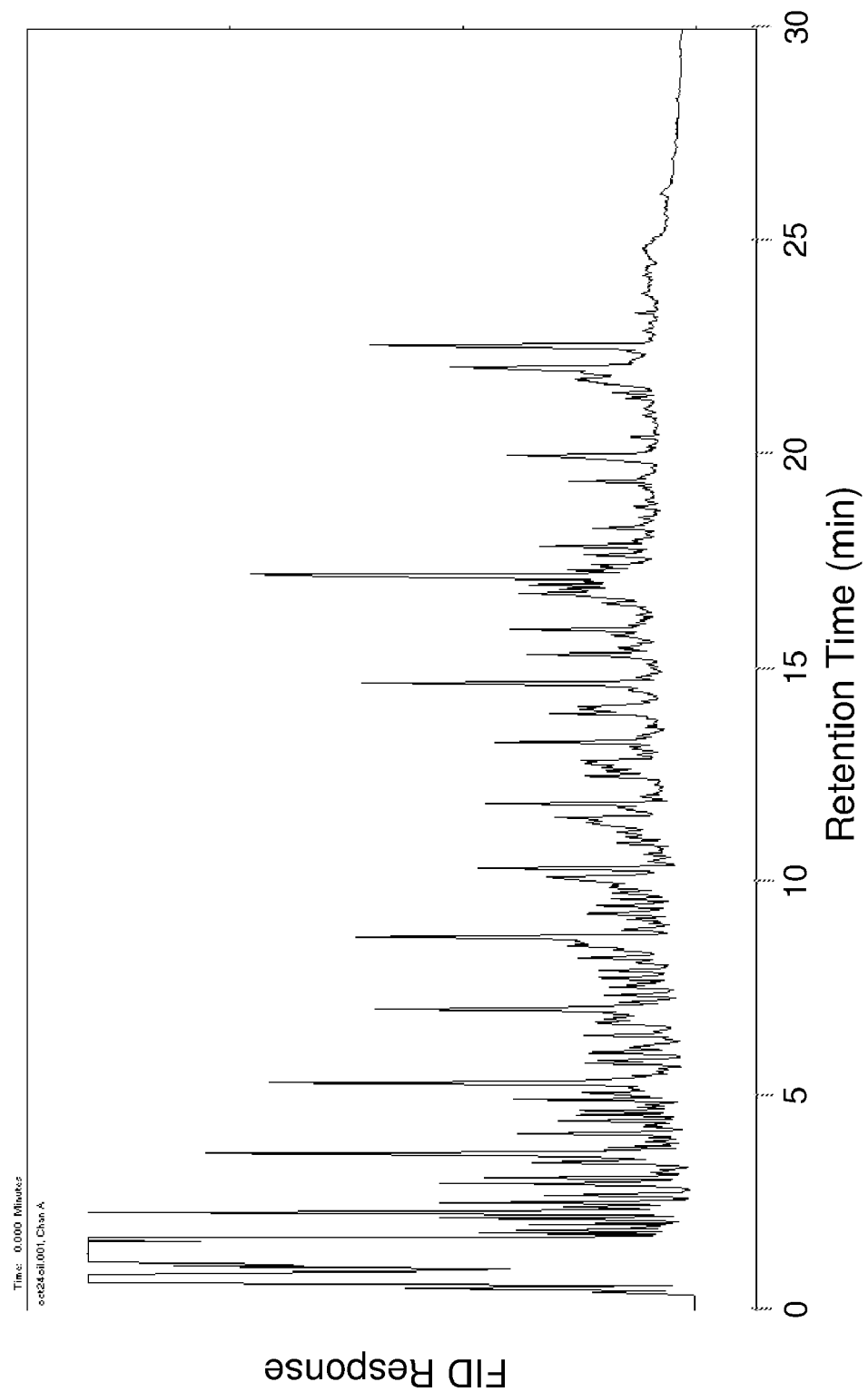
FIG. 55 is a GC-FID chromatogram showing canola tallow pyrolysis products from a 1 hr reaction at 410° C., where the reactions were conducted in $N_2$ atmosphere and were initially at atmospheric pressure.
Figure 56:
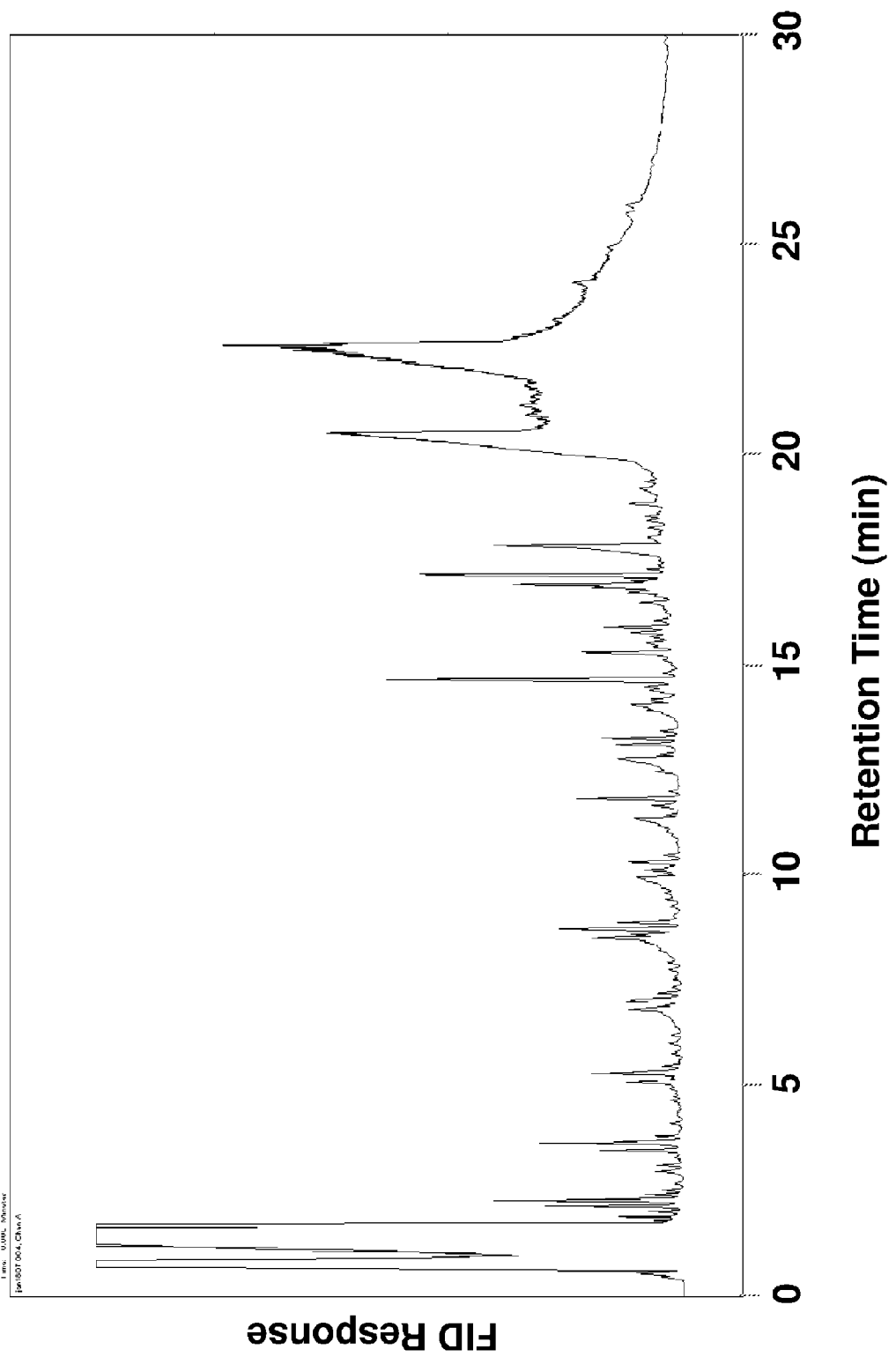
FIG. 56 is a GC-FID chromatogram showing bleached fancy pyrolysis products from a 1 hr reaction at 390° C., where the reactions were conducted in $N_2$ atmosphere and were initially at atmospheric pressure.

Initially, hydrolysates from poultry tallow were pyrolyzed for four hours at 410° C. as per normal procedures. The extracts were then analyzed on GC-FID. The chromatograms are presented in FIGS. 53 and 54. Canola oil, and two grades of beef tallow (Bleached Fancy (BF) and Yellow Grease (YG), were pyrolyzed at 410° C., but for one hour (FIG. 55). Bleached fancy hydrolysates were also pyrolyzed at 390° C. for one hour. The chromatograms from these reactions are presented in FIGS. 55 and 56. Note that the samples were prepared at different concentrations. Looking at the figures, the alkane/alkane ladder is prominent.

Figure 57:
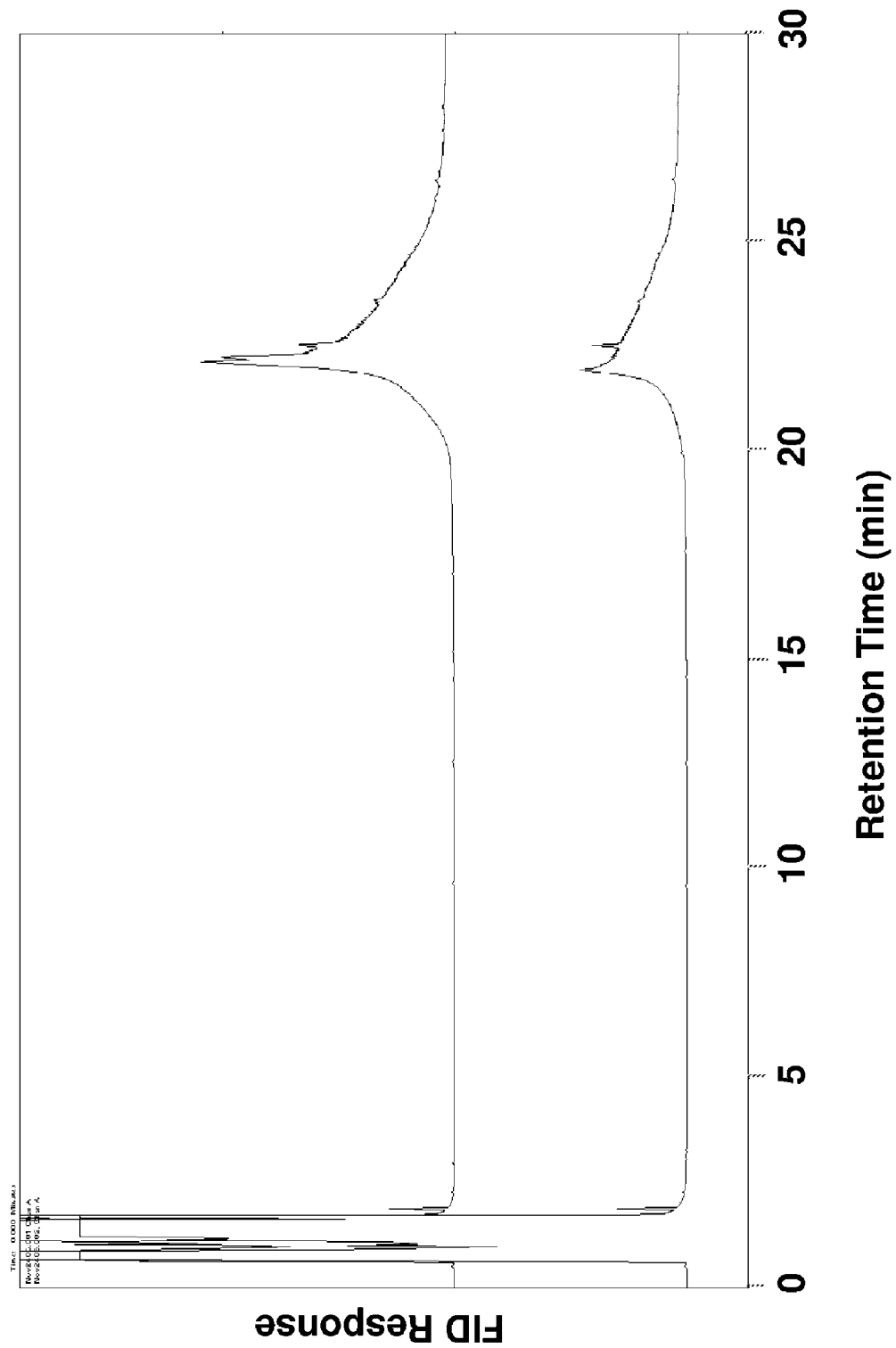
FIG. 57 is a GC-FID chromatogram showing bleached fancy hydrolysates from a 1 hr reaction at 410° C. dissolved in pentane, where the reactions were conducted in $N_2$ atmosphere and were initially at atmospheric pressure.

The chromatograms show that there are numerous compounds in between these ladders. The chromatograms of the neat oils and fats are not as clean as the chromatograms from the stearic acid pyrolysis. Numerous analyses of hydrolysates indicate the feedstock contains mainly free fatty acids. There was no evidence that there were large amounts of contaminants that may result in peaks shown in FIG. 56. To verify this, hydrolysates were dissolved in pentane and run on GC-FID (FIG. 57). A massive peak around at a retention time resulted. Due the spreading along the baseline, it is likely that this peak is composed of a mixture of fatty acids. No other peaks were evident. To see if any of the compounds in the pyrolysis products were water-soluble contaminants, a simple water extraction was conducted on the pyrolytic oil. After washing with water, the organic sample was separated and re-analyzed on GC-FID (FIG. 57). The figures are very similar, indicating that the water extraction had little effect on the extraction products. These simple experiments show that the peaks are organic in nature and are likely the result of the pyrolysis reaction. It is possible that the peaks are unreacted feed or lower carbon number free fatty acids. Since these have a tendency to spread on the baseline they are difficult to separate and result in poor baseline. Secondly, the results of the oleic acid analysis show that pyrolysis of unsaturated free fatty acids may result in the formation of numerous cyclic compounds.

GC/MS Analysis after Derivatization with Diazomethane

Figure 58:
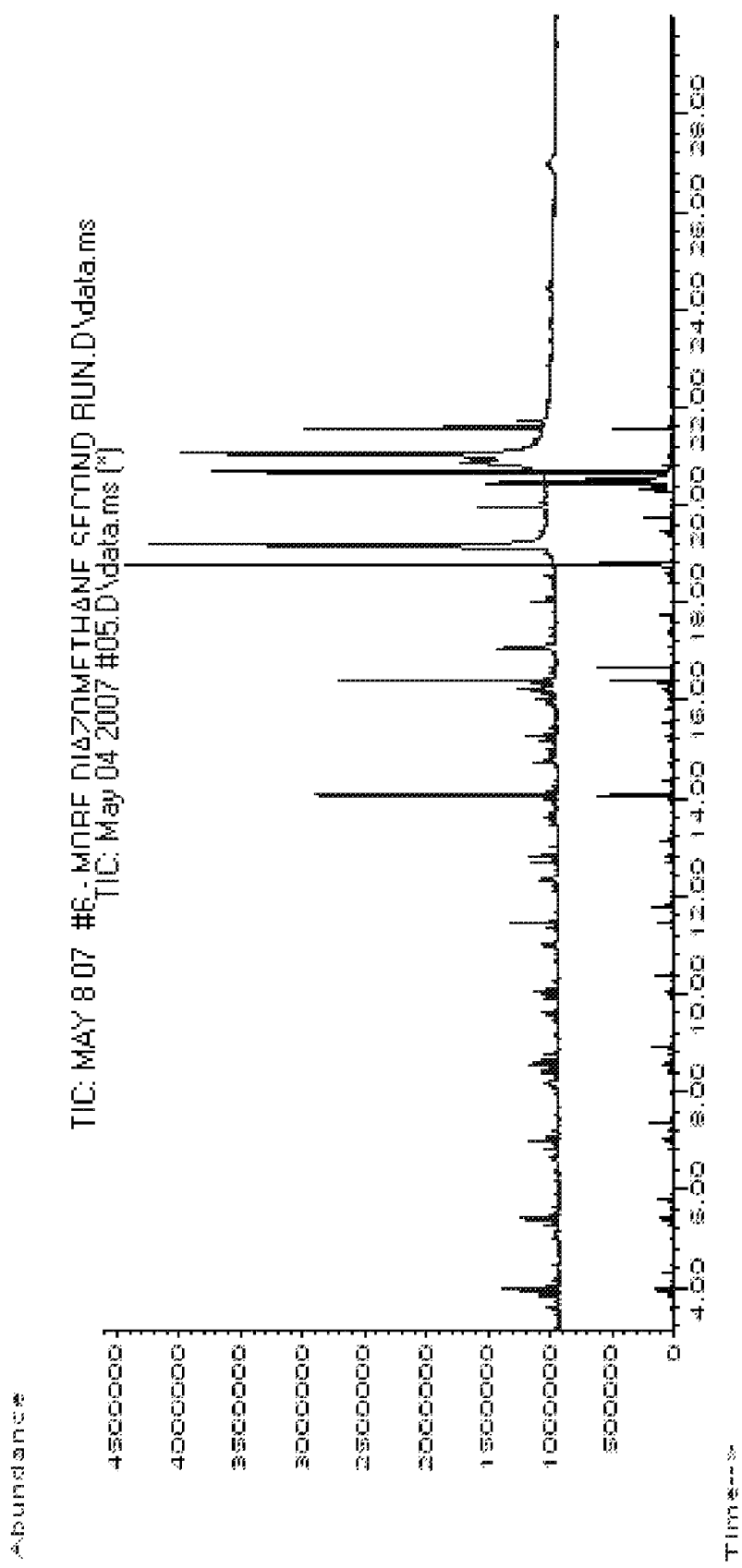
FIG. 58 is a GC/MS chromatogram showing derivatized and underivatized samples of bleached fancy pyrolysis products after 1 hr reaction at 410° C.
Figure 59:
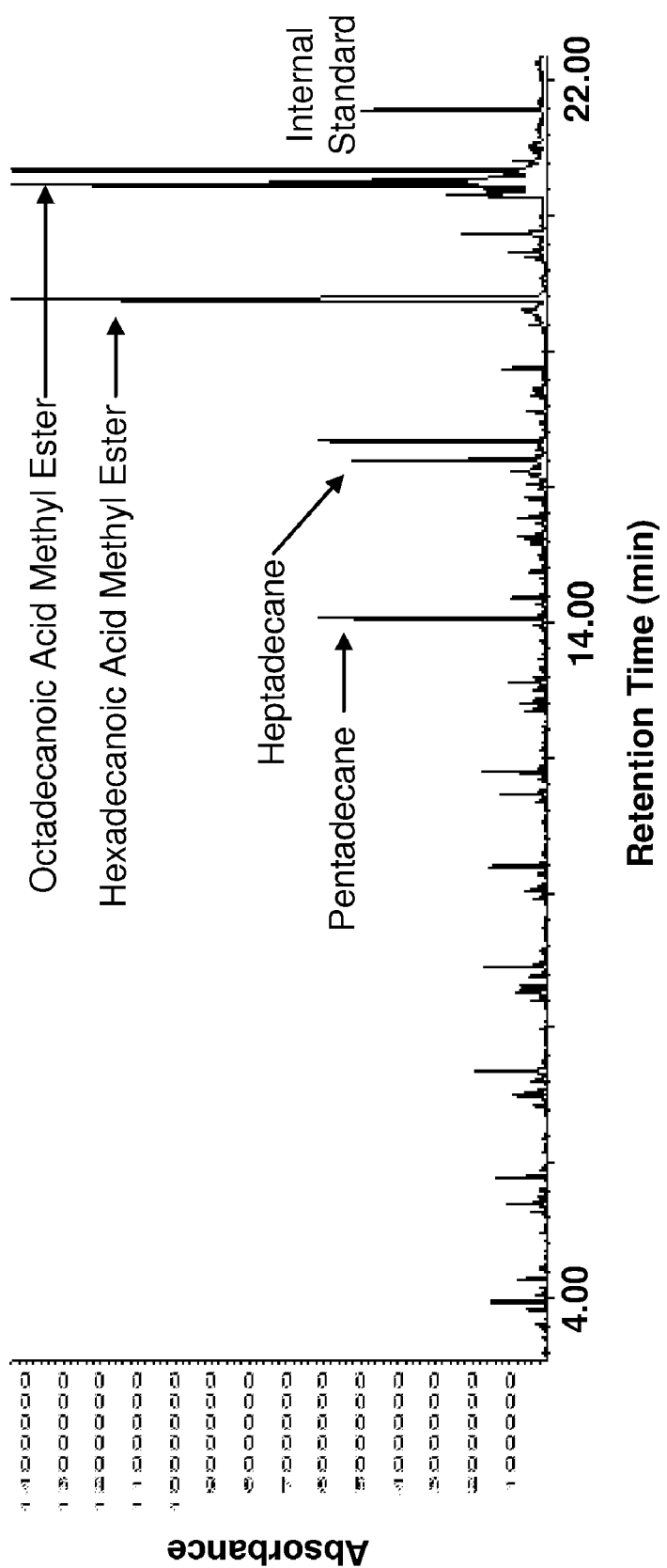
FIG. 59 is a GC/MS chromatogram showing derivatized bleached fancy pyrolysis products after 1 hr reaction at 410° C.
Figure 60:
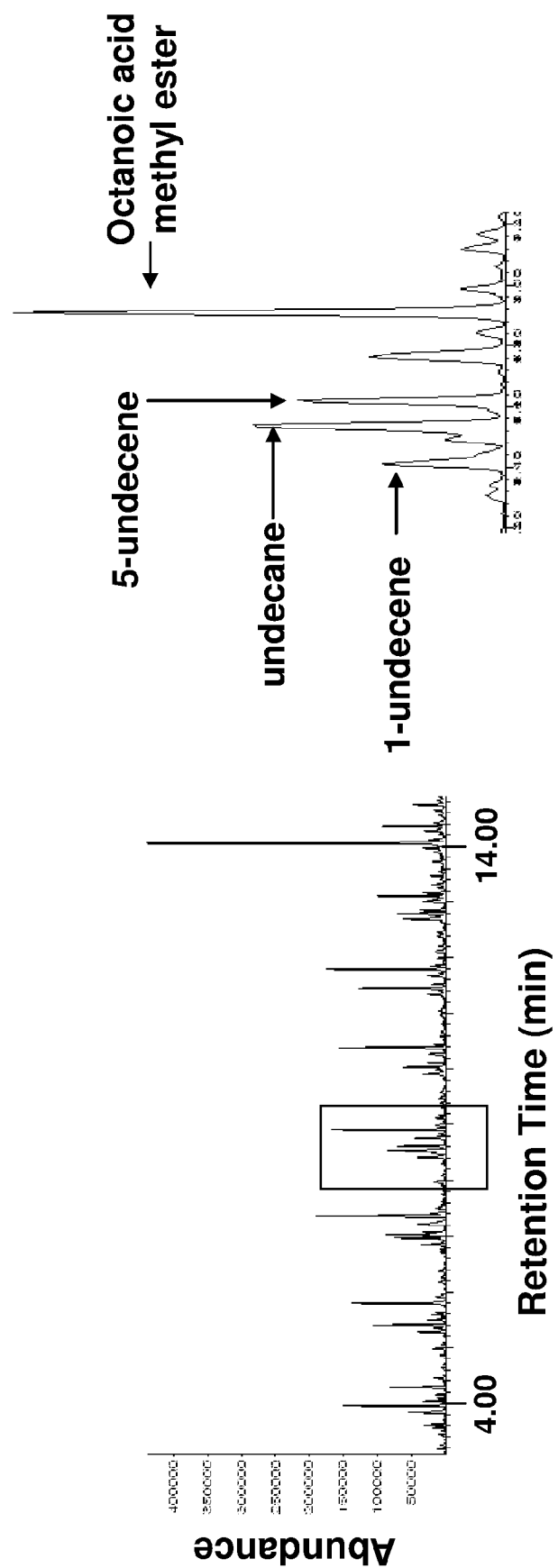
FIG. 60 is an expanded region of GC/MS chromatogram showing derivatized bleached fancy pyrolysis products after 1-hour reaction at 410° C.

As previously mentioned underivatized fatty acids do not result in clean sharp peaks on the GC column and conditions that were utilized in this work for the analysis of the hydrocarbon product and because they spread on the column they may overlap other compounds. Products were not routinely derivatized because of the potential risk of changing the product distribution during the derivatization process and also because the stearic acid feed resulted in relatively clean chromatograms where the fatty acids and hydrocarbons were clearly separated. The advantage to derivatizing these products would be to get a more accurate estimation of the fatty acid content. To estimate the unreacted feed this approach was taken as described previously, however in these cases the hydrocarbons were considered for analysis. Because the pyrolysis products from neat fats and oils contained many unidentified compounds, it was of interest to analyze them on GC/MS. In an attempt to purify the sample and eliminate any fatty acid spreading along the baseline, bleached fancy pyrolytic oil was first derivatized with diazomethane (without drying) and analyzed by GC/MS. An underivatized sample was also run to determine any effects of running the derivatized samples without the drying steps. These chromatograms are presented in FIG. 58-60.

Throughout this application, various publications are referenced. The disclosures of these publications in their entireties are hereby incorporated by reference into this application in order to more fully describe the compounds, compositions and methods described herein.

Various modifications and variations can be made to the materials, methods, and articles described herein. Other aspects of the materials, methods, and articles described herein will be apparent from consideration of the specification and practice of the materials, methods, and articles disclosed herein. It is intended that the specification and examples be considered as exemplary.

TABLE 1

List of chemicals used in study.

| Name | Catalogue Number | Manufacturer | Supplier |
|---|---|---|---|
| Pentane (HPLC Grade) | P399-4 | Fisher Chemicals | Fisher Scientific (Fair Lawn, NJ) |
| Toluene (HPLC Grade) | T290-4 | Fisher Chemicals | Fisher Scientific (Fair Lawn, NJ) |
| Nonadecanoic Methyl Ester (min 98%, GC) | N5377 | Sigma | Sigma-Aldrich Co. St. Louis, MO |
| Alkane Standard Solution $C_8$-$C_{20}$ | 04070 | Fluka | Sigma-Aldrich Co. St. Louis, MO |
| Carboxylic Acid Standard (GC) Solution | N/A | Sigma | Sigma-Aldrich Co. St. Louis, MO |
| Alumina, desiccant Grade H-152 | A-2935 | Sigma | Sigma-Aldrich Co. St. Louis, MO |
| Nitrogen, Compressed P.P. 4.8 | N/A | Praxair | Praxair, Edmonton, AB |
| Chloroform, HPLC Grade | C606-4 | Fisher Chemicals | Fisher Scientific (Fair Lawn, NJ) |
| Hexanes, HPLC Grade | H302-4 | Fisher Chemicals | Fisher Scientific (Fair Lawn, NJ) |
| Acetic Acid, glacial, ACS Reagent Grade | A-0808 | Sigma | Sigma-Aldrich Co. St. Louis, MO |
| TLC Standard, 25% (w/w) of each of oleic acid, monoolein, diolein and triolein | — | Nu-Chek Prep Inc. | Elysian, MN |
| Diethyl ether | | Fisher Chemicals | Fisher Scientific (Fair Lawn, NJ) |

TABLE 2

Fatty acid composition of the feed fats and oil

| | Fatty Acid (%) | | | | | | | | | |
|---|---|---|---|---|---|---|---|---|---|---|
| Feed Material | C14:0 | C16:0 | C16:1 cis | C17:0 | C18:0 | C18:1 trans | C18:1 cis | C18:2 | C20:0 | C18:3 | C22:0 |
| Bleached Fancy | 2.56 | 24.98 | 3.13 | 1.05 | 16.52 | 2.61 | 37.82 | 5.87 | 0.18 | 0.61 | — |
| Yellow Grease | 1.14 | 15.39 | 2.45 | 0.36 | 7.45 | 4.43 | 46.19 | 15.48 | 0.30 | 2.26 | 0.18 |
| Canola Oil | 0.07 | 5.10 | 0.29 | 0.06 | 2.21 | — | 63.63 | 17.33 | 0.62 | 6.91 | 0.30 |
| Poultry Tallow | 0.76 | 22.54 | 7.25 | 0.14 | 5.67 | 0.68 | 43.92 | 14.66 | 0.10 | 1.16 | 0.03 |

TABLE 3

Percentage of saturated and unsaturated fatty acid in feed fats and oil

| Feed Material | Saturates (%) | Monounsaturates (%) | Polyunsaturates (%) |
|---|---|---|---|
| Bleached Fancy | 46.22 | 44.76 | 7.24 |
| Yellow Grease | 25.37 | 54.18 | 18.43 |
| Canola Oil | 8.62 | 65.55 | 24.57 |
| Poultry Tallow | 29.62 | 52.55 | 16.95 |

TABLE 4

Sand bath specifications
Techne SBS-4 Sand Bath Specifications

| | |
|---|---|
| Overall Size (Diameter × Height), in | 13.2 × 18.2 |
| Working Volume (Diameter × Height), in | 7.0 × 5.5 |
| Temperature, ° C. | 50-600 |
| Temperature Stability @ 50° C. with TC-8D | ±0.3° C. |
| Air Pressure, PSI | 3 |
| Air Flow CFM | 3 |
| Weight of Media, lbs | 19.8 |

TABLE 5

Groups methylated by different derivatization compounds

| Derivitization Compound | Types of compounds methylated |
|---|---|
| Boron Trifluoride | TAG, DAG, MAG, FFA |
| Diazomethane | FFA |
| Sodium methoxide | TAG, DAG, MAG, FFA |
| Methanolic HCL | TAG, DAG, MAG |

TABLE 6

Experimental conditions for preliminary pyrolysis reactions.
X's indicate reactions were conducted at the specified conditions.

| Time (min) | Temperature (° C.) | | | | |
|---|---|---|---|---|---|
| | 350 | 400 | 450 | 500 | 550 |
| 30 | XX | XX | XX | XX | — |
| 5 | — | XX | XX | XX | XX |

TABLE 7

Experimental Conditions for the pyrolysis of stearic acid. X's indicate reactions conducted.

| Time (hr) | Temperature (° C.) | | | | | | |
|---|---|---|---|---|---|---|---|
| | 350 | 370 | 390 | 410 | 430 | 450 | 500 |
| 0.5 | — | — | XX | XX | XX | XX | XX |
| 1 | — | XX | XX | XX | XX | XX | XX |
| 4 | XX | XX | XX | XX | XX | XX | XX |
| 8 | XX | XX | XX | XX | XX | XX | — |

What is claimed:

1. A method for producing a fuel or solvent from a fatty acid resource, comprising:
    (a) separating one or more fatty acids from the fatty acid resource, wherein the fatty acids are greater than 90% by weight free fatty acids; and
    (b) heating the free fatty acids produced in step (a) under an inert atmosphere in the absence of a decarboxylation catalyst in order to convert all or substantially all of the free fatty acids to an alkane, an alkene, or a mixture thereof and carbon dioxide, wherein the heating step is conducted at a temperature from 220° C to 650° C.

2. The method of claim 1, wherein the fatty acid resource is selected from the group consisting of vegetable oil, animal fats, spent cooking oil, lipids, phospholipids, and triglycerides.

3. The method of claim 2, wherein the vegetable oil is selected from the group consisting of corn oil, cottonseed oil, canola oil, rapeseed oil, olive oil, palm oil, peanut oil, ground nut oil, safflower oil, sesame oil, soybean oil, sunflower oil, algae oil, almond oil, apricot oil, argan oil, avocado oil, ben oil, cashew oil, castor oil, grape seed oil, hazelnut oil, hemp seed oil, linseed oil, mustard oil, neem oil, palm kernel oil, pumpkin seed oil, rice bran oil, walnut oil, and a combination thereof.

4. The method of claim 2, wherein the animal fat is selected from the group consisting of blubber, cod liver oil, ghee, lard, tallow, a derivative thereof, and a combination thereof.

5. The method of claim 1, wherein step (a) comprises (i) separating one or more triglycerides from the vegetable oil or animal fat, and (ii) hydrolyzing the triglyceride to produce the free fatty acid, and (iii) isolating the free fatty acid.

6. The method of claim 1, wherein the fatty acid is selected from the group consisting of a saturated fatty acid, an unsaturated fatty acid, and a combination thereof.

7. The method of claim 1, wherein the fatty acid is selected from the group consisting of butyric acid, lauric acid, myristic acid, palmitic acid, stearic acid, arachidic acid, alpha-linolenic acid, docosahexaenoic acid, eicosapentaenoic acid, linoleic acid, arachidonic acid, oleic acid, erucic acid, a naturally derived fatty acid from a plant or animal source, and a combination thereof.

8. The method of claim 1, wherein prior to step (a), the fatty acid resource is further purified by extraction or distillation.

9. The method of claim 1, wherein the heating step is conducted at a pressure from ambient to 2,000 psi for a duration of two seconds up to 12 hours.

10. The method of claim 1, wherein the heating step is conducted at a temperature from 250° C to 500° C for two seconds up to 8 hours.

11. The method of claim 1, wherein the inert atmosphere is nitrogen or argon.

12. The method of claim 1, wherein steps (a) and (b) are continuous.

13. The method of claim 1, wherein the fuel or solvent is substantially free of aromatic compounds.

14. A method for producing a fuel or solvent from a fatty acid resource, comprising:
    (a) separating one or more fatty acids from the fatty acid resource, wherein the fatty acids are greater than 90% by weight free fatty acids; and
    (b) heating the free fatty acids produced in step (a) optionally under an inert atmosphere to convert all or substantially all of the free fatty acids to an alkane, an alkene, or a mixture thereof and carbon dioxide, wherein the heating step is conducted at a temperature from 220° C to 650° C,
    wherein the process is not performed in the presence of hydrogen.

15. The method of claim 14, wherein steps (a) and (b) are continuous.

* * * * *